(12) United States Patent
Corral-Debrinski et al.

(10) Patent No.: US 11,702,671 B2
(45) Date of Patent: *Jul. 18, 2023

(54) IMPORTATION OF MITOCHONDRIAL PROTEIN BY AN ENHANCED ALLOTOPIC APPROACH

(71) Applicant: INSTITUT NATIONAL DE LA SANTE ET DE LA RECHERCHE MEDICALE (INSERM), Paris (FR)

(72) Inventors: Marisol Corral-Debrinski, Montreuil (FR); Jose-Alain Sahel, Paris (FR); Valerie Kaltimbacher, Fontenay Sous Bois (FR); Crystel Bonnet, Montrouge (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/331,097

(22) Filed: May 26, 2021

(65) Prior Publication Data

US 2021/0292785 A1 Sep. 23, 2021

Related U.S. Application Data

(60) Continuation of application No. 16/574,685, filed on Sep. 18, 2019, now abandoned, which is a division of application No. 15/914,566, filed on Mar. 7, 2018, now abandoned, which is a continuation of application No. 14/676,846, filed on Apr. 2, 2015, now abandoned, which is a division of application No. 14/323,393, filed on Jul. 3, 2014, now abandoned, which is a division of application No. 11/913,618, filed as application No. PCT/EP2006/005323 on May 3, 2006, now Pat. No. 9,017,999.

(60) Provisional application No. 60/676,933, filed on May 3, 2005.

(51) Int. Cl.
| | |
|---|---|
| C12N 15/85 | (2006.01) |
| C12N 15/00 | (2006.01) |
| A61K 48/00 | (2006.01) |
| C12N 9/02 | (2006.01) |
| C07K 14/47 | (2006.01) |
| C12N 9/10 | (2006.01) |

(52) U.S. Cl.
CPC ............ *C12N 15/85* (2013.01); *A61K 48/005* (2013.01); *A61K 48/0058* (2013.01); *A61K 48/0066* (2013.01); *C07K 14/47* (2013.01); *C12N 9/0053* (2013.01); *C12N 9/0089* (2013.01); *C12N 9/1085* (2013.01); *C12N 15/8509* (2013.01); *C12Y 109/03001* (2013.01); *C07K 2319/07* (2013.01); *C12N 2800/22* (2013.01); *C12N 2810/80* (2013.01)

(58) Field of Classification Search
CPC ...................................................... C12N 15/85
See application file for complete search history.

(56) References Cited

U.S. PATENT DOCUMENTS

| | | | |
|---|---|---|---|
| 9,017,999 B2 | 4/2015 | Corral-Debrinski et al. | |
| 2004/0072774 A1* | 4/2004 | Manfredi ............. | C12N 9/0053 435/317.1 |

OTHER PUBLICATIONS

Oca-Cossio et al Genetics 165: 707-720 (Year: 2003).*
Margeot et al The EMBO J, 21, 6893-6904 (Year: 2002).*
Margeot et al Gene 354 64-71 (Year: 2005).*
Skolnick et al. TIBTECH 18:34-39 (Year: 2000).*
Corral-Debrinski et al Mol. and Cell Biology, 20(21), 7881-7892 (Year: 2000).*
Glerum et al Proc. natl. Acad. Sci, USA, 91, 8452-8456 (Year: 1994).*
Claros et al Eur. J. Biochem. 241, 779-786 (Year: 1996).*
NCBI Reference Sequence: NM_001303.2, dated Oct. 27,pp. 1-3 (Year: 2004).*
Mauro Trends Mol. Med. 20(11): 604-613 (Year: 2014).*
Carelli et al., "Mitochondrial dysfunction as a cause of optic neuropathies", Progress in Retinal and Eye Research, 2004, 23, pp. 53-89.
Claros et al., Eur. J. Biochem. 241, 779-786 1996.
Corral-Debrinski et al., "In Yeast, the 3' Untranslated Region or the Presequence of ATM1 is Required for the Exclusive Localization of its mRNA to the Vicinity of Mitochondria", Molecular and Cellular Biology, vol. 20, No. 21, Nov. 2000, pp. 7881-7892, XP002417806.
Ginsberg et al., "PKA-dependent Binding of mRNA to the Mitochondrial AKAP121 Protein", J. Mol. Biol., 2003, 327(4), pp. 885-897.
Ginsberg et al., Journal of Mol. Biol. 2003, 885-897.
Glerum et al., Proc. Natl. Acad. Sci, USA, 1994, 91, 8452-8456.
Guy et al., "Rescue of a Mitochondrial Deficiency Causing Leber Hereditary Optic Neuropathy", Ann. Neurol., 2002, 52, pp. 534-542.
M.C. Debrinsky et al., "Role of mRNA Localization to the Mitochondrial Surface in the Physiopathology of Retina", May 5, 2005, Abstract.
Margeot et al., Gene 354 (2005) 64-71.

(Continued)

*Primary Examiner* — Anoop K Singh
(74) *Attorney, Agent, or Firm* — Finnegan, Henderson, Farabow, Garrett & Dunner, LLP

(57) ABSTRACT

An expression vector containing appropriate mitochondrion-targeting sequences (MTS) and appropriate 3'UTR sequences provides efficient and stable delivery of a mRNA encoding a protein (CDS) to the mitochondrion of a mammalian cell. The MTS and 3'UTR sequences guide the CDS mRNA from the nuclear compartment of the cell to mitochondrion-bound polysomes, where the CDS is translated. This provides an efficient translocation of a mature functional protein into the mitochondria. A method of targeting mRNA expressed in the nuclear compartment of a mammalian cell to the mitochondrion is also provided. The vector and methods can be used to treat defects in mitochondrial function.

13 Claims, 33 Drawing Sheets

Specification includes a Sequence Listing.

(56) References Cited

OTHER PUBLICATIONS

Margeot et al., The EMBO J, 2002, 21, 6893-6904.
NCBI Reference Sequence: NM_001303.2, dated Oct. 27, 2004, pp. 1-3.
Oca-Cossio et al., "Limitations of Allotopic Expression of Mitochondrial Genes in Mammalian Cells", Genetics, vol. 165, No. 2, Oct. 2003, pp. 707-720, XP002417807.
Owen et al., "Recombinant Adeno-Associated Virus Vector-Based Gene Transfer for Defects in Oxidative Metabolism", Human Gene Therapy, 2000, 11, pp. 2067-2078.
Pesole et al., Nucleic Acid Research 2002, 30(1) 335-340.
Skolnick et al., TIBTECH 18:34-39, 2000.
Smith et al., "Strategies for Treating disorders of the mitochondrial genome", Biochimica et Biophysica ACTA, vol. 1659, No. 2-3, Dec. 6, 2004, pp. 232-239, XP004679179.
Sylvestre et al., "The Role of the 3' Untranslated Region in mRNA Sorting to the Vicinity of Mitochondria Is Conserved from Yeast to Human Cells", Molecular Biology of the Cell, vol. 14, No. 9, XP002417576Sep. 2003, pp. 3848-3856.
Vincens et al., 1996 Eur J Biochem 241, 779-786.

\* cited by examiner

*COX10MTS- nATP6*
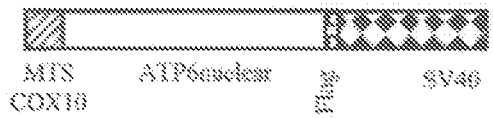
*SOD2MTS- nATP6*
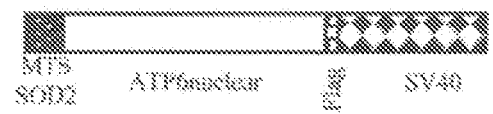
FIG.1A
*COX10MTS- nATP6- COX10 3'UTR*
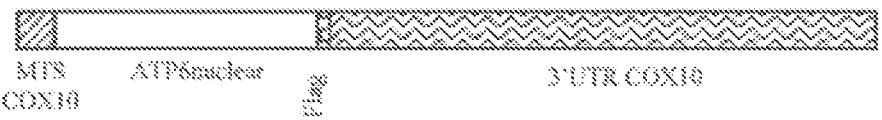
*SOD2MTS- nATP6- SOD2 3'UTR*
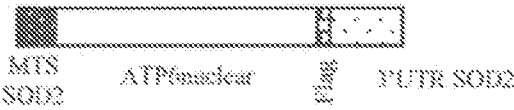
*COX10MTS- nATP6 (SEQ ID NO: 19)*
[DNA sequence]
FIG.1B (start)

FIG.1B (Cont'd)

FIG. 1B (end)

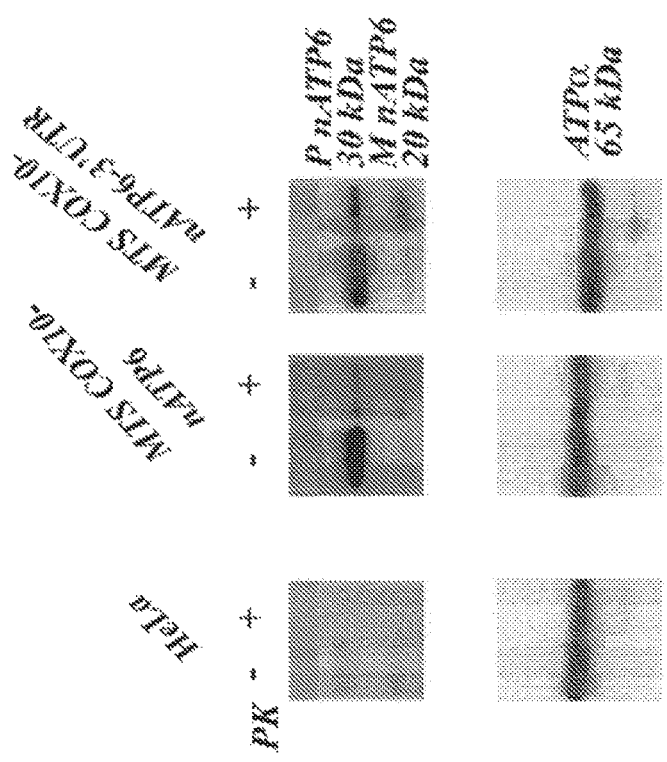
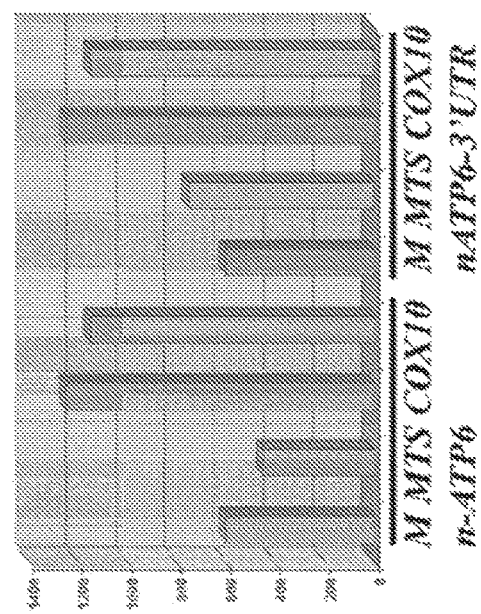
Figure 4A
Figure 4B

FIGURE 5B (Start)

COX10 MTS-nND1- COX10 3'UTR (SEQ ID NO :25)

FIGURE 9B (Cont'd)

*COX10 MTS-nND4- COX10 3'UTR* (SEQ ID NO 26)

GTCGACATGGCCGCCTCACCCCACACCCTGAGTAGCAGGCTGCTGACCGGCTGTGTGGGAGGAAGCGTCTGGTAT
CTGGAGCGGAGAACCATGCTGAAGCTGATCGTGCCCACCATTATGCTGCTGCCTCTGACATGGCTGTCTAAGAAG
CACATGATCTGGATTAACACAACCACCCACAGCCTGATTATCTCCATCATTCCCCTCCTGTTCTTCAACCAGATC
AACAACAACCTGTTCTCCTGCTCACCTACTTTTAGCAGCGATCCACTGACAACCCCACTGCTGATGCTGACAACC
TGGCTCCTCCCCCTGACAATCATGGCTTCCACAGGCACCTGAGCAGCCAGCCACTGTCCCGCAAAAGCTGTAC
GTGTCCATGCTGATTTCTCTCCAGATCTCACTCATCATGACCTTCACTGCCACCGAGCTGATTATGTTCTATATC
TTCTTCGAGACTACTCTGATCCCTACACTCGCCATTATCACCCGGTGGGGCAACCAGCCTGAGAGACTGAATGCC
GGACTTATTTTCTGTTCTACACCCTGGTGGGGTCACTGCCCCTGCTGATTGCCCTGATCTACACCCATAACACA
CTGGGCTCTCTCAATATCCTGCTGCTCACACTGACAGCCCAGGAGCTGTCCAATTCTTGGGCTAACAATCTGATG
TGGCTCGCATACACTATGGCCTTCATGGTGAAGATGCCACTCTATGGGCTCCACCTCTGGCTCCCTAAGGCCCAC
GTCGAAGCCCCAATTGCAGGGTCCATGGTGCTGGCAGCTGTGCTCCTGAAGCTGGGTGGCTATGGGATGATGCGC
CTGACCCTGATCCTGAATCCTCTCACAAAGCATATGGCTTACCCTTTCTGGTGCTGTCCCTGTGGGAATGATT
ATGACAAGCTCTATTTGCCTGCCCAGACAGACCTGAAAAGCCTGATTGCCCTACAGCAGTATCAGTCATATGGCC
CTGGTGGTGACCGCTATTCTGATTCAGACACCATGGTCTTTTACAGGGGCCGCTCATTCTGATGATCGCCCACGGA
CTGACCTCATCACTCCTCCTTCTGTCTGGCCAACTCAAACTACGAAAGGACACAGTCAAGAATTATGATTCTGAGC
CAGGGACTCCAGACTCTGCTCCCCCTCATGGCCGTTCTGGTGGCTGCTCGGCTCTCTCGGCAACCTGGCCCTGCCT
CCCACAATCAATCTGCTGGGGCGAGCTCAGCGTGCTGGTGGCCACTTTTAGTTGGTCCAACATCACACTGCTGCTC
ACCGGACTCAATATGCTGGTCACCGCCTGTACAGTCTGTACAATGTTCACCACAACACAGTGGGTAGCCTTCACT
CATCACATTAATAACATGAAGCCTTCTTTTACTAGGGAAAATACTCTGATGTTTATGCATCTCTCCCCAATCCTC
CTCCTGAGTCTGAACCCCGACATCATCACCGGCTTTAGCTCTCTGAGGAGGATTACAAGGATGACGACGATAAG
TAGGGCCGGGTACCTTAATTAATTAAGGTACCAGGTAAGTGTGCCAATTCCCCTATAGTGAGTCGTATTACAA
TTCACTGGATCGGAGCACTGGGACGCCCACCGGCCCTTTCCCTCCGCTGCCAGGCGAGCATGTTGTGGTAATTCT
GGAACACAAGAAGAGAAATTGCTGGGTTTAGAACAAGATTATAAACGAATTCGGTGCTCAGTGATCACTTGACAG
TTTTTTTTTTTTTAAATATTACCCAAAATGCTCCCCAAATAACAAATGCATCAGCTCAGTCAGTGAATACAAAA
AAGGAATTATTTTCCCTTTGAGGGTCTTTATACATCTCTCCTGCAACCCCAGCCTCTATTCTGTTGCTTCCTCC
TCACATGGGGGTACACATACACAGCTTCCTCTTTTTGTTCCATCCTTACCACCACACCACACGCACACTCCACAT
GCCCACCAGAGTGGCACTTGGTGGCCAGAAAGTGTGAGCCTCATGATCTGCTGTCTGTAGTTCTGTGAGCTCAGG
TCCCTCAAAGGCCTCGGAGCACCCCCTTCCTGGTGACTGAGCCAGGGCCTGCATTTTGTTTTCCCCACCCCAC
ACATTCTCAACCATAGTCCTTCTAACAATACCAATAGCTAGGACCCGGCTGCTGTGCACTGGGACTGGGATTCC
ACATGTTTGCCTTGGGAGTCTCAAGCCTGGACTGCCAGCCCCTGTCCTCCCTTCACCCCCATTGCGTATGAGCATT
TCAGAACTCCAAGGAGTCACAGGCATCTTTATAGTTCACGTTAACATATAGACACTGTTGGAAGCAGTTCCTTCT
AAAAGGGTAGCCCTGGACTTAATACCAGCCGGATACCTCTGGCCCCACCCCATTACTGTACCTCTGGAGTCACT
ACTGTGGCTCGCCACTCCTCTGCTACACAGCACGGCTTTTCAAGGCTGTATTGAGAAGGGAAGTTAGGAACAAG
GGTGTGCTGGCTAACCAGCCCACAGAGCTCACATTCCTGTCCTTGGCTAAAAATACATGTTCATCCTGATAT
CTCCTGAATTCAGAAATTAGCCTCCACATGTGCAATGGCTTTAAGAGCCAGAAGCAGGCTTCTGGGAATTTTGCA
AGTTATCCTGTGGCCAGGTGGTCTCGGTTACCAAATACGTTACCTGCAGCTTTTTAGTCGTTTAGTCCTGCTCCCA
GGGGTCTGTGAGAGTCCCATCTGGCCAAAGGTCTTGAAGGTTGACAGGATGTTTTCATTACTCAGTGTCCCAGGGC
ACTGCTGGTCCGTAGGGATTCATTGGTCGGGGTGGGAGAGTTAAACAACATTTAAACAGAGTTGTCTCAAAAATG
TCTAAAGGGATTGTAGGTAGATAACATCCAATCACTGTTTGCACTTATCTGAAATCTTCCCTCTTGGCTGCCCCC
AGGTATTTACTGTGGAGAACATTGCATAGCAATCTCTGAAAAAGCTTCTACAACTTGTTACAGGCCTTCACATTTG
TAGAAGCTTTACGCGT

FIGURE 5B (end)

nATP6 - SEQ ID NO:27
ATGAACGAAAATCTGTTCGCTTCATTCATTGCCCCCACAATCCTAGGCCTACCC
GCCGCAGTACTGATCATTCTATTTCCCCCTCTATTGATCCCCACCTCCAAATATC
TCATCAACAACCGACTAATCACCACCCAACAATGGCTAATCAAACTAACCTCAAA
ACAAATGATGACCATGCACAACACTAAAGGACGAACCTGGTCTCTTATGCTAGT
ATCCTTAATCATTTTTATTGCCACAACTAACCTCCTCGGACTCCTGCCTCACTCA
TTTACACCAACCACCCAACTATCTATGAACCTAGCCATGGCCATCCCCTTATGG
GCGGGCACAGTGATTATGGGCTTTCGCTCTAAGATTAAAAATGCCCTAGCCCAC
TTCTTACCACAAGGCACACCTACACCCCTTATCCCCATGCTAGTTATTATCGAAA
CCATCAGCCTACTCATTCAACCAATGGCCCTGGCCGTACGCCTAACCGCTAACA
TTACTGCAGGCCACCTACTCATGCACCTAATTGGAAGCGCCACCCTAGCAATGT
CAACCATTAACCTTCCCTCTACACTTATCATCTTCACAATTCTAATTCTACTGACT
ATCCTAGAAATCGCTGTCGCCTTAATCCAAGCCTACGTTTTCACACTTCTAGTAA
GCCTCTACCTGCACGACAACACAGCGGCCGCCCGGAAGGGC nND1 - SEQ ID NO:28
ATGCCAATGGCAAATCTGCTGCTCCTCATCGTGCCAATCCTGATCGCCATGGCC
TTCCTCATGCTGACTGAAAGAAAAATTCTGGGATACATGCAGCTCAGGAAGGGG
CCTAACGTGGTGGGACCTTATGGACTGCTCCAGCCCTTTGCTGATGCTATGAAG
CTGTTCACAAAAGAGCCCCTGAAACCAGCCACCTCTACAATCACCCTGTACATT
ACCGCTCCTACCCTGGCTCTGACAATTGCCCTGCTGCTGTGGACCCCTCTCCCT
ATGCCAAATCCTCTGGTGAACCTGAATCTGGGCCTCCTCTTTATCCTGGCCACC
AGCAGCCTGGCCGTGTACTCCATCCTGTGGAGCGGATGGGCTTCTAACAGCAA
TTACGCCCTGATCGGTGCCCTGAGGGCCGTGGCCCAGACCATTTCTTACGAGG
TGACCCTCGCCATTATCCTGCTCTCAACCCTGCTGATGAGCGGCTCTTTCAACC
TCTCAACCCTGATTACAACCCAGGAGCACCTCTGGCTGCTCCTCCCCAGCTGGC
CACTGGCCATGATGTGGTTTATCAGCACCCTGGCTGAGACAAACCGGACCCCC
TTTGATCTGGCTGAGGGCGAGTCTGAGCTGGTCTCCGGATTCAATATTGAGTAC
GCAGCAGGGCCATTCGCTCTGTTCTTCATGGCCGAGTATACAAATATTATTATGA
TGAACACACTGACTACTACTATCTTCCTGGGTACTACATACGATGCTCTGAGTCC
CGAACTCTACACCACTTACTTCGTGACCAAAACCCTGCTGCTGACTAGCCTGTT
CCTGTGGATCAGGACCGCCTATCCACGATTCCGATACGACCAGCTGATGCATCT
GCTGTGGAAGAACTTCCTGCCACTCACCCTGGCTCTGCTCATGTGGTACGTGAG
TATGCCAATCACTATCAGCTCTATCCCTCCACAGACCTA

FIGURE 9 nND4- SEQ ID NO:29
ATGCTGAAGCTGATCGTGCCCACCATTATGCTGCTGCCTCTGACATGGCTGTCT
AAGAAGCACATGATCTGGATTAACACAACCACCCACAGCCTGATTATCTCCATCA
TTCCCCTCCTGTTCTTCAACCAGATCAACAACAACCTGTTCTCCTGCTCACCTAC
TTTTAGCAGCGATCCACTGACAACCCCACTGCTGATGCTGACAACCTGGCTCCT
CCCCCTGACAATCATGGCTTCCCAGAGGCACCTGAGCAGCGAGCCACTGTCCC
GCAAAAGCTGTACCTGTCCATGCTGATTTCTCTCCAGATCTCACTCATCATGAC
CTTCACTGCCACCGAGCTGATTATGTTCTATATCTTCTTCGAGACTACTCTGATC
CCTACACTCGCCATTATCACCCGGTGGGGCAACCAGCCTGAGAGACTGAATGC
CGGGACTTATTTTCTGTTCTACACCCTGGTGGGGTCACTGCCCCTGCTGATTGC
CCTGATCTACACCCATAACACACTGGGCTCTCTCAATATCCTGCTGCTCACACT
GACAGCCCAGGAGCTGTCCAATTCTTGGGCTAACAATCTGATGTGGCTCGCATA
CACTATGGCCTTCATGGTGAAGATGCCACTCTATGGGCTCCACCTCTGGCTCCC
TAAGGCCCACGTCGAAGCCCCAATTGCAGGGTCCATGGTGCTGGCAGCTGTGC
TCCTGAAGCTGGGTGGCTATGGGATGATGCGCCTGACCCTGATCCTGAATCCT
CTCACAAAGCATATGGCTTACCCTTTTCTGGTGCTGTCCCTGTGGGGAATGATT
ATGACAAGCTCTATTTGCCTGCGCCAGACAGACCTGAAAAGCCTGATTGCCTAC
AGCAGTATCAGTCATATGGCCCTGGTGGTGACCGCTATTCTGATTCAGACACCA
TGGTCTTTTACAGGGGCCGTCATTCTGATGATCGCCCACGGACTGACCTCATCA
CTCCTCTTCTGTCTGGCCAACTCAAACTACGAAAGGACACACTCAAGAATTATGA
TTCTGAGCCAGGGACTCCAGACTCTGCTCCCCCTCATGGCCTTCTGGTGGCTG
CTCGCCTCTCTCGCCAACCTGGCCCTCCCTCCCACAATCAATCTGCTGGGCGA
GCTCAGCGTGCTGGTGACCACTTTTAGTTGGTCCAACATCACACTGCTGCTCAC
CGGACTCAATATGCTGGTCACCGCCCTGTACAGTCTGTACATGTTCACCACAAC
ACAGTGGGGTAGCCTCACTCATCACATTAATAACATGAAGCCTTCTTTTACTAGG
GAAAATACTCTGATGTTTATGCATCTCTCCCCAATCCTCCTCCTGAGTCTGAACC
CCGACATCATCACCGGCTTTAGCTCT

FIGURE 9 (end)

COX10 MTS- SEQ ID NO: 30
ATGGCCGCATCTCCGCACACTCTCTCCTCACGCCTCCTGACAGGTTGCGTAGG
AGGCTCTGTCTGGTATCTTGAAGTCGACCGC

COX10 3'UTR- SEQ ID NO: 47
GAGCACTGGGACGCCCACCGCCCCTTTCCCTCCGCTGCCAGGCGAGCATGTTG
TGGTAATTCTGGAACACAAGAAGAGAAATTGCTGGGTTTAGAACAAGATTATAAA
CGAATTCGGTGCCCAGTGATCACTTGACAGTTTTTTTTTTTTTAAATATTACCCA
AAATGCTCCCCAAATAAGAAATGCATCAGCTCAGTCAGTGAATACAAAAAAGGAA
TTATTTTTCCCTTTGAGGGTCTTTATACATCTCTCCTCCAACCCCACCCTCTATTC
TGTTTCTTCCTCCTCACATGGGGGTACACATACACAGCTTCCTCTTTTGGTTCCA
TCCTTACCACCACACCACACGCACACTCCACATGCCCAGCAGAGTGGCACTTG
GTGGCCAGAAAGTGTGAGCCTCATGATCTGCTGTCTGTAGTTCTGTGAGCTCAG
GTCCCTCAAAGGCCTCGGAGCACCCCCTTCCTGGTGACTGAGCCAGGGCCTGC
ATTTTTGGTTTTCCCCACCCCACACATTCTCAACCATAGTCCTTCTAACAATACCA
ATAGCTAGGACCCGGCTGCTGTGCACTGGGACTGGGGATTCCACATGTTTGCC
TTGGGAGTCTCAAGCTGGACTGCCAGCCCCTGTCCTCCCTTCACCCCCATTGC
GTATGAGCATTTCAGAACTCCAAGGAGTCACAGGCATCTTTATAGTTCACGTTAA
CATATAGACACTGTTGGAAGCAGTTCCTTCTAAAAGGGTAGCCCTGGACTTAATA
CCAGCCGGATACCTCTGGCCCCCACCCCATTACTGTACCTCTGGAGTCACTACT
GTGGGTCGCCACTCCTCTGCTACACAGCACGGCTTTTTCAAGGCTGTATTGAGA
AGGGAAGTTAGGAAGAAGGGTGTGCTGGGCTAACCAGCCCACAGAGCTCACAT
TCCTGTCCCTTGGGTGAAAAATACATGTCCATCCTGATATCTCCTGAATTCAGAA
ATTAGCCTCCACATGTGCAATGGCTTTAAGAGCCAGAAGCAGGGTTCTGGGAAT
TTTGCAAGTTATCCTGTGGCCAGGTGTGGTCTCGGTTACCAAATACGGTTACCT
GCAGCTTTTAGTCCTTTGTGCTCCCACGGGTCTGCAGAGTCCCATCTGCCCAA
AGGTCTTGAAGCTTGACAGGATGTTTTCATTACTCAGTCTCCCAGGGCACTGCT
GGTCCGTAGGGATTCATTGGTCGGGGTGGGAGAGTTAAACAACATTTAAACAGA
GTTCTCTCAAAAATGTCTAAAGGGATTGTAGGTAGATAACATCCAATCACTGTTT
GCACTTATCTGAAATCTTCCCTCTTGGCTGCCCCAGGTATTTACTGTGGAGAA
CATTGCATAGGAATGTCTGGAAAAAGCTCCTACAACTTGTTACAGCCTTCACATT
TGTAGAAGCTTT

SOD2 MTS- SEQ ID NO: 31
ATGTTGAGCCGGGCAGTGTGCGGCACCAGCAGGCAGCTGGCTCCGGTTTTGG
GGTATCTGGGCTCCAGGCAGAAGCACAGCCTCCCCGACGCGGTCGACCGC

SOD2 3'UTR- SEQ ID NO: 35
TTATGCTGAGTATGTTAAGCTCTTTATGACTGTTTTTGTAGTGGTATAGAGTACTG
CAGAATACAGTAAGCTGCTCTATTGTAGCATTTCCTGATGTTGCTTAGTCACTTA
TTTCATAAACAACTTAATGTTCTGAATAATTTCTTACTAAACATTTTGTTATTGGGC
AAGTGATTGAAAATAGTAAATGCTTTGTGTGATT

FIGURE 10

Aconitase (ACO2)
Accession number: NP_001089

Protein Sequence: 780 aa (SEQ ID NO: 48)
mapysllvtr lqkalgvrqy hvasvlcqra kvamshfepn eyihydllek niniivrkrln
rpltlsekiv yghlddpasq eiergksylr lrpdrvamqd ataqmamlqf isglskvav
pstlhcdhli eaqvggekdl rnakdinqev ynflatagak ygvgfwkpgs glihqillen
yaypgvllig tdshtpnggg lggiclgvgg adavdvmagi pwelkcpkvi gvkltgslsg
wsspkdvllk vagiltvkgg tgaiveyhgp gvdsisclgm aticnmgaei gattsvfpyn
hrmkkylskt grediantad efkdhlvpdp gchydqllel nlselkphin gpftpdlahp
vaevgkvaek egwpldirvg ligsctnssy edmgrsaava kqalahglkc ksqftitpgs
eqiratlerd gyaqilrdlg glvlanacgp clgqwdrkdl kkgekntivt synmftgrn
danpethafv tspelvtala iagllkfnpe tdyltgtdgk klrleapdad elpkgefdpg
qdtyqhppkd ssgqhvdvsp tsqrlqllep fdkwdgkdle dlqliikvkg kcttdhisaa
gpwlkfrghl dnlsnnllig ainlengkan svmavtqef gpvpdtaryy kkhgirwvvi
gdenygegss rehaaleprh lggrailtks fariihetnlk kqgllplifa dpadynkihp
vdkltlqglk dftpgkplkc lkhpngtqe tillnhtfne tqiewfrags alnrmkelqq
//

MTS sequence
Net charge of query sequence: +0
Analyzed region: 37
Number of basic residues in targeting sequence: 5
Number of acidic residues in targeting sequence: 0
Cleavage site: 31
Cleaved sequence: MAPYSLLVTRLQKALGVRQYHVASVLCQRA (SEQ ID NO: 32)

3'UTR sequence (Accession # CC373828; SEQ ID NO: 33)
```
gggcagtgcc tcccgcccc gccgctggcg tcaagatcag ctccacgtgt gccatcagtg      60
gatccgatcc gtccagccat ggcttcctat tccaagagg tgtgaccaga catgctcct     120
gctcccgct tagcccacgg agtgactgtg grtgtggtgg gggggttctt aaataaaclt    180
ttagcccca gtcttcctat tttgagtttg gtcaagatct taagcagctc catgcaactg    240
tactttatttt tgatgacaag aatcccatct aaagttttttc tccgcctga tcattcact    300
gtggctgaa ggactctaga gacctttttg ttcttgcaag gaaacaaga atccaaacc      360
agaaaaaaaa aaaaaaaaa aa                                              382
//
```

FIGURE 11A

Superoxide dismutase mitochondriale (SOD2)
Accession number: P04179

Protein Sequence: 222 aa (SEQ ID NO: 49)
mlsravcgts rqlapalgyl gsrqkhslpd lpydygalep hinaqimqlh hskhhaayvn
nlnvteekyq ealakgdvta qialqpalkf ngghinhsi fwtnlspngg gepkgellea
ikrdfgsfdk fkekltaasv gvqgsgwgwl gfnkerghlq iaacpnqdpl qgttglipll
gidvwehayy lqyknvrpdy lkaiwnvinw enverymac kk

MTS sequence
Net charge of query sequence:           +2
Analyzed region:                         29
Number of basic residues in targeting sequence:    4
Number of acidic residues in targeting sequence:   0
Cleavage site:                           21
Cleaved sequence: MLSRAVCGTSRQLAPALGYL (SEQ ID NO: 34)

3'UTR sequence (Accession # CC263966; SEQ ID NO: 35)
```
accacgatcg ttatgctgat catacccta tgatcccagc aagataacgt cctgtcttct      60
aagatgtgca tcaagcctgg tacatactga aaacctata aggtcctgga taatttttgt    120
ttgattattc attgaagaaa cattatttc ccaattgtgt gaagttttcg actgttaata    180
aagaatctg tcaaccatca aaaaaaaaa aaaa                                  214
//
```

<u>FIGURE 11 B</u>

ATP synthase subunit beta (ATP5b)
Accession number: NP_001677

Protein sequence: 529 aa (SEQ ID NO: 50)
mlgfvgrvaa apasgalrrl tpsaslppaq lllraaplav hpvrdyaaqt spspkagaat
grivavigav vdvqfdeglp pilnalevgg retrivleva qhlgestvrt lamdgteglv
rgqkvldsga pikipvgpet lgrimnvige pidergpikt kqfaplhaea pefmemsveq
eilvtgikvv dllapyakgg kiglfggagv gktvlimell nnvakahggy svfagvgert
regndlyhem iesgvinlkd atskvalvyg qmneppgara rvaltgltva eyfrdqegqd
vllfidnifr ftqagsevsa llgripsavg yqptlatdmg tmqeritttk kgsitsvqai
yvpaddltdp apattfahld attvlsraia elgiypavdp ldstsrimdp nivgsehydv
argvqkilqd yksiqdilai lgmdelseed kltvsrarki qrflsqpfqv aevftghmgk
lvplketikg fqqilageyd hlpeqafymv gpieeavaka dkiaeehss MTS sequence
Net charge of query sequence: -15
Analyzed region: 71
Number of basic residues in targeting sequence: 7
Number of acidic residues in targeting sequence: 1
Cleavage site: 64
Cleaved sequence:
MLGFVGRVAAAPASGALRRLTPSASLPPAQLLLRAAPTAVHPVRDYAAQTSPSP
KAGAATGRI (SEQ ID NO: 36)

3'UTR sequence (Accession # CC313884; SEQ ID NO: 37)
gggtctttg tctctgtcc tgtctctctc cttgccccta acccaaaaag cttcattttc    60
ctgtgaggc tgcacaagag cctgattga agaatattc tttctgaaca gtatttaagg   120
ttccaataa aatgtacacc cctcagaaaa aaaaaaaaaa aa                    162

FIGURE 11 C

Ubiquinol-cytochrome c reductase, Rieske iron-sulfur polypeptide 1 (UQCRFS1)
Accession number: NP_005994

Protein sequence: 274 aa (SEQ ID NO: 51)
mlsvaarsgp fapvlsatsr gvagalrplv qatvpatpeq pvldlkrpfl sreslsgqav
rplvasvgl nvpasvcysh tdlkvpdfse ymlevldst kseresseear kgfsylvtgv
ftvgvayaak navtqfvssm sasadvlala kielkladip egknmafkwr gkplfvrhrt
qkeieqeaav elsqlrdpqh dldrvkkpew viligvcthl gcvpianagd fggyycpchg
shydasgrir tgpapinlev ptyeftsddm vivg MTS sequence
Net charge of query sequence:           +3
Analyzed region:                        38
Number of basic residues in targeting sequence:    3
Number of acidic residues in targeting sequence:   0
Cleavage site:                          37
Cleaved sequence:
MLSVAARSGPFAPVLSATSRGVAGALRPLVQATVPA (SEQ ID NO: 38)

3'UTR sequence (Accession # CC310484; SEQ ID NO: 39)

```
gagacttgga ctcaagtcat aggctactt cagtcttat gtcacctcag gagacttatt    60
tgagaggaag cctctgtac ttgaagttga tttgaaatat gtaagaattg atgatgtatt   120
tgcaacatt aatgaaaat aaattgaatt taatgttgaa tactttcagg cattcactta   180
ataagacac tgttaagcac tgttatgctc agtcaaaaaa aaaaaaaaaa aaa          233
```

NADH-ubiquinone oxidoreductase 51 kDa subunit, mitochondrial precursor (Complex I-51KD) (CI-51KD) (NADH dehydrogenase flavoprotein 1); NDUFV1
Accession number: P49821

Protein Sequence: 464 aa (SEQ ID NO: 52)
mlatrrllgw slparvsvrf sgdltapkkt sfgslkdedr iftnlygrhd wrlkgslsrg
dwyktkeill kgpdwilgei ktsglrgrgg agfptgikws fmnkpsdgrp kylvvnadeg
epgtckdrei lrhdphklle gclvggramg araayiyirg efyneasnlq vaireayeag
ligknacgsg ydfdvfvvrg agayicgeet aliesiegkq gkprlkppfp advgvfgcpt
tvanvetvav spticrrggt wfagfgrem sgtklfnisg hvnhpctvee emsvplkell
ekhaggvlgg wdnllavipg gsstplipks vcetvlmdfd alvqaqtglg taavivmdrs
tdivkaiarl iafykhescg qctpcregvd wmnkvmarfv rgdarpaeid slweiskqie
ghtlcalgdg aawpvqglir hfrpeleerm qrfaqqhqar qaas

Séquence MTS
Net charge of query sequence:              +5
Analyzed region:                           38
Number of basic residues in targeting sequence:   7
Number of acidic residues in targeting sequence:  1
Cleavage site:                             21
Cleaved sequence: MLATRRLLGWSLPARVSVRF (SEQ ID NO: 40)

3'UTR sequence (Accession # CR041510; SEQ ID NO: 41)
cccccaccc tggctgctg tcctgcgtct atccatgtcq aatgctggac aataaagcga    60
gtgctgccca ccctccaaaa aaaaaaaaaa aaaaaaaaaa aa                     102

FIGURE 11 E

NADH dehydrogenase (ubiquinone) flavoprotein 2, 24kDa: NDUFV2
Accession number: NP_066552

Protein Sequence: 249 aa (SEQ ID NO: 53)
mffsaalrar aagltahwgr hvrnlhktam qngaggalfv hrdtpennpd tpfdftpeny
krieaivkny peghkaaavl pvldlaqrqn gwlpisamnk vaevlqvppm rvyevatfyt
mynrkpvgky hiqvctttpc mlmsdsile aiqkklgikv gettpdklft lievecgac
vnapmvqind nyyedltakd ieeiidelka gkipkpgprs grfscepagg llslteppkg
pgfgvqagl MTS sequence
Net charge of query sequence: +2
Analyzed region: 42
Number of basic residues in targeting sequence: 6
Number of acidic residues in targeting sequence: 0
Cleavage site: 44
Cleaved sequence:
MFFSAALRARAAGLTAHWGRHVRNLHKTAMQNGAGGALFVHRD (SEQ ID NO: 42)

3'UTR sequence (Accession # CC385433; SEQ ID NO: 43)
tttatattga actgtaaata tgtcactaga gaataaaat atggactcc aatctacgta    60
aaaaaaaaaa aaaaaaaaaa aaaaaaaaaa aaaaaaa                           97

FIGURE 11 F

Mitochondrial aldehyde dehydrogenase 2 precursor (ALDH2)
Accession number: NP_000681

Protein sequence: 517 aa (SEQ ID NO: 54)
mlraaarfgp rgrrllsaa atqavpapnq qpevfcnqif innewhdavs rktfptvnps
tgevicqvae gdkedvdkav kaaraafqlg spwrrmdash rgrlinrlad llerdrtyla
aletldngkp yvisylvdld mvlkclryya gwadkyhgkt ipidgdffsy trhepvgvcg
qiipwnfpll mqawklgpal atgnvvvmkv aeqtpltaly vanlikeagf ppgvvnivpg
fgptagaaia shedvdkvaf tgsteigrvi qvaagssnlk rvtlelggks pniimsdadm
dwaveqahfa lffnqgqccc agsrtfvqed iydefversv araksrvvgn pfdsktreqgp
qvdetqfkki lgyintgkqe gakllcgggi aadrgyfiqp tvfgdvqdgm tiakeeifgp
vmqilkfkti eevvgranns tyglaaavft kdldkanyls qalqagtvwv ncydvfgaqs
pfggykmsgs grelgeygiq aytevktvtv kvpqkns MTS sequence
Net charge of query sequence:       -1
Analyzed region:                    32
Number of basic residues in targeting sequence:    5
Number of acidic residues in targeting sequence:   0
Cleavage site:                      25
Cleaved sequence: MLRAAARFGPRLGRRLLSAAATQA (SEQ ID NO: 44)

3'UTR sequence (Accession # CC369460; SEQ ID NO: 45)

FIGURE 11G

Heme A:farnesyltransferase (COX10)
Accession number: NP_001294

Protein sequence: 443 aa (SEQ ID NO: 55)
maasphtlss rlltgcvggs vvylemtlq dsphkflhll rnvnkqwitf qhfsflkrny
vtqlwshnq qvrpkpepva apflektssg qskaelyemr plsppslsls rkpnekelle
lepdsvieds idvgketkee krwkemklqv ydlpgllarl sklkltalvv sttaagfala
pgpldwpcfl ltsvgtglas caansinqff evpldsnmnr tknrplvrgq lspllavsfa
tccavpgvai lllgvnpltg alglfnltly tccytplkri slantwvgav vgaslppvmgw
taatgsldag aflggllys wqfphfnals wglredysrg gycmmsvlhp glcnvalrh
clalvlsaa apvldittwt fpimalplna ylsylgfrfy vdladrrasrr lffcslwhlp
llllrnltck rpsgggdagp pps MTS sequence
Net charge of query sequence:         +15
Analyzed region:                      24
Number of basic residues in targeting sequence:    1
Number of acidic residues in targeting sequence:   0
Cleavage site:                        21
Cleaved sequence: MAASPHTLSSRLLTGCVGGS (SEQ ID NO: 46)

3'UTR sequence (Accession # CC352261; SEQ ID NO: 59)

FIGURE 11 H

Adenylate Kinase 2 (AK2)
Accession number: P54819

Protein sequence: 239 aa (SEQ ID NO: 56)
mapsvpaaep eypkgiravl lgppgagkgt qapriaenfc vchlatgdml ramvasgsel
gkklkatmda gklvsdemvv elieknletp lckngfildg fprtvrqaem lddmekrke
kldsviefsi pdsllirrit grlihpksgr syheefnppk epmkdditge plirrsddne
kalkirlqay htqttplley yrkrgihsai dasqtpdvvf asllaafska tckdlvmfi

MTS sequence
Net charge of query sequence:           +1
Analyzed region:                         8
Number of basic residues in targeting sequence:   0
Number of acidic residues in targeting sequence:  0
Cleavage site:
Cleaved sequence:

3'UTR sequence (Accession # CC221872; SEQ ID NO: 57)

```
tatcagaagg ccaggcgaga ctgcaacact gctcatcacc cgcggagtg atccctgctc    60
ttaggtgctg ggcagaggg aagggtggtc agatgagga tggtgaggga ggctggtga   120
gggctcaga ggaatacttg gaacaatagc agtgttattg tagtgtggca gtttctttca   180
tacataggtg agagttttca aagtgtaagg gaaaattaa ttttttaaaa aacaccatgc   240
ttggaggtg ggggtagaaa taggacaat attatttcta aggaatcggg ttttcattca   300
ctatggactg gtgaaatat tttttaaagc cagtgctcta agacctcagc tttatatcca   360
gaaccctatg ggttccagac caagagtaca ggaaatcaaa ttgttgtcct gtctgtctat   420
agcttggaac agggagcttt gattactgac tccggttcca cacactgtaa gatcaaaaac   480
catctcaca tttgaaagag atgtaaggtc tattcatagg gatggtggct caacaaatca   540
agcaaactgg aatcaagggg agggagaagg gaatgaaatg gaaagggagg ctgattcctt   600
tcccctgact taccactaat tactaggct acctactttc atgagtaacc tctcaacagcr   660
acccagacca tgccacaatc ctatgctctt gcttctttt atctgcactg tgtgaaggaa   720
ctctttttaa taatgagca agtgtcctaa gctctgtcat ccaagattg tccttttccac   780
tctcaaacc tgtgactggg ataactcaac agcactgtga tgtattattt tcaatgagyt   840
gccttctaaa actgaccaaa tgctgccttg ttggccct aaatcaataa aatatgttaa   900
aattgaaaa aaaaaaaaaa aa                                              922
```

FIGURE 11J

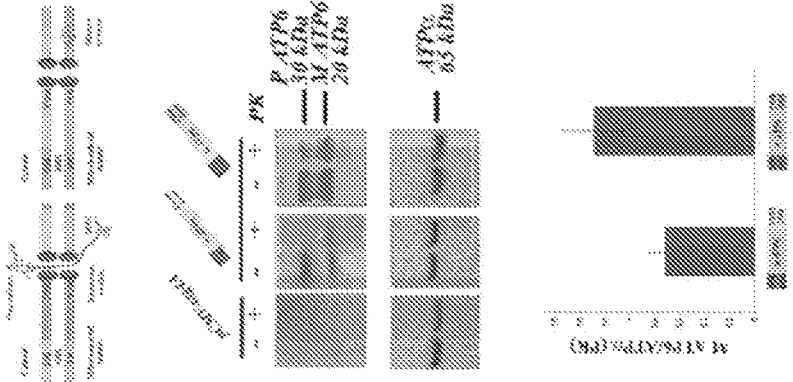
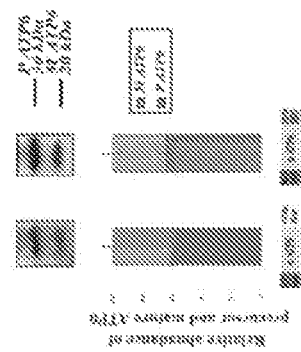
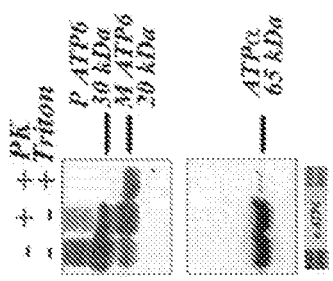
Figure 14A
Figure 14B
Figure 14C

IMPORTATION OF MITOCHONDRIAL PROTEIN BY AN ENHANCED ALLOTOPIC APPROACH

CROSS-REFERENCE TO RELATED APPLICATIONS

This application is a continuation of application Ser. No. 16/574,685, filed Sep. 18, 2019, which is a division of application Ser. No. 15/914,566, filed Mar. 7, 2018, which is a continuation of application Ser. No. 14/676,846, filed Apr. 2, 2015, which is a division of application Ser. No. 14/323,393, filed Jul. 3, 2014, which is a division of application Ser. No. 11/913,618, filed Jun. 5, 2008, which issued as now U.S. Pat. No. 9,017,999 and is a national stage entry of International Application No. PCT/EP2006/005323, filed May 2, 2006, which claims the benefit of U.S. Provisional Application No. 60/676,933 filed May 3, 2005. The contents of each of these applications is herein incorporated by reference.

FIELD OF THE INVENTION

The present invention relates to the field of cell biology, molecular genetics, and medicine. It more particularly relates to the importation of proteins into the mitochondrion of animal and human cells.

BACKGROUND OF THE INVENTION

Mitochondria occupy a central position in the overall metabolism of eukaryotic cells; hence the oxidative phosphorylation (OXPHOS), the Krebs's cycle, the urea cycle, the heme biosynthesis and the fatty acid oxidation take place within the organelle. Recently, another major role for mitochondria in determining the cellular life span was established, as they are recognized to be a major early mediator in the apoptotic cascade. Mitochondria are also a major producer of reactive oxygen species (ROS) causing oxidative stress and therefore inducers of cell death.

Primary defects in mitochondrial function are implicated in over 120 diseases and the list continues to grow, they encompass an extraordinary assemblage of clinical problems, commonly involving tissues that have high energy requirements, such as retina, heart, muscle, kidney, pancreas and liver. Their incidence is estimated of 1 in 5,000 live births. Indeed, combining epidemiological data on childhood and adult mitochondrial diseases suggests this prevalence as minimum, and could be much higher. Therefore, mitochondrial pathologies are considered among the most common genetically determined diseases, and are a major health issue since they remain inaccessible to both curative and palliative therapies.

Mitochondrion is assembled with proteins encoded by genes distributed between mitochondrial and nuclear genomes. These genes include those encoding the structural proteins of the respiratory chain complexes I-V, their associated substrates and products, the proteins necessary for mitochondrial biogenesis, the apparatus to import cytoplasmically synthesized precursors and the proteins necessary for mitochondrial assembly and turnover. Studies leading to the identification of genes involved in mitochondrial disorders have made considerable progress in the last decade. Indeed, numerous mutations in both mitochondrial DNA and a number of nuclear genes have been reported in association with a striking diversity of clinical presentations.

Approximately half of human mitochondrial disorders are caused by pathogenic point mutations of mtDNA, one-third of which are located in coding genes. There is currently no treatment for any of these disorders, a possible therapeutic approach is to introduce in the nucleus a wild-type copy of the gene mutated in the mitochondrial genome and import normal copies of the gene product into mitochondria from the cytosol. This approach has been termed "allotopic expression".

There have already some reports describing that engineered nucleus-localized version of some mtDNA genes could be expressed in mammalian cells. For example, in a Leigh's disease case, a plasmid was constructed in which the mitochondrial targeting signal of the nuclear encoded COX8 gene was appended to a recoded mitochondrial ATP6 gene, mutated in patients. Stably transfected cells from patients present an improvement of growth in galactose medium and a mild increase in ATP synthesis, however the amount of Atp6 protein imported into mitochondria was relatively low (18.5%), implying that the precursor was not imported efficiently (Manfredi, G., et al., Rescue of a deficiency in ATP synthesis by transfer of MTATP6, a mitochondrial DNA-encoded gene to the nucleus. Nature Genet., 2002. 30: p. 394-399).

Oco-Cassio and co-workers have demonstrated that allotopic expression of apocytochrome b and ND4 into Cos-7 and HeLa cells, did not lead to an efficient mitochondrial import of these proteins (Oca-Cossio, J., et al., Limitations of allotopic expression of mitochondrial genes in mammalian cells. Genetics, 2003. 165: p. 707-720).

Hence, up today important limitations are found to the allotopic expression as a therapeutic approach and require optimization to overcome the significant hurdles before it can be applied in genetic therapy.

One hypothesis that can explain the poor import ability of the mitochondrial protein is its high hydrophobicity. Thus, the precursor synthesized in the cytoplasm remains stuck on the outer mitochondrial membrane.

Mitochondria assembly depends on balanced synthesis of 13 proteins encoded by mtDNA with more than a thousand others encoded by nuclear DNA. As the vast majority of mitochondrial polypeptides are synthesized in the cytoplasm, there is the requirement for an efficient and specific protein targeting system. This process involves the transport of mRNAs from the nucleus to the surface of mitochondria.

The inventors examined the possibility that allotopic expression of DNA such as mtDNA could be optimized by a targeted localization of the mRNA to the mitochondrial surface.

SUMMARY OF THE INVENTION

Mitochondrial proteins are encoded by nucleic acids which are located in the mitochondrion, i.e. mitochondrial nucleic acids (mtDNA, mtRNA), as well as by nucleic acids which originate from the nucleus, i.e. nuclear nucleic acids (nDNA, nRNA).

The inventors describe an enhanced allotopic approach for importation of proteins into the mitochondrion. The present invention provides means, including compositions and methods, which enable mitochondrial importation at enhanced efficiency and stability compared to prior art techniques. The means of the invention enable a targeted localization of the mRNA to the mitochondrial surface.

Compared to prior art techniques, the means of the invention enable the efficient and stable importation of protein into the mitochondrion of an animal of human in need thereof, such as an animal or human having a cellular dysfunction caused by one or several mutations in a gene encoding a mitochondrial protein.

The inventors demonstrate that mRNA sorting to the mitochondrial surface is an efficient way to proceed to such an allotopic expression, and that this mRNA sorting can be controlled by selecting appropriate mitochondrion-targeting sequence (MTS) and appropriate 3'UTR sequences. The CDS sequence which codes for the protein to be delivered into the mitochondrion is guided by these appropriate MTS and 3'UTR sequences from the nuclear compartment to the mitochondrion-bound polysomes (where the CDS is translated), and aids in an efficient translocation of a mature functional protein into the mitochondria.

The inventors demonstrate that, to obtain a stable therapeutically-effective importation, both an appropriate MTS and an appropriate 3'UTR should preferably be used.

Appropriate MTS and 3'UTR sequences correspond to those of nuclearly-transcribed mitochondrially-targeted mRNAs. If a vector is used, it is preferred that it does not contain any 3'UTR which would correspond to the 3'UTR of a nuclearly-transcribed but not-mitochondrially-targeted mRNAs. To the best of the inventors' knowledge, all commercially-available vectors contain such a not-mitochondrially-targeted mRNA; it is then preferred to delete this inappropriate 3'UTR from the vector before use as mitochondrial importer.

The means of the invention are especially adapted to animal and human cells, and more particularly to mammalian cells. They give access to therapeutically-effective means for such cells.

BRIEF DESCRIPTION OF THE DRAWINGS

FIGS. 1A and 1B: Map and sequence of COX10 MTS-nATP6, SOD2MTS-nATP6, COX10 MTS-nATP6-COX10 3'UTR, SOD2MTS-nATP6-SOD2 3'UTR obtained in the pCMV-Tag 4A vector.

FIG. 1A. The four constructs are schematically represented.

FIG. 1B. The COX10 MTS-nATP6 and SOD2MTS-nATP6 are introduced at the EcoRI restriction site of the pCMV-tag4A vector. EcoRI restriction sites are framed. The ATG of SOD2 MTS, COX10 MTS and nATP6, are bold and underlined. The COX10 3'UTR and the SOD2 3'UTR are inserted at the PvuI and MluI restriction sites, represented in bold. FLAG tag epitope is in italics.

1: Transiently transfected cells with the COX10 MTS-nATP6 vector (SV40 3'UTR).
2: Transiently transfected cells with COX10 MTS-nATP6-COX10 3'UTR vector.
In 3 and 4 we examined RNAs from the same transfection experiment but in this case it represents the stably transfected cells.
5: HeLa transfected cells with the empty pCMV-tag4A vector.
6: Hela cells.

Specific oligonucleotide primers were used to detect hybrid ATP6 mRNA in transfected cells, for the MTS COX10-ATP6 product MTS COX10 and ATP6 ORF 3' were used (cf. Table 2 below, in example 1). For the amplification of the complete ATP6 ORF and the entire COX10 3'UTR the ATP6 ORF 5' primer and the 3' UTR COX10 3' Primer were used (cf. Table 2 below, in example 1). As internal control, the steady-state levels of COX6c mRNA were examined in all the RNA preparations using both COX6 primers shown in said Table 2.

Figure 3:
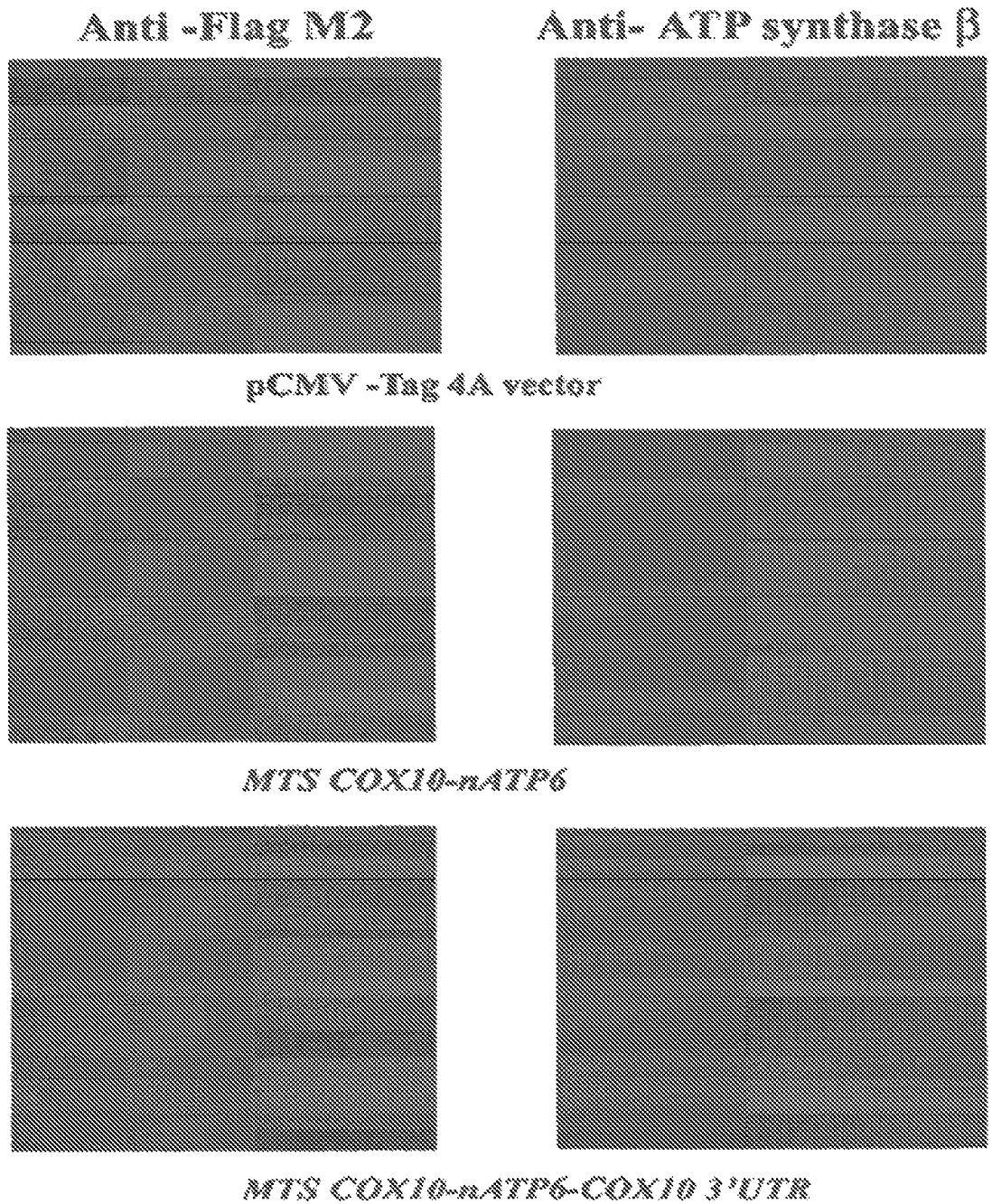

FIG. 3: Subcellular localization of the recoded Atp6 protein in HeLa cells

Stably transfected cells with either COX10 MTS-nATP6 (SV40 3'UTR) or COX10 MTS-nATP6-COX10 3'UTFR vector were visualized by indirect immunofluorescence using antibodies to Flag and ATP synthase subunit beta. The punctuate pattern of Flag antibody staining indicates that the fusion Atp6 protein is efficiently transported to mitochondria in vivo, since the same pattern of mitochondria labeling was observed with the beta subunit of ATP synthase.

FIGS. 4A and 45: nATP6 proteins are efficiently imported Into mitochondria in vivo.

FIG. 4A: Proteins were extracted from HeLa cells and HeLa transfected cells (COX10 MTS-nATP6-SV40 3'UTR or COX10 MTS-nATP6-COX10 3'UTR vectors) and assayed for import in the absence and presence of proteinase K (PK). Proteins were treated with 200 μg/ml of proteinase K at 0° C. for 30 min. Then, they were separated on 4-12% polyacrylamide SDS gel and transferred into a nitrocellulose membrane. The resulting blot was probed with mouse monoclonal anti-ATP synthase subunit alpha or mouse monoclonal anti-Flag M2 antibodies.

FIG. 4B: Histograms of the amount of COX11 MTS-nATP6-Flag and Alp synthase subunit alpha with or without proteinase K. Signals from immunoblots were scanned and quantified by the MultiAnalyst System (Bio-Rad). The amount of the mature ATP6 protein insensitive to proteinase K proteolysis is approximately 185% higher in cells transfected with COX10 MTS-nATP6-COX10 3'UTR vector compared to cells expressing the COX10 MTS-nATP6 without COX10 3'UTR but with the SV40 Poly A signal. Besides, the amount of the mature form of the recoded ATP6 protein inside mitochondria is very similar to the one measured for the naturally imported ATP synthase subunit alpha, confirming that recoded ATP6 proteins are efficiently translocated into the organelle.

Figure 5A:
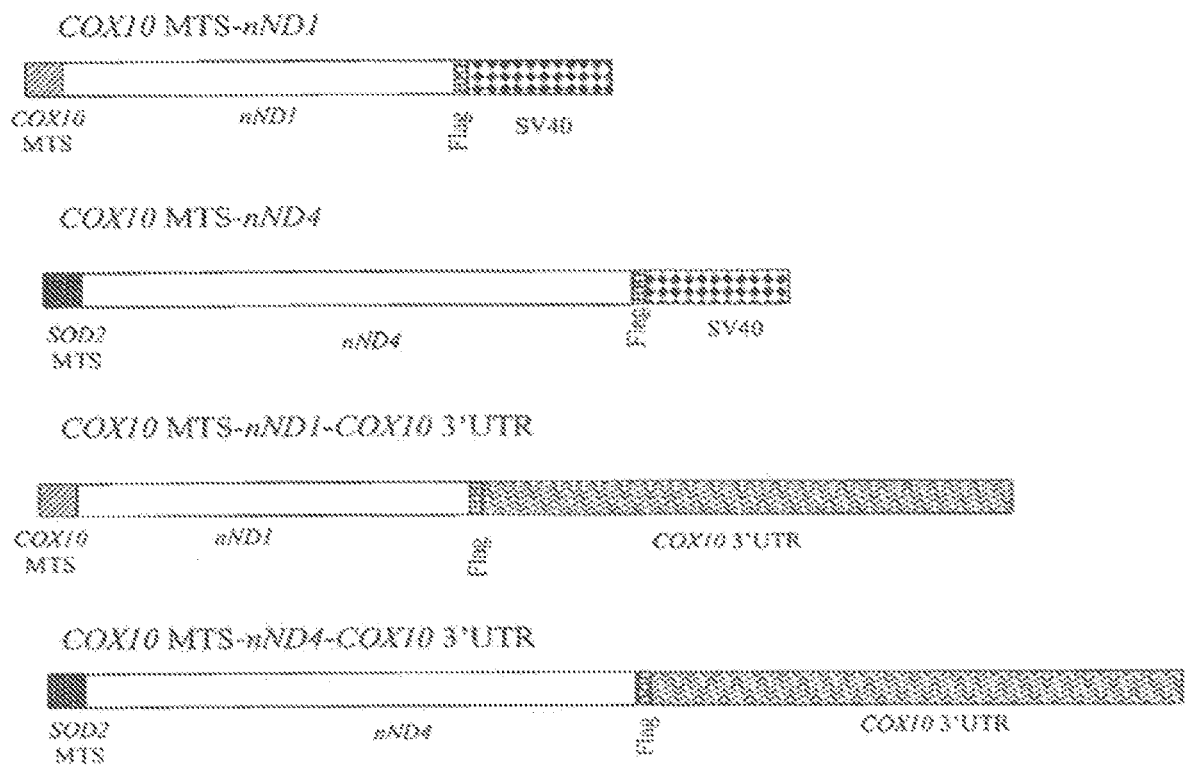

FIGS. 5A and 5B: Map and sequence of COX10 MTS-nND1, COX10MTS-nND4, COX10 MTS-nND1-COX10 3'UTR, COX10MTS-nND4-COX10 3'UTR obtained in the pCMV-Tag 4A vector.

FIG. 5A. The four constructs are schematically represented.

FIG. 5B. The COX10 MTS-nND1 and COX10MTS-nND4 are introduced at the XhoI/SalI restriction sites of the pCMV-tag4A vector. XhoI and SalI restriction sites are framed. The ATG of COX10 MTS, nND1 and nND4, are bold and underlined. The COX10 3'UTR is inserted at the PvuI and MluI restriction sites, represented in bold. FLAG tag is in italics.

Figure 6:
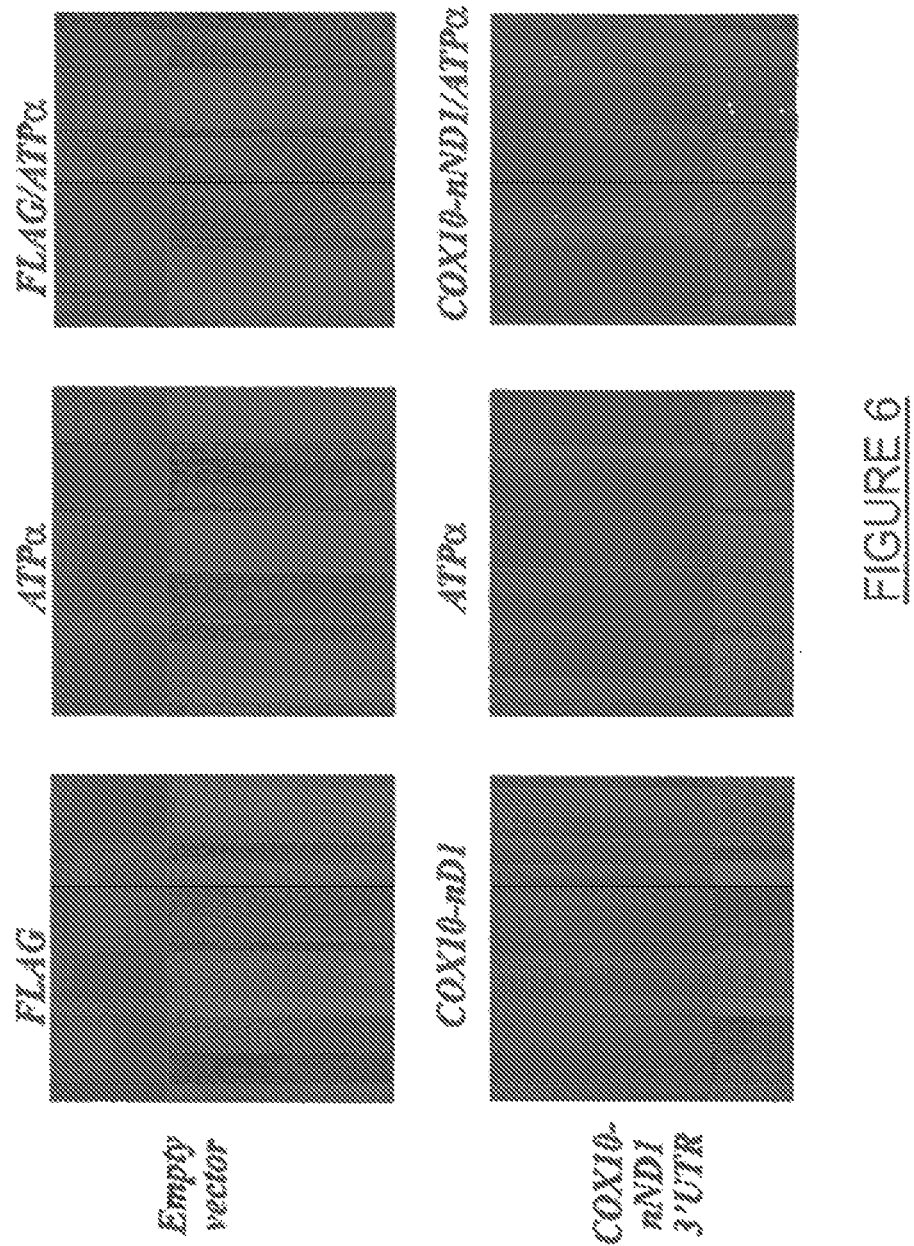

FIG. 6: Immunocytochemistry of G3460A LHON fibroblats

The fusion protein was visualized by indirect immunofluorescence using antibodies to Flag. Indicative of mitochondrial import, cells transfected with either COX10 MTS-nND1-SV40 3'UTR or COX10 MTS-nND1-COX10 3'UTR vectors exhibited a typically punctuate staining pattern, also observed with the beta subunit of ATP synthase, which localize in vivo to the inner mitochondrial membrane. In contrast, cells transfected with the empty pCMV-Tag 4A vector exhibited a very low intensity and diffuse cytoplasmic staining when antibodies to Flag were used.

Figure 7:
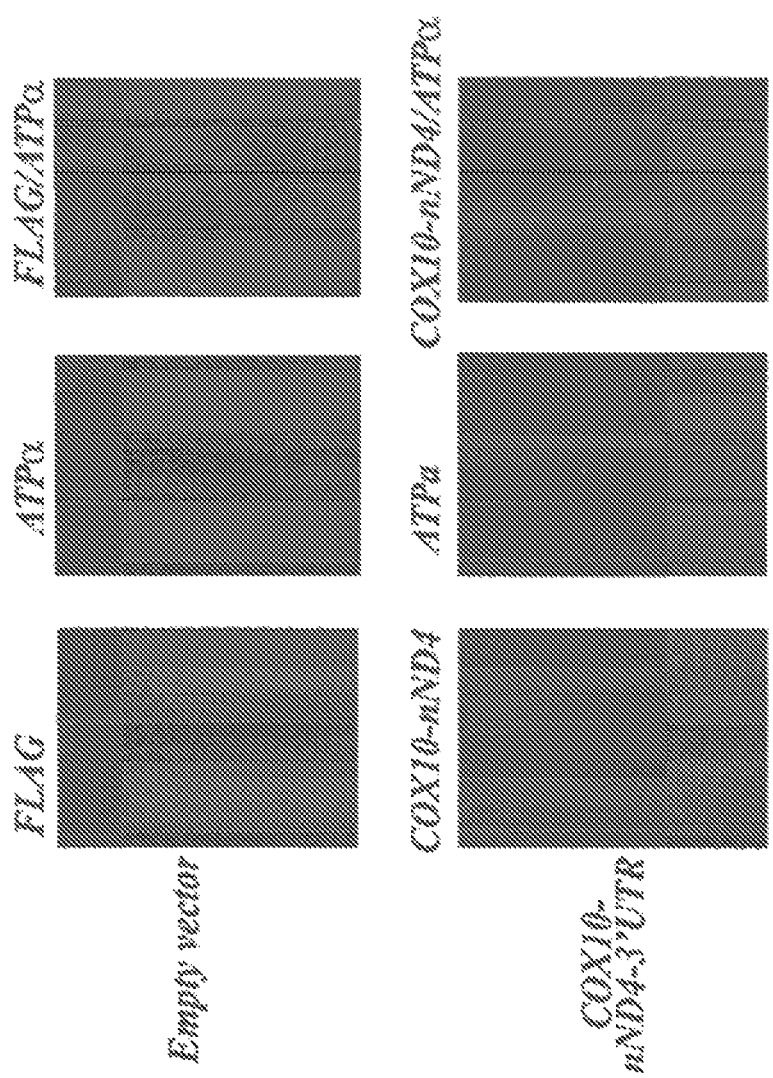

FIG. 7: Immunocytochemistry of G11778A LHON fibroblasts

The fusion protein was visualized by indirect immunofluorescence using antibodies to Flag. Cells transfected with either COX10 MTS-nND4-SV40 3'UTR or COX10 MTS-nND4-COX10 3'UTR vectors exhibited a typically punctate staining pattern, also observed with the beta subunit of ATP synthase, which localize in vivo to the inner mitochondrial membrane. This data indicates that ND4 is efficiently imported into mitochondria. In contrast, cells transfected with the empty pCMV-Tag 4A vector exhibited a very low intensity and diffuse cytoplasmic staining when antibodies to Flag were used.

Figure 8:
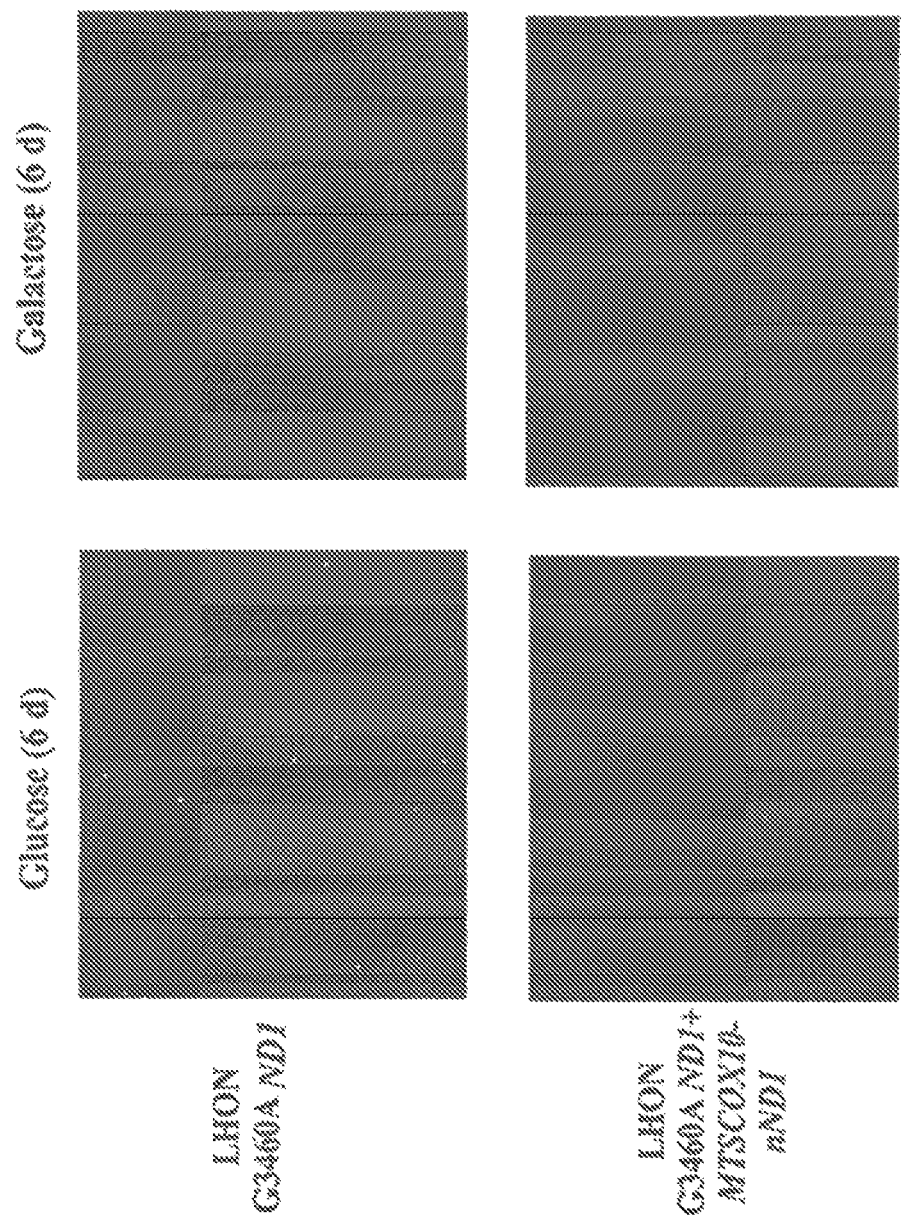

FIG. 8: Growth in glucose-free medium of non-transfected fibroblasts with the G3460A mutation and transfected fibroblasts with the MTS COX10-nND1-COX10 3'UTR vector Fibroblasts from LHON patients presenting the G3460A mutation were stably transfected with the MTS COX10-nND1-COX10 3'UTR vector and examined for their ability to growth on DMEM medium supplemented with 10 mM galactose. Non-transfected fibroblasts (LHON G3460A ND1) show a severe growth defect on galactose medium, the ability to grow on galactose was significantly improved when the recoded nND1 protein is expressed in stably transfected cells (LHON G3460A ND1+MTSCOX10-nND1). Cells were photographed after 6 day culture.

FIG. 9: recoded CDS of mtDNA (SEQ ID NO: 27-29)

FIG. 9 shows the human nucleic acid coding sequence of the mitochondrial ATP6, ND1, ND4, recoded according to the universal genetic code (nATP6, nND1, nND4 of SEQ ID NO:27, 28 and 29, respectively). The recoded ND1 and ND4 which are shown in FIG. 9 also take into account the preferred human codon usage (see example 2 below).

FIG. 10: Illustrative human co-translational MTS and 3'UTR (SEQ ID NOS: 30, 47, 31, 60)

FIG. 10 shows the sequence of human COX10 MTS (SEQ ID NO: 30), human COX10 3'UTR (SEQ ID NO: 47), human SOD2 MTS (SEQ ID NO: 31), and human SOD2 3'NTR (SEQ ID NO: 60).

TABLE 5

| | Nucleic acid MTS | Nucleic acid 3'UTR |
|---|---|---|
| COX10 | SEQ ID NO: 30 | SEQ ID NO: 47 |
| SOD2 | SEQ ID NO: 31 | SEQ ID NO: 60 |

FIGS. 11A-11I show the protein sequence coded by illustrative human mitochondrially-targeted mRNA, as well as their respective MTS peptide sequences and their respective 3'UTR sequences. ATCC accession number is indicated for each of these protein sequences.

ACO2=Aconitase;
SOD2=Mitochondrial Superoxide dismutase;
ATP5b=P synthase subunit beta;
UQCRFS1=Ubiquinol-cytochrome c reductase, Rieske iron-sulfur polypeptide 1;
NDUFV1=NADH-ubiquinone oxidoreductase 51 kDa subunit, mitochondrial
precursor (Complex I-51KD) (CI-51KD) (NADH dehydrogenase flavoprotein 1);
NDUFV2=NADH dehydrogenase (ubiquinone) flavoprotein 2, 24 kDa;
ALDH2=Mitochondrial aldehyde dehydrogenase 2 precursor;
COX10=Heme A:farnesyltransferase;
AK2=Adenylate Kinase 2.

SEQ ID NO are as follows:

TABLE 6

| | MTS peptide | 3'UTR | Protein |
|---|---|---|---|
| ACO2 | SEQ ID NO: 32 | SEQ ID NO: 33 | SEQ ID NO: 48 |
| SOD2 | SEQ ID NO: 34 | SEQ ID NO: 35 | SEQ ID NO: 49 |
| ATP5b | SEQ ID NO: 36 | SEQ ID NO: 37 | SEQ ID NO: 50 |
| UQCRFS1 | SEQ ID NO: 38 | SEQ ID NO: 39 | SEQ ID NO: 51 |
| NDUFV1 | SEQ ID NO: 40 | SEQ ID NO: 41 | SEQ ID NO: 52 |
| NDUFV2 | SEQ ID NO: 42 | SEQ ID NO: 43 | SEQ ID NO: 53 |
| ALDH2 | SEQ ID NO: 44 | SEQ ID NO: 45 | SEQ ID NO: 54 |
| COX10 | SEQ ID NO: 46 | SEQ ID NO: 59 | SEQ ID NO: 55 |
| AK2 | | SEQ ID NO: 57 | SEQ ID NO: 56 |

Figure 12A:
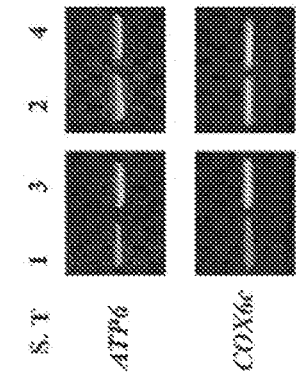
Figure 12C:
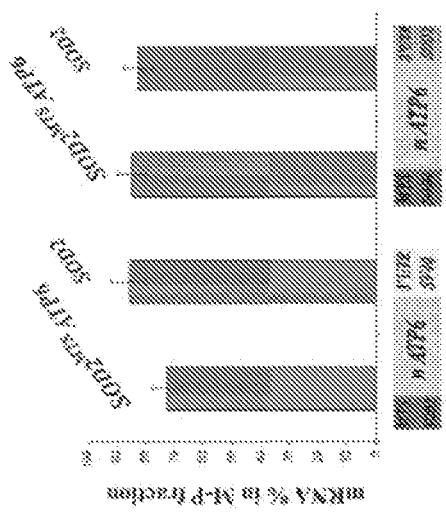
Figure 12B:
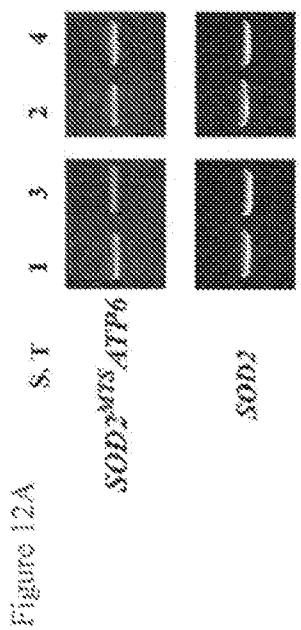

FIGS. 12A, 12B, 12C: Subcellular distribution of hybrid ATP6 mRNAs in HeLa cells A. Total RNAs extracted from cells expressing the SOD2$^{MTS}$ ATP6-3'UTR$^{SV40}$ (S.T 1 and S.T 2) or the SOD2$^{MTS}$ ATP&3'UTR$^{SOD2}$ (S.T 3 and S.T 4) vectors were subjected to RT-PCR analysis to reveal amounts of hybrid ATP6 (SOD2$^{MTS}$ ATP6) mRNAs and endogenous SOD2, ATP6 and COX6c mRNAs. The amount of RNAs used for the reverse transcription, PCR conditions and specific oligonucleotides used for each gene are summarized in Table 9.

B. RNAs were purified from mitochondrion-bound polysomes (M-P) and free-cytoplasmic polysomes (F-P) of stably transfected cell lines with either SOD2$^{MTS}$ ATP6-3'UTR$^{SV40}$ (S.T 1 and S.T 2) or SOD2$^{MTS}$ ATP6-3'UTR$^{SOD2}$ (S.T 3 and S.T 4) vectors and subjected to RT-PCR analysis. The abundance of endogenous ATP6, SOD2 and COX6c mRNAs was determined in each polysomal population using the conditions shown in Table 9.

C. Densitometric analyses were performed using the Quantity One Biorad software system.

The difference between the amounts of hybrid ATP6 mRNAs in cells expressing respectively SOD2$^{MTS}$ ATP6-3'UTR$^{SV40}$ or SOD2$^{MTS}$ ATP6-3'UTR$^{SOD2}$ constructions was significant according to the paired Student's t-test (P<0.0034, n=6).

Figure 13:
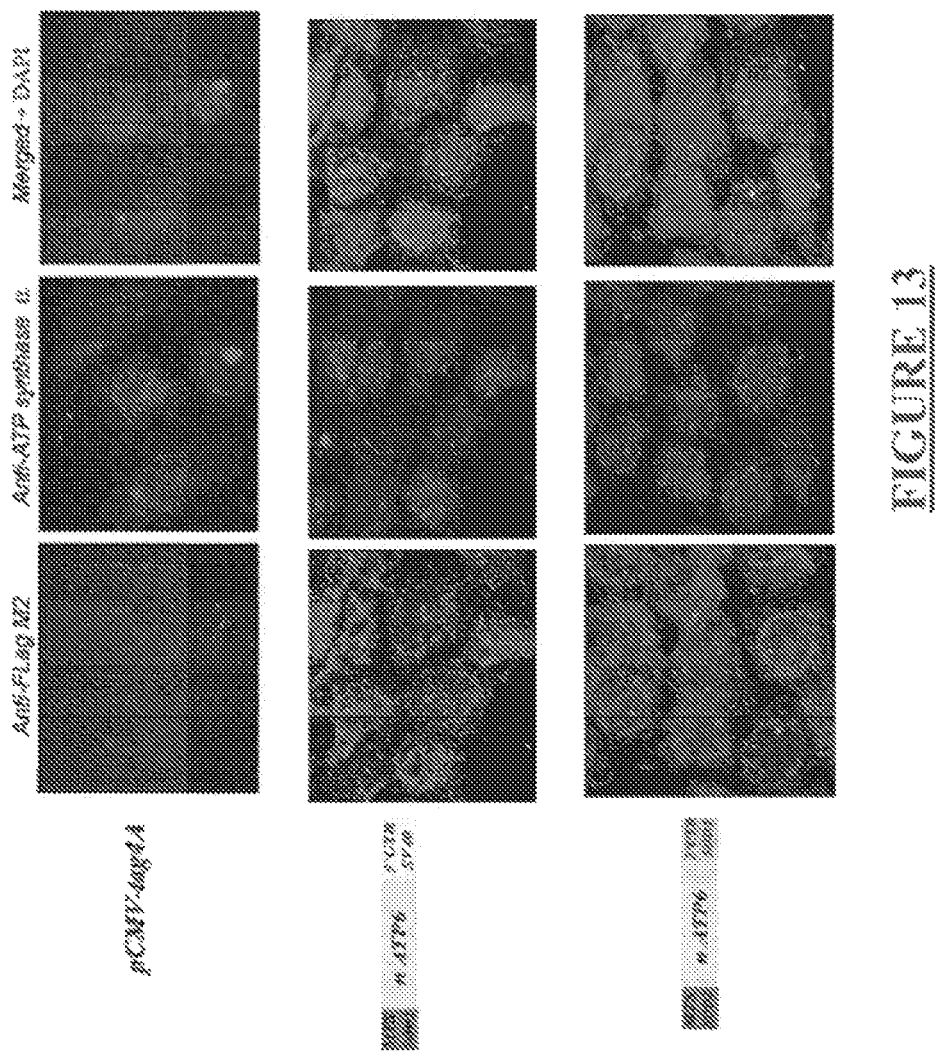

FIG. 13: Subcellular localization of the recoded Atp6 protein in vivo

Stably transfected cells with either the empty pCMV-tag4A vector, SOD2$^{MTS}$ ATP6-3'UTR$^{SV40}$ or SOD2$^{MTS}$ ATP6-3'UTR$^{SOD2}$ plasmids were visualized by indirect immunofluorescence using antibodies to Flag and ATP synthase subunit α. For each cell type visualized, a merged image in association with DAPI staining is shown at the right panel. Indicative of the mitochondrial localization of recoded ATP6 proteins, cells transfected with either SOD2$^{MTS}$ ATP6-3'UTR$^{SV40}$ or SOD2$^{MTS}$ ATP6-3'UTR$^{SOD2}$ plasmids showed a significant colocalization of both Flag and ATP synthase α signals. In contrast, cells transfected with the empty vector exhibited a low diffuse cytoplasmic staining.

FIGS. 14A, 14B, 14C: Recoded ATP6 proteins are efficiently imported Into mitochondria in vivo.

A. Six independent mitochondria purifications were performed with cells stably transfected with either SOD2$^{MTS}$ ATP6-3'UTR$^{SV40}$ or SOD2$^{MTS}$ ATP6-3'UTR$^{SOD2}$ plasmids and subjected to Western blot analysis. Signals for the ATP6 precursors and mature forms were scanned and quantified by the Quantity One System (Bio-Rad). No significant differences between the amounts of the precursor and the mature form of the recoded ATP6 proteins were observed in each cell line examined.

B. Upper panel: Schematic representation of mitochondrial import intermediates. The hydrophobic passenger protein can be trapped en route to the matrix. In this step, the protein can be blocked or represented an intermediate of translocation. This doesn't prevent the cleavage of the MTS by a mitochondrial processing peptidase, the rest of the protein remains accessible to PK digestion and therefore if digested it becomes undetectable in the Western blot assay. The fraction of the protein completely translocated turns into a mature protein insensitive to PK located in the inner mitochondrial membrane. MM: mitochondrial matrix; OM: outer membrane; MIS: mitochondrial intermembrane space, TOM: Translocase of the Outer Membrane, TIM: Translocase of the Inner membrane.

Middle panel: Mitochondria extracted from transfected cells with either the empty pCMV-Tag 4A vector, $SOD2^{MTS}$ ATP6-3'UTR$^{SV40}$ or $SOD2^{MTS}$ ATP6-3'UTR$^{SOD2}$ plasmids were subjected to Western blot essays. 20 µg of proteins were treated with 150 µg/ml of PK at 0'C for 30 minutes and subjected to immunoblotting analysis using anti-ATP synthase subunit α and anti-Flag M2 antibodies. Densitometric analyses of experiments performed with six independent mitochondrial purifications were represented at the lower panel. We normalized values measured for the signal of the mature form of ATP6 resistant to PK with ATPα signal revealed after PK digestion. We then compared the value obtained for cells expressing either the $SOD2^{MTS}$ ATP6-3'UTR$^{SV40}$ or the $SOD2^{MTS}$ ATP63'UTR$^{SOD2}$ plasmids. Signals from Western blots were scanned and quantified by the Quantity One System (Bio-Rad). The difference between the amounts of fully mitochondrial translocated ATP6 protein in cells expressing respectively $SOD2^{MTS}$ ATP6-3'UTR$^{SV40}$ or $SOD2^{MTS}$ ATP6-3'UTR$^{SOD2}$ constructions was significant according to the paired Student's t-test (P<0.0022, n=6).

C. 20 µg of mitochondria isolated from cells stably transfected with $SOD2^{MTS}$ ATP6-3'UTR$^{SOD2}$ vector treated with 150 µg/ml of PK and 1% Triton×100 at 0'C for 30 min and subsequently subjected to Western analysis.

Figure 15:
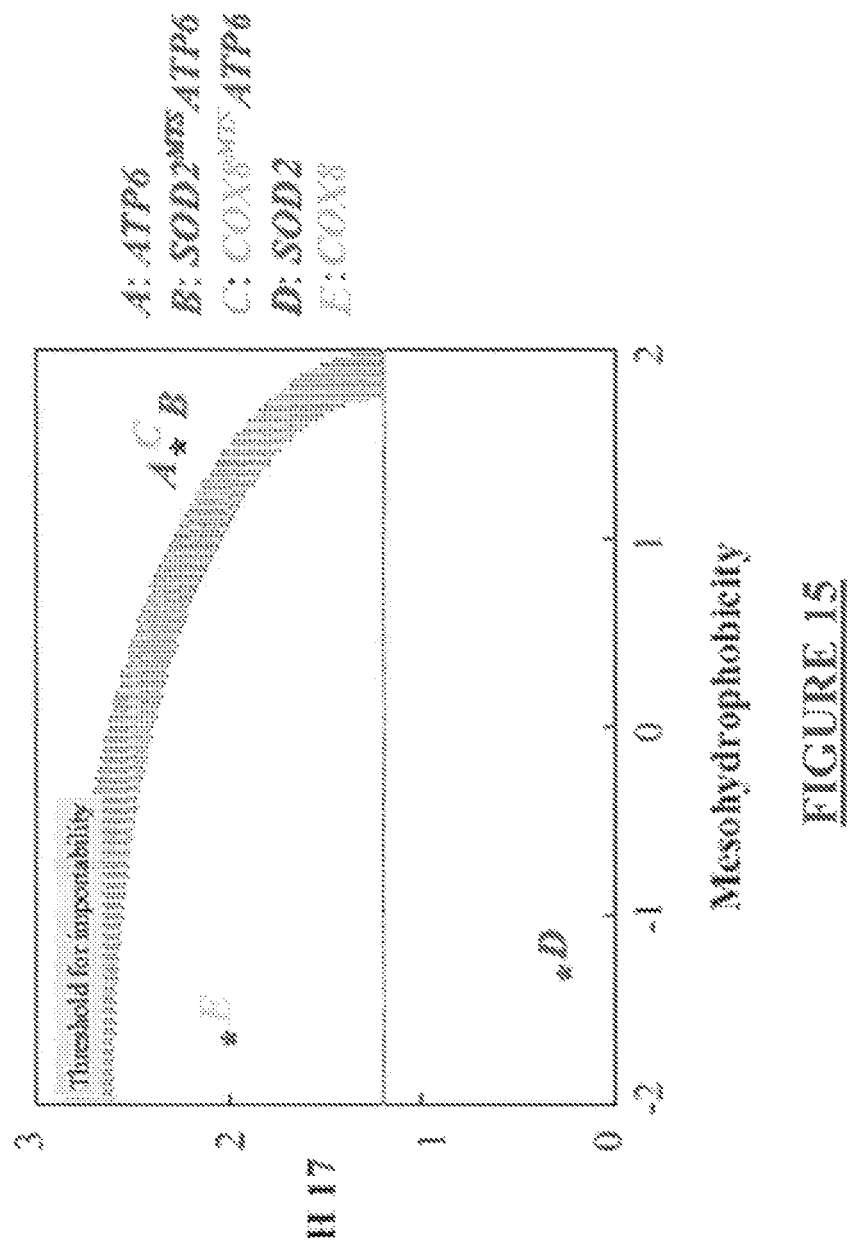

FIG. 15: Mitochondrial Import ability of ATP6 proteins based on the mesohydrophobicity index A plot developed by Claros and Vincens was used to measure mitochondrial import ability of fusion ATP6 proteins. By this approach, the fusion $SOD2^{MTS}$ ATP6 protein would not be importable. Mesohydrophobicity, which is the average regional hydrophobicity over a 69 amino acid region, was calculated using Mito-ProtII. Values obtained are the following: ATP6: 1.41; $SOD2^{MTS}$ ATP6: 1.41; $COX8^{MTS}$ ATP6: 1.41; SOD2: −1.26; COX8: −1.63.

Figure 16:
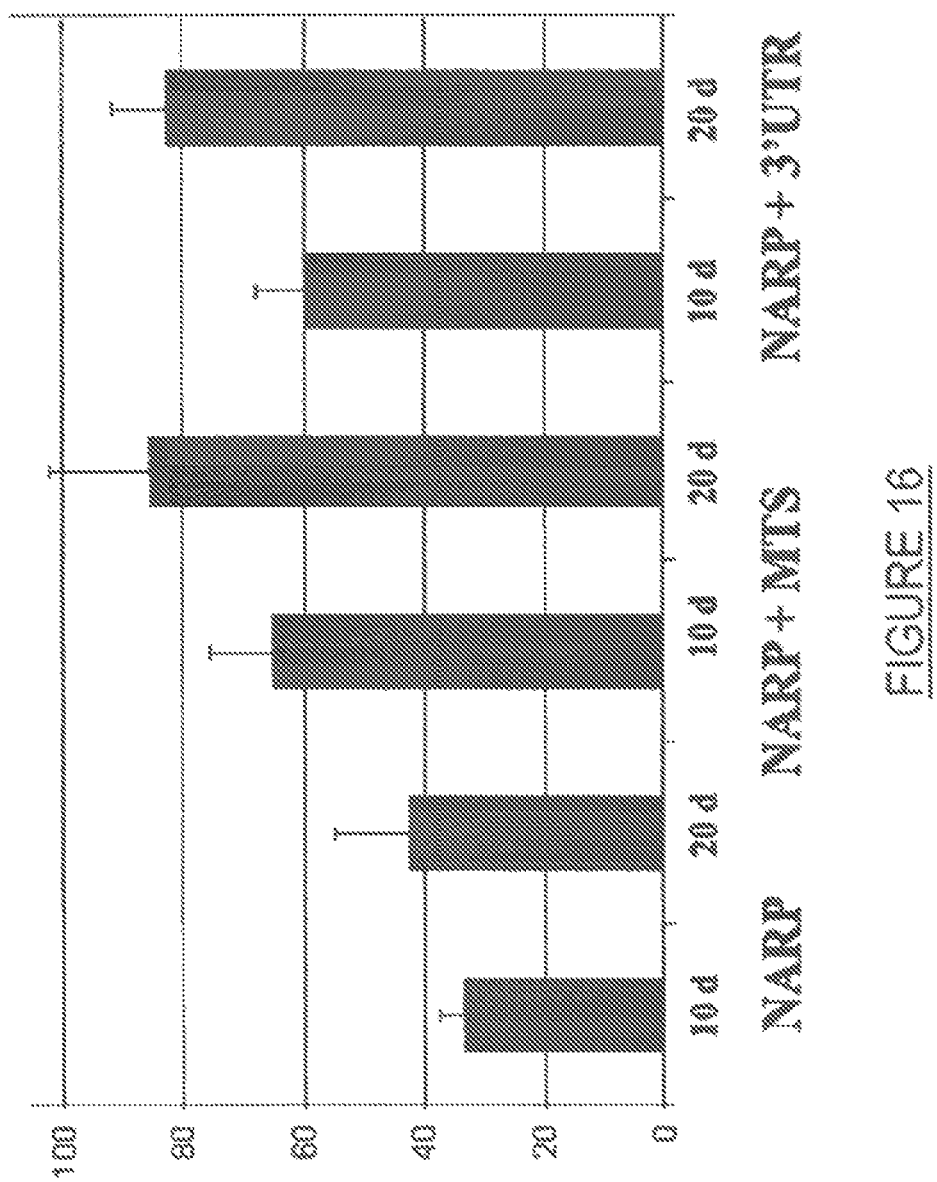

FIG. 16: rescue of NARP cells; survival rate on galactose medium of NARP cells (mutated ATP6), and of NARP cells transfected by a SOD2 MTS-ATP vector (SOD2 MTS-ATP6-SV40 3'UTR), or by a vector of the invention (SOD2 MTS-ATP6-SOD2 3'UTR); see also example 3, table 11.

Figure 17:
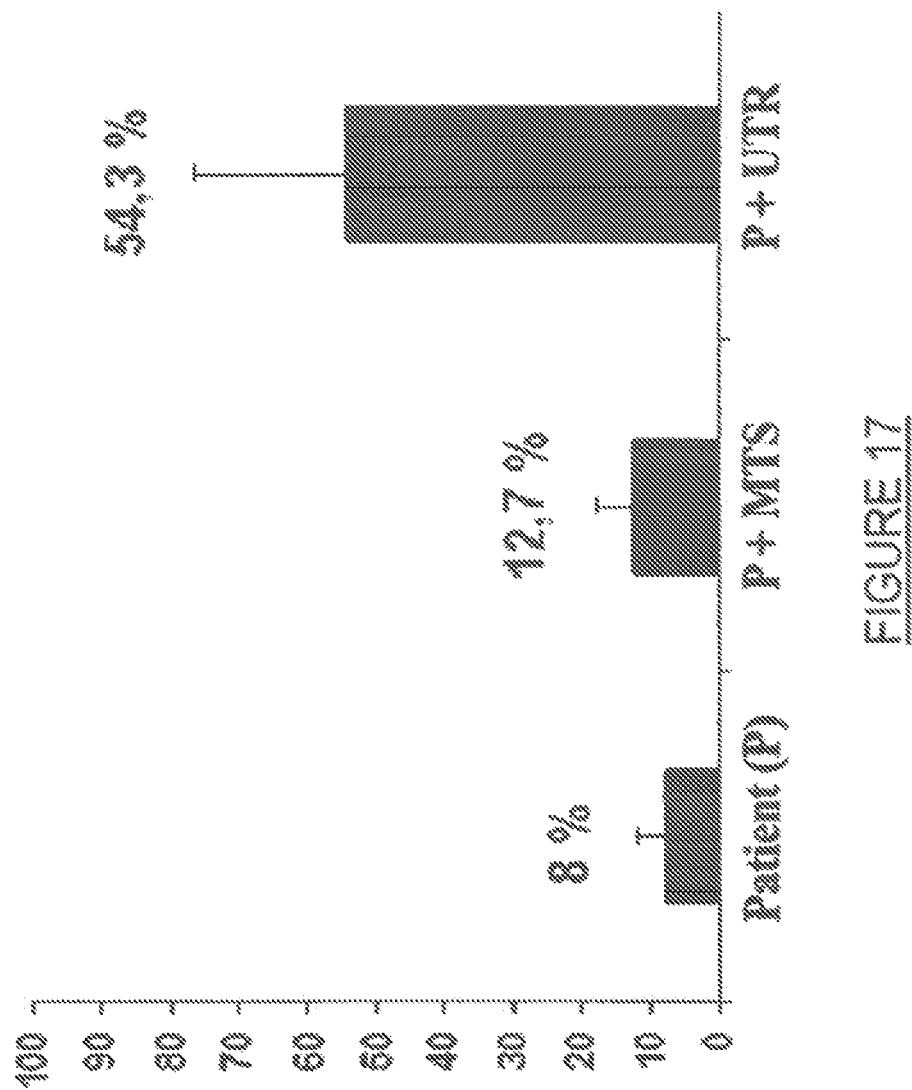

FIG. 17: rescue of LHON fibroblasts; survival rate on galactose medium of LHON fibroblasts (mutated ND1), and of LHON fibroblasts transfected by a COX10 MTS-ND1-SV40 3'UTR vector, or by a vector of the invention (COX10 MTS-ND1-COX10 3'UTR); see also example 4, table 12.

Figure 18:
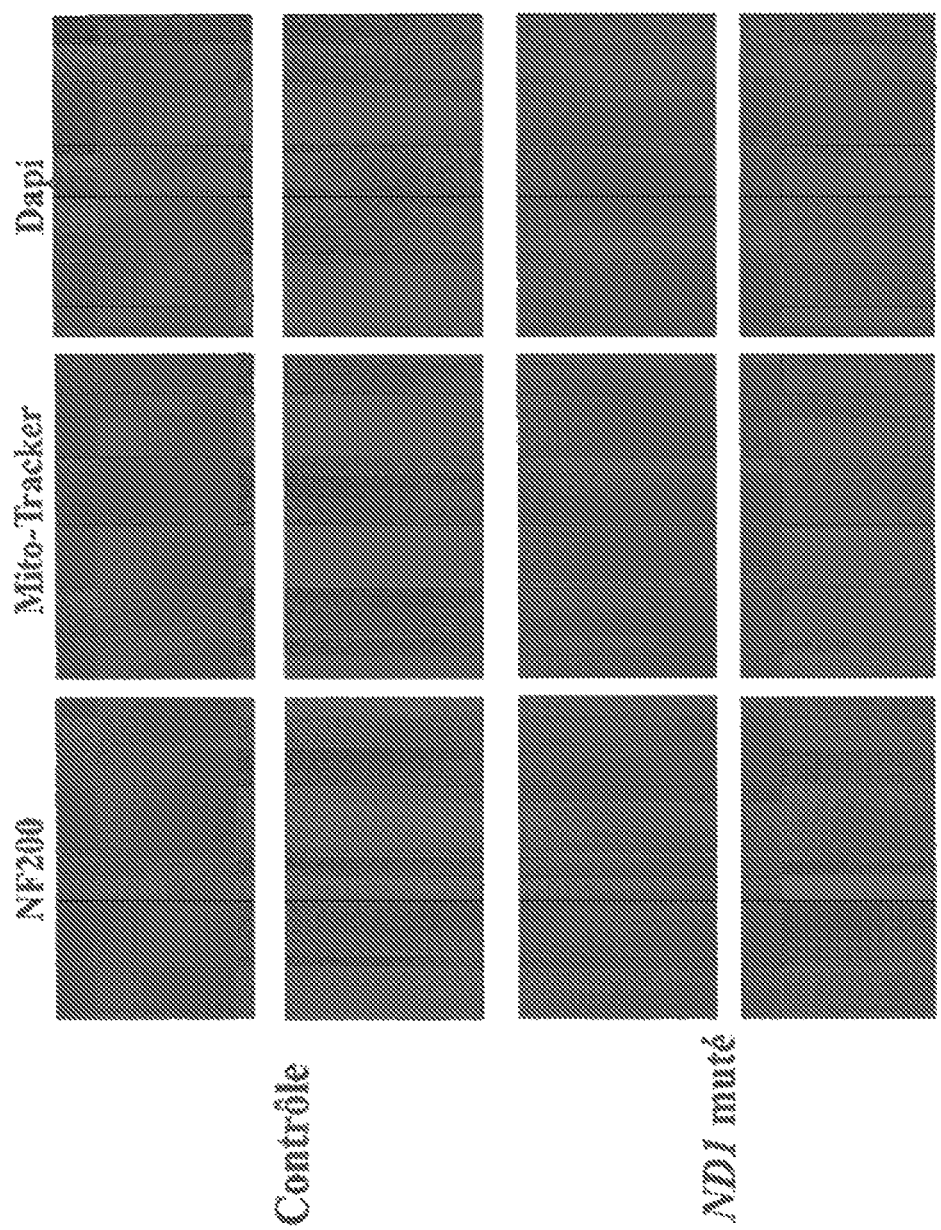

FIG. 18: mitochondrial distribution in retinal gangion cells (RGC) transfected with the mutated version of ND1.

Figure 19:
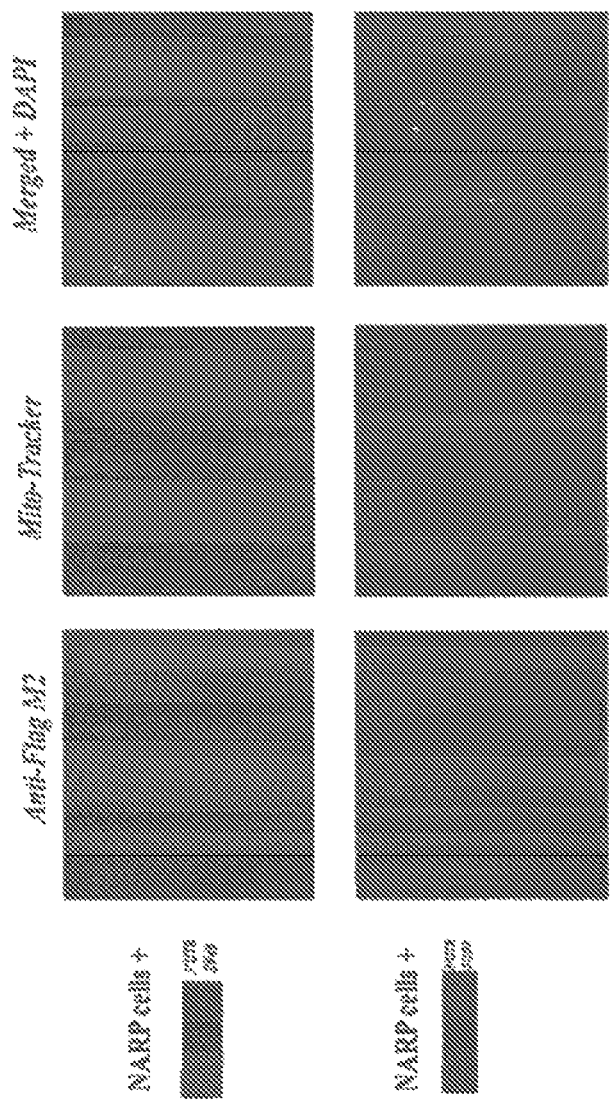

FIG. 19: rescue of NARP cells; anti-Flag, Mito-tracker and merged+DAPI staining of NARP cells transfected either with SOD2 MTS-ATP6-SV40 3' UTR, or with SOD2 MTS-ATP6-SOD2 3'UTR.

DETAILED DESCRIPTION OF THE INVENTION

The present invention relates to the use and control of mRNA sorting at the surface of mitochondria.

Schematically, the present invention relates to the use of nucleic acid sequences corresponding to a co-translational MTS and of a co-translational 3'UTR, for guiding a desired mRNA (which codes a desired mitochondrial protein) from the nucleus to the mitochondria-bound polysomes, and for inducing the effective translocation of the translated protein into the mitochondrion.

By "co-translational", it is herein referred to a nuclearly-encoded mitochondrially-targeted pathway.

Mitochondrion-Targeting Sequences (MTS):

Sequences known as mitochondrion-targeting signal or mitochondrial targeting signal are referred to as MTS by the skilled person.

A MTS sequence can be identified within a protein or nucleic acid sequence by a person of ordinary skill in the art.

Most mitochondrion-targeting peptides consist of a N-terminal pre-sequence of about 15 to 100 residues, preferably of about 20 to 80 residues. They are enriched in arginine, leucine, serine and alanine. Mitochondrial pre-sequences show a statistical bias of positively charged amino acid residues, provided mostly through arginine residues; very few sequences contain negatively charged amino acids. Mitochondrion-targeting peptides also share an ability to form an amphilic alpha-helix.

A complete description of a method to identify a MTS is available in: M. G. Claros, P. Vincens, 1996 (Eur. J. Biochem. 241, 779-786 (1996), "*Computational method to predict mitochondrially imported proteins and their targeting sequences*"), the content of which is herein incorporated by reference.

Software is available to the skilled person to identify the MTS of a given sequence. Illustrative software notably comprises the MitoProt® software, which is available e.g. on the web site of the Institut für Humangenetik; Technische Universität München, Germany. The MitoProt® software calculates the N-terminal protein region that can support a Mitochondrial Targeting Sequence and the cleavage site. The identification of the N-terminal mitochondrial targeting peptide that is present within a protein gives a direct access to the nucleic acid sequence, i.e. to the MTS (e.g. by reading the corresponding positions in the nucleic acid sequence coding for said protein).

Illustrative human MTS peptide sequences and human 3'UTR originating from human nuclearly-encoded mitochondrially-targeted mRNA are given in FIGS. 11A, 11B, 11C, 11D, 11E, 11F, 11G, 11H and 11I.

SEQ ID NOs are as follows:

TABLE 7

| Illustrative human mRNAs which are nuclearly-encoded but mitochondrially-targeted | MTS peptide | FIG. |
|---|---|---|
| ACO2 | SEQ ID NO: 32 | 11A |
| SOD2 | SEQ ID NO: 34 | 11B |
| ATP5b | SEQ ID NO: 36 | 11C |
| UQCRFS1 | SEQ ID NO: 48 | 11D |
| NDUFV1 | SEQ ID NO: 40 | 11E |
| NDUFV2 | SEQ ID NO: 42 | 11F |
| ALDH2 | SEQ ID NO: 44 | 11G |
| COX10 | SEQ ID NO: 46 | 11H |

3'UTR:

The 3'UTR of a RNA molecule is defined as the fragment of this RNA molecule that extends from the STOP codon to the end of the molecule. According to the universal genetic code, there are three possible STOP codons: TGA, TAA, TAG.

An online data base gives direct access to 3'UTR sequences.

Illustrative 3'UTR sequences which can used in accordance with the invention are shown in FIGS. 11A, 11B, 11C, 11D, 11E, 11F, 11G, 11H and 11I (Accession numbers of these sequences are also indicated).

SEQ ID NOs are as follows:

TABLE 8

| Illustrative human mRNAs which are nuclearly-encoded but mitochondrially-targeted | 3'UTR | FIG. |
| --- | --- | --- |
| ACO2 | SEQ ID NO: 33 | 11A |
| SOD2 | SEQ ID NO: 35 | 11B |
| ATP5b | SEQ ID NO: 37 | 11C |
| UQCRFS1 | SEQ ID NO: 39 | 11D |
| NDUFV1 | SEQ ID NO: 41 | 11E |
| NDUFV2 | SEQ ID NO: 43 | 11F |
| ALDH2 | SEQ ID NO: 45 | 11G |
| COX10 | SEQ ID NO: 47 | 10 |
| AK2 | SEQ ID NO: 57 | 11I |

Vectors of the Invention:

The present invention relates to a vector which is adapted to the efficient and stable delivery of a protein into the mitochondrion of an animal or human cell, preferably a mammalian cell, most preferably a human cell.

The vector of the invention can be produced in the form of a recombinant vector. Advantageously, the vector of the invention is an expression vector.

A vector of the invention comprises:
at least one nucleic acid sequence encoding a mitochondrion-targeting signal (also referred to as: MTS nucleic acid sequence),
at least one nucleic acid sequence which encodes said protein to be delivered, in accordance with the universal genetic code (also referred to as: CDS), and
at least one 3' nucleic acid sequence.

Said at least one MTS nucleic acid sequence is a co-translational MTS nucleic acid sequence, or a conservative fragment or variant thereof.

Said at least one 3' nucleic acid sequence is a co-translational 3'UTR nucleic acid sequence or the DNA sequence of such a co-translational 3'UTR, or a conservative fragment or variant thereof.

Preferably, said vector does not comprise a non-co-translational 3'UTR.

Said vector does not use a post-translation importation pathway, but uses a co-translation importation pathway from nucleus to said mitochondrion.

The delivery of protein according to the invention not only comprises the translocation of the protein-encoding nucleic acid from nucleus towards mitochondrion, but also comprises the translation of the encoded protein in the cytosol but at proximity of the mitochondrion (on mitochondrion-bound polysomes), and the effective importation of the translated protein into said mitochondrion. The invention provides a very advantageous importation mechanism compared to prior art techniques, which provided the mitochondrion with mature proteins at an unsatisfactory level of efficiency.

The present invention further provides a stable importation of said protein into the mitochondrion. It means that the protein rescue obtained by the invention is a rescue that is stable over time: the fibroblasts of a LHON patient transfected by a vector of the invention (expressing ND1) has grown in vitro for at least 20 days on a galactose culture medium. To the best of the inventors' knowledge, this is the first time that a culture of LHON patient fibroblasts can be kept growing for such a long period on a galactose medium.

The invention thus relates to a vector adapted to the efficient and stable delivery of a protein into the mitochondrion of an animal or human cell, preferably a mammalian cell, most preferably a human cell, which comprises:
at least one mitochondrion-targeting nucleic acid sequence (MTS nucleic acid sequence),
at least one nucleic acid sequence which encodes said protein in accordance with the universal genetic code (CDS), and
at least one 3' nucleic acid sequence, which is located in 3' of said at least one MTS nucleic acid sequence and said at least one CDS.

Preferably, said at least MTS nucleic acid sequence is in 5' position compared to said at least one CDS sequence, whereby the vector has the following structure (from 5' to 3'): at least one MTS nucleic acid sequence—at least one CDS—at least one 3'UTR.

Said at least one MTS nucleic acid sequence is:
the MTS RNA sequence of a nuclearly-encoded mitochondrially-targeted mRNA, preferably the MTS RNA sequence of a naturally-occurring nuclearly-encoded mitochondrially-targeted mRNA, or
the cDNA sequence of such a MTS RNA sequence, or
a DNA sequence coding for such a MTS RNA sequence in accordance with the universal genetic code, or
a conservative variant or fragment of such a RNA or cDNA or DNA MTS sequence, which derives therefrom by deletion and/or substitution and/or addition of one or several nucleotides, but has retained a mitochondrion-targeting function.

In other words, said at least one MTS nucleic acid sequence is:
the RNA sequence of a MTS which targets a (preferably naturally-occurring) nuclearly-transcribed mRNA to the surface of a mitochondrion in a cell collected from a healthy animal or human being, or in a normal animal or human cell, or
the cDNA sequence of such a MTS RNA sequence, or
a DNA sequence coding for such a MTS RNA sequence in accordance with the universal genetic code, or
a conservative variant or fragment of such a RNA or cDNA or DNA MTS sequence, which derives therefrom by deletion and/or substitution and/or addition of one or several nucleotides, but has retained a mitochondrion-targeting function.

Preferably, said at least one MTS nucleic acid sequence is:
the cDNA sequence of a MTS of a nuclearly-encoded mitochondrially-targeted mRNA, or
a conservative variant or fragment of such a cDNA sequence, which derives therefrom by deletion and/or substitution and/or addition of one or several nucleotides, but has retained a mitochondrion-targeting function.

Said at least one 3' nucleic acid sequence is:
the 3'UTR sequence of a nuclearly-encoded mitochondrially-targeted mRNA, preferably the 3'UTR sequence of a naturally-occurring nuclearly-encoded mitochondrially-targeted mRNA, or the cDNA sequence of such a 3'UTR sequence, or a DNA sequence coding for such a 3'UTR sequence in accordance with the universal genetic code, or a conservative variant or fragment of such a RNA or cDNA or DNA 3'UTR sequence, which derives therefrom by deletion and/or substitution and/or addition of one or several nucleotides, and which, when replacing the wild-type 3'UTR of said nuclearly-encoded mitochondrially-targeted mRNA, still allows for a mitochondrial targeting of the resulting mRNA.

In other words, said at least one 3' nucleic acid sequence is:

the RNA sequence of the 3'UTR of a nuclearly-transcribed mitochondrially-targeted mRNA, i.e. the RNA sequence of the 3'UTR of a (preferably naturally-occurring) nuclearly-transcribed RNA which is targeted to the surface of a mitochondrion in a cell collected from a healthy animal or human being, or in a normal animal or human cell, or the cDNA sequence of such a 3'UTR sequence, or a DNA sequence coding for such a 3'UTR sequence in accordance with the universal genetic code, or a conservative variant or fragment of such a RNA or cDNA or DNA 3'UTR sequence, which derives therefrom by deletion and/or substitution and/or addition of one or several nucleotides, and which, when replacing the wild-type 3'UTR of said nuclearly-encoded mitochondrially-targeted mRNA, still allows for a mitochondrial targeting of the resulting mRNA.

Preferably, said at least one 3' nucleic acid sequence is:

the cDNA sequence of the 3'UTR sequence of a nuclearly-encoded mitochondrially-targeted mRNA, or a conservative variant or fragment of such a cDNA sequence, which derives therefrom by deletion and/or substitution and/or addition of one or several nucleotides, and which, when replacing the wild-type 3'UTR of said nuclearly-encoded mitochondrially-targeted mRNA, still allows for a mitochondrial targeting of the resulting mRNA.

The resulting vector does not use a post-translation importation pathway, but uses a co-translation importation pathway from nucleus to said mitochondrion.

Preferably, said vector (inserted nucleic acid construct included) does not comprise any sequence which would be identical to:

the 3'UTR of a naturally-occurring mRNA which is a (preferably naturally-occurring) nuclearly-transcribed but non-mitochondrially-targeted mRNA, or the cDNA sequence of such a 3'UTR sequence, or a DNA sequence coding such a 3'UTR in accordance with the universal genetic code.

Preferably, said vector (inserted nucleic acid construct included) does not comprise any sequence which would be identical to:

the 3'UTR of a mRNA which is not targeted to the surface of a mitochondrion, and preferably the 3'UTR of a naturally-occurring mRNA which is not targeted to the surface of a mitochondrion, or the cDNA sequence of such a 3'UTR sequence, or a DNA sequence coding such a naturally-occurring mRNA 3'UTR in accordance with the universal genetic code.

The present invention more particularly relates to a vector adapted to the efficient and stable delivery of a protein into the mitochondrion of a mammalian cell, which comprises:

at least one mitochondrion-targeting nucleic acid sequence (referred to as MTS nucleic acid sequence), at least one nucleic acid sequence which encodes said protein in accordance with the universal genetic code (referred to as CDS sequence), and at least one 3' nucleic acid sequence, which is located in 3' of said at least one MTS nucleic acid sequence and of said at least one CDS, wherein said at least one MTS nucleic acid sequence is:

the cDNA sequence of a MTS of a nuclearly-encoded mitochondrially-targeted mRNA, or a conservative variant or fragment of such a cDNA sequence, which derives therefrom by deletion and/or substitution and/or addition of one or several nucleotides, but has retained a mitochondrion-targeting function, wherein said at least one 3' nucleic acid sequence is:

the cDNA sequence of the 3'UTR sequence of a nuclearly-encoded mitochondrially-targeted mRNA, or a conservative variant or fragment of such a cDNA sequence, which derives therefrom by deletion and/or substitution and/or addition of one or several nucleotides, and which, when replacing the wild-type 3'UTR of said naturally-occurring mRNA, still allows for a mitochondrial targeting of the resulting mRNA, wherein said vector does not comprise any sequence which would be identical to:

the 3'UTR of a naturally-occurring mRNA which is a nuclearly-transcribed but not-mitochondrially-targeted mRNA, or the cDNA sequence of such a 3'UTR sequence, or a DNA sequence coding for such a naturally-occurring mRNA 3'UTR in accordance with the universal genetic code, whereby said vector does not use a post-translation importation pathway, but uses a co-translation importation pathway from nucleus to said mitochondrion.

Said at least one MTS nucleic acid sequence can e.g. be the MTS nucleic acid sequence of ACO2, or of SOD2, or of ATP5b, or of UQCRFS1, or of NDUFV1, or of NDUFV2, or of ALDH2, or of COX10.

Said at least one MTS nucleic acid sequence may thus code for a sequence of SEQ ID NO:32, or SEQ ID NO:34, or SEQ ID NO:36, or SEQ ID NO:38, or SEQ ID NO:40, or SEQ ID NO:42, or SEQ ID NO:44, or SEQ ID NO:46 (=the MTS peptidic or polypeptidic sequence of human ACO2, SOD2, ATP5b, UQCRFS1, NDUFV1, NDUFV2, ALDH2, COX10, respectively; see FIGS. 11A-11H).

Preferably, said at least one MTS nucleic acid sequence is the MTS nucleic acid sequence of ACO2, or of SOD2, or of ATP5b, or of COX10.

Said at least one MTS nucleic acid sequence may thus code for a sequence of SEQ ID NO:32, or SEQ ID NO:34, or SEQ ID NO:36, or SEQ ID NO:46 (=the MTS peptidic or polypeptidic sequence of human ACO2, SOD2, ATP5b, COX10, respectively).

Preferably, said at least one MTS nucleic acid sequence is SEQ ID NO: 30, or SEQ ID NO: 31 (MTS nucleic acid sequence of human COX10 and SOD2, respectively; see FIG. 10).

Said at least one 3' nucleic acid sequence can be e.g. be:

the 3'UTR sequence of ACO2, or of SOD2, or of ATP5b, or of UQCRFS1, or of NDUFV1, or of NDUFV2, or of ALDH2, or of COX10, or of AK2, or the cDNA sequence of such a 3'UTR sequence, or a DNA sequence coding for such a 3'UTR sequence in accordance with the universal genetic code.

Said at least one 3' nucleic acid sequence may thus comprise or consist of those of SEQ ID NO: 33, or SEQ ID NO: 35, or SEQ ID NO: 37, or SEQ ID NO: 39, or SEQ ID NO: 41, or SEQ ID NO: 43, or SEQ ID NO: 45, or SEQ ID NO: 47, or SEQ ID NO: 57 (=the sequences corresponding to the human 3'UTR of ACO2, SOD2, ATP5b, UQCRFS1, NDUFV1, NDUFV2, ALDH2, COX10, AK2, respectively; see FIGS. 10 and 11A-11I).

Preferably, said at least one 3' nucleic acid sequence is:
the 3'UTR sequence of ACO2, or of SOD2, or of ATP5b, or of COX10, or of AK2, or
the cDNA sequence of such a 3'UTR, or
a DNA sequence coding for such a 3'UTR sequence.

Said at least one 3' nucleic acid sequence may thus comprise or consist of SEQ ID NO: 33, or SEQ ID NO: 35, or SEQ ID NO: 37, or SEQ ID NO: 47, or SEQ ID NO: 57 (=the sequences corresponding to the human 3'UTR of ACO2, SOD2, ATP5b, COX10, AK2, respectively; see FIGS. 10 and 11A-11I).

Preferably, said at least one 3' nucleic acid sequence is SEQ ID NO: 35 (human SOD2 3'UTR), or SEQ ID NO: 47 (human COX10 3'UTR).

Said at least one CDS nucleic acid sequence can be a RNA, a cDNA or a DNA sequence. Preferably, said at least one CDS sequence is a cDNA sequence. According to a very advantageous aspect of the invention, said at least one CDS may be any nucleic acid which codes for a protein that may be found useful for a mitochondrion. Contrary to prior art techniques, the technology of the invention is indeed not limited by the level of hydrophobicity of the encoded protein.

Said at least one CDS may thus be any nucleic acid coding for a mitochondrial protein. This nucleic acid may be a mitochondrial nucleic acid, or a nuclear nucleic acid coding for a mitochondrial protein.

Most preferably said at least one CDS sequence codes for a naturally-occurring functional mitochondrial protein, such as Cox1, Cox2, Cox3, Atp6, Atp8, Cytb, Nd1, Nd2, Nd3, Nd4, Nd41, Nd5, Nd6.

Preferably, said at least one CDS sequence is the sequence of a naturally-occurring mitochondrial nucleic acid, recoded in accordance with the universal genetic code.

The mitochondrial nucleic acids use a mitochondrial genetic code which is slightly different from the universal genetic code that is used by nuclear nucleic acids.

When the protein to be imported into said mitochondrion corresponds to a naturally-occurring mitochondrial protein, the naturally-occurring form of its nucleic acid sequence follows the mitochondrial genetic code.

When such a mitochondrial nucleic acid has to be inserted in the vector of the invention, the mitochondrial nucleic acid sequence has to be recoded in accordance with the universal genetic code, as the vector directs a co-translational importation process from nucleus to mitochondrion. Hence, a nuclear-encoded version of the mitochondrial nucleic acid sequence has to be created. This nuclear-encoded version can be produced by codon substitution in the mitochondrial nucleic acid, so as to replace those codons which are read by the mitochondrial genetic system with codons of the universal genetic code. For example, the mammalian UGA codon directs insertion of a tryptophan in mitochondria, but is a stop codon in the nuclear genetic code. Therefore, the UGA codon of a mitochondrial nucleic acid has to be replaced with UGG which codes for tryptophan in the universal genetic code.

TABLE 4 universal vs. mitochondrial genetic code

| codon | Universal code | Human mitochondrial code |
|---|---|---|
| UGA | Stop | Trp |
| AGA | Arg | Stop |
| AGG | Arg | Stop |
| AUA | Ile | Met |

Codon usage in mitochondria vs. the universal genetic code is described in Lewin, Genes V, Oxford University Press; New York 1994, the content of which being incorporated by reference.

Codon substitutions notably include:
UGA to UGG,
AGA to UAA, UAG or UGA,
AGG to UAA, UAG or UGA,
AUA to AUG, CUG or GUG,
AUU to AUG, CUG or GUG.

Said at least one CDS sequence may e.g. a nucleic acid sequence coding for Atp6, or Nd1, or Nd4, such as a nucleic acid sequence of ATP6, or of ND1, or of ND4, recoded in accordance with the universal genetic code (e.g. a sequence of SEQ ID NO:27, NO:28 or NO:29, see FIG. 9).

Said at least one CDS sequence may e.g. a nucleic acid sequence a nucleic acid sequence coding for Cox1, Cox2, Cox3, Atp8, Cytb, Nd2, Nd3, Nd41, Nd5, Nd6, such as a nucleic acid sequence of COX1, COX2, COX3, ATP8, Cytb, ND2, ND3, ND41, ND5, ND6.

The description of the thirteen naturally-occurring mitochondrial nucleic acids can be found in Andrew et al. 1999 (Nat Genet. 1999 October; 23(2): 147).

Preferably, said recoding is made taking into account the preferred usage codon of said mammalian cell, and most preferably taking into account the human preferred usage codon.

When recoding mitochondrial nucleic acid according to the universal genetic code, it is according to the present invention very advantageous to take into account the preferred codon usage of the subject or patient, to which the vector or nucleic acid of the invention is to be administered.

Preferred codon usage principles, as well as examples of preferred codon usage for various organisms can e.g. be found in Klump and Maeder, 1991 (Pure & Appl. Chem., vol. 63, No. 10, pp. 1357-1366 "the thermodynamic basis of the genetic code"), the content of which is herein incorporated by reference. An illustrative preferred codon usage for human beings is shown in Table 3 below (see example 2).

Said at least one CDS sequence may e.g. the nucleic acid sequence of SEQ ID NO:28 or of SEQ ID NO:29 (i.e. a nucleic acid sequence of ND1 or of ND4, recoded in accordance with the universal genetic code, and taking into account the human preferred usage codon).

The vector of the invention may e.g. comprise:
at least one SOD2 MTS nucleic acid sequence and at least one SOD2 3'UTR, or
at least one COX10 MTS nucleic acid sequence and at least one COX10 3'UTR, or
any combination of these MTS nucleic acid sequences and 3'UTR that the skilled person may find appropriate.

Such a vector may e.g. comprise a recoded ATP6, ND1 or ND4 as CDS.

The vector of the invention may e.g. comprise at least one sequence of SEQ ID NO:21 (COX10 MTS-re-coded ATP6-

COX10 3'UTR), SEQ ID NO:22 (SOD2 MTS-re-coded ATP6-SOD2 3'UTR), SEQ ID NO:25 (COX10 MTS-re-coded ND1-COX10 3'UTR), SEQ ID NO:26 (COX1 MTS-re-coded ND4-COX10 3'UTR).

Alternatively, said at least one CDS sequence may be the nucleic acid sequence of a nuclear nucleic acid which encodes a functional mitochondrial protein, e.g., a naturally-occurring nuclear nucleic acid which encodes a functional mitochondrial protein.

More particularly, said at least one nuclear nucleic acid can be a nuclearly-transcribed mitochondrially-targeted mRNA, or the cDNA sequence of such a mRNA, or the DNA sequence coding for such a mRNA.

More particularly, said at least one nuclear nucleic acid can be a nuclearly-transcribed mRNA which is not mitochondrially-targeted, or the cDNA sequence of such a mRNA, or the DNA sequence coding for such a mRNA.

Said vector may further comprise one or several expression control sequences.

The selection of suitable expression control sequences, such as promoters is well known in the art, as is the selection of appropriate expression vectors (see e.g. Sambrook et al. "Molecular Cloning: A laboratory Manual", $2^{nd}$ ed., vols. 1-3, Cold Spring Harbor Laboratory, 1989, the content of which is herein incorporated by reference).

Said vector may thus further comprise at least one promoter operably linked to said at least one MTS sequence, said at least one CDS sequence, said at least one 3' sequence.

Said promoter may e.g. be a constitutive promoter, such as e.g. a CMV promoter.

Said vector may further comprise a termination site.

Said vector may further comprise one of several of the following expression control sequences: insulators, silencers, IRES, enhancers, initiation sites, termination signals.

Said vector may further comprise an origin of replication.

Preferably, said promoter and said origin of replication are adapted to the transduction or infection of animal or human cells, preferably to the transduction or infection of human cells.

Said vector can e.g. a plasmid, or a virus, such as an integrating viral vector, e.g. a retrovirus, an adeno-associated virus (AAV), or a lentivirus, or is a non-integrating viral vector, such as an adenovirus, an alphavirus, a Herpes Simplex Virus (HSV).

Said vector may further comprise a nucleic acid coding for a detectable marker, such as a FLAG epitope or green fluorescent protein (GFP)

The present invention also relates to a process for the production of a vector of the invention, which comprises:
  providing a vector, and depleting from its original 3'UTR, if any,
  inserting in this vector at least one MTS nucleic acid sequence, at least one CDS sequence, and at least one 3' sequence as above-described.

As already-mentioned, said vector should preferably not comprise any sequence corresponding to the 3'UTR of a nuclearly-encoded but non-mitochondrially-targeted mRNA. To the best of the inventors' knowledge, all commercially-available vectors contain such an inappropriate 3'UTR; according to the present invention, such a 3'UTR should hence be removed from the vector. It may e.g. be replaced by an appropriate 3' sequence corresponding to a nuclearly-encoded and mitochondrially-targeted mRNA.

Nucleic Acid Construct of the Invention:

The nucleic acid construct which is carried by the vector of the invention is also encompassed by the present invention. The present invention more particularly relates to a non-naturally occurring nucleic acid construct.

A non-naturally occurring nucleic acid construct of the invention comprises:
  at least one mitochondrion-targeting nucleic acid sequence (referred to as MTS nucleic acid sequence),
  at least one nucleic acid sequence which encodes said protein in accordance with the universal genetic code (referred to as CDS sequence), and
  at least one 3' nucleic acid sequence, which is located in 3' of said at least one MTS nucleic acid sequence and of said at least one CDS sequence.

Said at least one MTS nucleic acid sequence is:
  the MTS RNA sequence of a nuclearly-encoded mitochondrially-targeted mRNA, such as the MTS RNA sequence of a naturally-occurring nuclearly-encoded mitochondrially-targeted mRNA, or
  the cDNA sequence of such a RNA, or
  a DNA sequence coding for such a MTS RNA sequence, or
  a conservative variant or fragment of such a RNA or DNA MTS sequence, which derives therefrom by deletion and/or substitution and/or addition of one or several nucleotides, but has retained a mitochondrion-targeting function.

Said at least one 3' nucleic acid sequence is:
  the 3'UTR sequence of a nuclearly-encoded mitochondrially-targeted mRNA, such as the 3'UTR sequence of a naturally-occurring nuclearly-encoded mitochondrially-targeted mRNA, or
  the cDNA sequence of such a RNA, or
  a DNA sequence coding for such a 3'UTR sequence, or
  a conservative variant or fragment of such a RNA or DNA 3'UTR sequence, which derives therefrom by deletion and/or substitution and/or addition of one or several nucleotides, and which, when replacing the wild-type 3'UTR of said nuclearly-encoded mitochondrially-targeted mRNA, still allows for a mitochondrial targeting of the resulting mRNA.

It may be provided that, when said at least one MTS nucleic acid sequence is the MTS RNA sequence of a naturally-occurring nuclearly-encoded mitochondrially-targeted mRNA, or the cDNA sequence of such a mRNA, or a DNA sequence coding for such a MTS RNA sequence in accordance with the universal genetic code, said at least one nucleic acid CDS sequence is not the CDS of this naturally-occurring nuclearly-encoded mitochondrially-targeted mRNA.

It may be provided that, when said at least one 3' nucleic acid sequence is the 3'UTR sequence of a naturally-occurring nuclearly-encoded mitochondrially-targeted mRNA, or the cDNA sequence of such a mRNA, or a DNA sequence coding for such a 3'UTR sequence, said at least one CDS sequence is not the CDS of this naturally-occurring nuclearly-encoded mitochondrially-targeted mRNA.

It may be provided that, when said at least one MTS nucleic acid sequence and said 3' nucleic acid sequence, respectively, are the MTS and 3'UTR sequences of a naturally-occurring nuclearly-encoded mitochondrially-targeted mRNA, or the cDNA sequences of such a mRNA, or a DNA sequence coding for such a mRNA sequence, then said at least one CDS sequence is not the CDS of this naturally-occurring nuclearly-encoded mitochondrially-targeted mRNA.

Preferably, said nucleic acid construct does not comprise any sequence which would be identical to:
- the 3'UTR of a naturally-occurring mRNA which is a nuclearly-transcribed but not-mitochondrially-targeted mRNA, or
- the cDNA sequence of such a 3'UTR sequence, or
- a DNA sequence coding for such a naturally-occurring mRNA 3'UTR in accordance with the universal genetic code.

The resulting nucleic acid construct does not use a post-translation importation pathway, but uses a co-translation importation pathway from nucleus to said mitochondrion.

The present invention more particularly relates to a non-naturally occurring nucleic acid construct which comprises:
- at least one mitochondrion-targeting nucleic acid sequence (referred to as MTS nucleic acid sequence),
- at least one nucleic acid sequence which encodes said protein in accordance with the universal genetic code (referred to as CDS sequence), and
- at least one 3' nucleic acid sequence, which is located in 3' of said at least one MTS nucleic acid sequence and of said at least one CDS sequence, wherein said at least one MTS nucleic acid sequence is:
- the cDNA sequence of the MTS RNA sequence of a nuclearly-encoded mitochondrially-targeted mRNA, or
- a conservative variant or fragment of such a cDNA sequence, which derives therefrom by deletion and/or substitution and/or addition of one or several nucleotides, but has retained a mitochondrion-targeting function, wherein said at least one 3' nucleic acid sequence is:
- the cDNA sequence of the 3'UTR sequence of a nuclearly-encoded mitochondrially-targeted mRNA, or
- a conservative variant or fragment of such a cDNA 3'UTR sequence, which derives therefrom by deletion and/or substitution and/or addition of one or several nucleotides, and which, when replacing the wild-type 3'UTR of said nuclearly-encoded mitochondrially-targeted mRNA, still allows for a mitochondrial targeting of the resulting mRNA, provided that, when said at least one MTS nucleic acid sequence and said at least one 3' nucleic acid sequence, respectively, are the MTS and 3'UTR sequences of a naturally-occurring nuclearly-encoded mitochondrially-targeted mRNA, or the cDNA sequences of such a mRNA, or a DNA sequence coding for such a mRNA sequence, then said at least one CDS sequence is not the CDS of this naturally-occurring nuclearly-encoded mitochondrially-targeted mRNA, and wherein said nucleic acid construct does not comprise any sequence which would be identical to:
- the 3'UTR of a naturally-occurring mRNA which is a nuclearly-transcribed but not-mitochondrially-targeted mRNA, or
- the cDNA sequence of such a 3'UTR sequence, or
- a DNA sequence coding for such a naturally-occurring mRNA 3'UTR in accordance with the universal genetic code.

Each and every feature, herein and above described for the MTS, CDS, 3' nucleic acid sequences in relation with the vector of the invention, and notably those features relating to the MTS, CDS, 3' nucleic acid sequences, of course applies mutatis mutandis to the nucleic acid construct of the invention, and more particularly to the non-naturally occurring nucleic acid construct of the invention.

Hence, it notably follows that:
- a MTS nucleic acid sequence of said nucleic acid construct can be the MTS nucleic acid sequence of ACO2, or of SOD2, or of ATP5b, or of UQCRFS1, or of NDUFV1, or of NDUFV2, or of ALDH2, or of COX10;
- a 3' nucleic acid sequence of said nucleic acid construct can be:
  - 3'UTR sequence of ACO2, or of SOD2, or of ATP5b, or of UQCRFS1, or of NDUFV1, or of NDUFV2, or of ALDH2, or of COX10, or of AK2, or
  - the cDNA sequence of such a 3'UTR sequence, or
  - a DNA sequence coding for such a 3'UTR sequence in accordance with the universal genetic code; and that illustrative nucleic acid constructs of the invention comprise or consist of a sequence of SEQ ID NO:21 (COX10 MTS-re-coded ATP6-COX10 3'UTR), and/or of SEQ ID NO:22 (SOD2 MTS-re-coded ATP6-SOD2 3'UTR), and/or of SEQ ID NO:25 (COX10 MTS-re-coded ND1-COX10 3'UTR), and/or of SEQ ID NO:26 (COX10 MTS-re-coded ND4-COX10 3'UTR).

Said non-naturally occurring nucleic acid construct may be transfected in a cell in the form of naked DNA, or in the form of a plasmid. Any transfection technology which is found convenient by the skilled person is convenient. The skilled person may e.g. proceed by electroporation, DEAE Dextran transfection, calcium phosphate transfection, cationic liposome fusion, creation of an in vivo electrical field, DNA-coated microprojectile bombardment, ex vivo gene therapy, and the like.

Said non-naturally occurring nucleic acid construct may of course alternatively and/or complementarily be inserted into a vector, such as a viral vector.

The vector and nucleic acid construct of the invention are useful for nucleic acid therapy, e.g. to reverse a cellular dysfunction caused by a mutation in nucleic acid coding for a mitochondrial protein. They enable to restore a protein function in a cell.

Engineered Cell:

The present invention also relates to an engineered cell which has been transduced or infected by a vector according to the invention, and/or transfected by a nucleic acid construct according to the invention.

Preferably, said engineered cell is an engineered animal or human cell, most preferably to a mammalian engineered cell, still more preferably to an engineered human cell.

Said engineered cell may e.g. be a bone-marrow cell, a clonal cell, a germ-line cell, a post-mitotic cell, such as a cell of the central nervous system; a neuronal cell, a retinal ganglion cell, a progenitor cell; or a stem cell, a hematopoietic stem cell, a mesenchymal stem cell. Preferably, said engineered cell is a neuronal cell, a retinal ganglion cell.

Said transduction, infection or transfection may be implemented by any means available to the skilled person, e.g. by electroporation, DEAE Dextran transfection, calcium phosphate transfection, cationic liposome fusion, creation of an in vivo electrical field, DNA-coated microprojectile bombardment, injection with a recombinant replicative-defective virus, homologous recombination, ex vivo gene therapy, a viral vector, naked DNA transfer, and the like.

Said engineered cell may e.g. be a cell, such as a neuronal cell, collected from a patient suffering from a disease related to a mitochondrial dysfunction. The vector and nucleic acid construct of the invention can indeed be used for ex vivo cell therapy.

Pharmaceutical Compositions and Applications

The present invention also relates to a pharmaceutical composition comprising at least one vector according to the invention, or at least one nucleic acid construct according to the invention, or at least one engineered mammalian cell according to the invention.

The present invention also relates to a drug comprising at least one vector according to the invention, or at least one nucleic acid construct according to the invention, or at least one engineered mammalian cell according to the invention.

The compositions of the present invention may further comprise at least one pharmaceutically and/or physiologically acceptable vehicle (diluent, excipient, additive, pH adjuster, emulsifier or dispersing agent, preservative, surfactant, gelling agent, as well as buffering and other stabilizing and solubilizing agent, etc.).

Appropriate pharmaceutically acceptable vehicles and formulations include all known pharmaceutically acceptable vehicles and formulations, such as those described in "Remington: The Science and Practice of Pharmacy", $20^{th}$ edition, Mack Publishing Co.; and "Pharmaceutical Dosage Forms and Drug Delivery Systems", Ansel, Popovich and Allen Jr., Lippincott Williams and Wilkins.

In general, the nature of the vehicle will depend on the particular mode of administration being employed. For instance, parenteral formulations usually comprise, in addition to the one or more contrast agents, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

The composition can be e.g., be in the form of a liquid solution, suspension, emulsion, capsule, sustained release formulation, or powder.

The pharmaceutical composition and drug of the invention are useful for the therapeutic and/or palliative and/or preventive treatment of a disease, condition, or disorder related to a defect in activity or function of mitochondria.

A mitomap is available on the MITOMAP website; this site notably provides with a list of mitochondrial disease-associated mutations.

Scientific publication review relating to mitochondrial disease, condition, or disorder notably comprise Carelli et al. 2004 (Progress in Retinal and Eye Research 23: 53-89), DiMauro 2004 (Biochimica et Biophysica Acta 1659:107-114), Zeviani and Carelli 2003 (Curr Opin Neurol 16:585-594), and Schaefer et al. 2004 (Biochimica et Biophysica Acta 1659: 115-120), the contents of which being herein incorporated by reference.

Diseases, conditions or disorders related to a defect in mitochondria activity or function notably comprise myopathies and neuropathies, such as optic neuropathies. Examples of mitochondrial diseases, conditions or disorders comprise: aging, aminoglycoside-induced deafness, cardiomyopathy, CPEO (chronic progressive external ophtalmoplegia), encephalomyopathy, FBSN (familial bilateral stritial necrosis), KS (Kearns-Sayre) syndrome, LHON (Leber's hereditary optic neuropathy), MELAS (mitochondrial myopathy, encephalopathy, lactic acidosis, and stroke-like episodes), MERRF (myoclonic epilepsy with stroke-like episodes), MILS (maternally-inherited Leigh syndrome), mitochondrial myopathy, NARP (neropathy, ataxia, and retinis pigmentosa), PEO, SNE (subacute necrotizing encephalopathy).

Optic neuropathies notably comprise:
Leber's hereditary optic neuropathy (LHON), which involves one or several point mutation(s) in mitochondrial DNA, more particularly point mutation(s) in the ND1 and/or ND4 and/or ND6 gene(s), such as G3460A (ND1 mutation), G11778A (ND4 mutation), T14484C (ND6 mutation),
the dominant optic atrophy (DOA), also known as Kjer's optic neuropathy, which involves a defect in nuclear gene OPA1,
the FBSN, MILS and NARP, which are the result of a mutation in the MTATP6 gene (defective ATP synthesis), which can be corrected by restoring the activity of function of ATP6.

Leber's hereditary optic neuropathy (LHON) was the first maternally inherited disease to be associated with point mutations in mitochondrial DNA and is now considered the most prevalent mitochondrial disorder. The pathology is characterized by selective loss of retinal ganglion cells leading to central vision loss and optic atrophy, prevalently in young males. It is a devastating disorder with the majority of patients showing no functional improvement and remaining within the legal requirement for blind registration. Other clinical abnormalities have also been reported in LHON patients. These include postural tremor, peripheral neuropathy, non-specific myopathy, movement disorders and cardiac arrhythmias [8]. The three most common pathogenic mutations from LHON affect complex ND1 and/or ND4 and/or ND6 genes with the double effect of lowering ATP synthesis and increasing oxidative stress chronically.

Each of said disease, condition or disorder could be corrected by restoring activity or function of the mutated DNA.

Example 1 below illustrates the rescue of an ATP6 activity or function with a vector and nucleic acid of the invention. Example 2 below illustrates the rescue of a ND1 and ND4 activity or function with a vector and nucleic acid of the invention (fibroblasts collected from LHON patients).

The pharmaceutical compositions or drugs of the invention are more particularly intended for the therapeutic and/or palliative and/or preventive treatment of a myopathy or of an optic neuropathy, such as LHON, DOA, FBSN, MILS or NARP.

The present invention relates to the use of at least one vector or nucleic acid construct for in vivo or ex vivo therapy of a subject or patient in need of a therapeutic, palliative or preventive treatment of a disease, condition, or disorder related to a defect in activity or function of mitochondria.

The present invention also relates to the use of at least one vector or nucleic acid construct of the invention, or of at least one engineered cell of for the treatment of a disease, condition, or disorder related to a defect in activity or function of mitochondria, and more particularly for the production of a composition, pharmaceutical composition or drug intended for the treatment of such a disease condition, or disorder.

The present invention more particularly relates to a method for the therapeutic and/or palliative and/or preventive treatment of a disease, condition, or disorder related to a defect in activity or function of mitochondria, which comprises:
administering to a subject or patient in need thereof a vector and/or a nucleic acid construct and/or an engineered cell of the invention, in a quantity effective for the therapeutic and/or palliative and/or preventive treatment of said subject or patient, ex vivo treating cells collected from a subject or patient in need thereof, and returning the treated cells to the subject or patient.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of"). Each of the relevant disclosures of all references cited herein is specifically incorporated by reference.

The present invention is illustrated by the following examples, which are given for illustrative purposes only.

EXAMPLES

Example 1: Allotopic Expression of the ATP6 Mitochondrial Gene is Significantly Improved by the Localization of its mRNAs to the Surface of Mitochondria Leading to an Efficient Import of the Precursor Abstract:

It is clear that impairment of mitochondrial energy metabolism is the key pathogenic factor in a growing number of neurodegenerative disorders. With the discovery of mtDNA mutations, the replacement of defective genes became an important goal for mitochondrial geneticists worldwide. Unfortunately, before the present invention, it was still not possible to introduce foreign genes into the mitochondria of mammalian cells.

To circumvent this problem, allotopic expression in the nucleus of genes encoded by mitochondrial DNA (mtDNA), became an attractive idea. However, for most mitochondrial genes tested, there were important limitations related to the high hydrophobicity of the corresponding proteins, which impedes their mitochondrial translocation.

We herein elucidate the mechanisms that enable the delivery of mRNAs encoding mitochondrial proteins to the organelle surface, and demonstrate that this delivery depends on two sequences: the region coding for the mitochondrial targeting sequence (MTS) and the 3'UTR. mRNA sorting to mitochondrial surface permits to optimize allotopic approach, by enhancing the mitochondrial import efficiency of the precursor synthesized in the cytosol. As an illustration of this mechanism, we have chosen to utilize the sequence coding for the MTS and the 3'UTR of two nuclear genes encoding mitochondrial proteins: COX10 and SOD2 associated to a recoded mitochondrial ATP6 gene. Indeed, COX10 and SOD2 mRNAs localize to the mitochondrial surface in HeLa cells. HeLa cells transfected with these constructions express an Atp6 protein which is successfully delivered to the mitochondria. Hence, we have been able to optimize the allotopic approach for Atp6, and our procedure will next be tried to rescue mitochondrial dysfunction in patients presenting ATP6 mutations.

Introduction:

To examine the possibility that allotopic expression of mtDNA genes could be optimized by a targeted localization of the mRNA to the mitochondrial surface, we have chosen to utilize the sequences coding for the MTS and the 3'UTR of two nuclear genes encoding mitochondrial proteins: COX10 and SOD2 associated to an reengineered nucleus-localized ATP6 gene. COX10 encodes a highly hydrophobic protein of the inner mitochondrial membrane, its mRNAs localizes to the mitochondrial surface [5]. SOD2 encodes a mitochondrial protein involved in detoxification, its mRNA, as COX10 mRNA, localizes to the mitochondrial surface [5] and a recent report described that in HeLa cells, its 3'UTR is associated to the mitochondrial surface via the Akap121 protein [6]. The ability to synthesize and direct the Atp6 protein to mitochondria was examined in Hela cells for 4 plasmids: two of them only contain the mts of COX10 or SOD2, and the two other possess both the MTS and the 3'UTR of each gene. Hybrid mRNAs were detected for each construction in both transiently and stably transfected cells. Further, Atp6 protein was also visualized by indirect immunofluorescence associated to the surface of mitochondria. Mitochondria isolated from transfected cells were examined for the presence of Atp6 protein. Remarkably, hybrids mRNAs possessing both the MTS and the 3'UTR of either COX10 and SOD2 allow the synthesis of a polypeptide which is imported in a highly efficient way from the cytosol into the mitochondria. Thus, the strategy of directing a hybrid mRNA to the mitochondrial surface significantly improves the feasibility of the allotopic approach for mitochondrial genes.

Material and Methods:

Plasmid construction: The full-length ATP6 mitochondrial gene was reengineered after the production of the 677 pb product by RT-PCR (Superscript III one step RT-PCR Platinium Taq HiFi, Invitrogen), using total RNA from HeLa cells. The PCR product obtained was cloned in the PCR 2.1-Topo vector (Invitrogen, Life technologies). In this vector, we recoded 11 non-universal codons in the ATP6 gene by four rounds of in vitro mutagenesis (Quik change Multi site-directed mutagenesis kit; Stratagene, La Jolla, Calif.). Six oligonucleotide primers were designed to alter AUA codons to AUG and UGA to UGG (Table 1).

TABLE 1

In vitro mutagenesis of the ATP6 mitochondrial gene

| Name | sequence | Length (bp) |
|---|---|---|
| ATP6.1 | CAATGGCTAATCAAACTAACCTCAAAACAAATGATGACCA TGCACAACACTAAAGGACGAACCTGGTCTCTTATGCTA (SEQ ID NO: 1) | 78 |

TABLE 1-continued

In vitro mutagenesis of the ATP6 mitochondrial gene

| Name | sequence | Length (bp) |
|---|---|---|
| ATP6.2 | TCTATGAACCTAGCCATGGCCATCCCCTTATGGGCGGGC ACAGTGATTATGGGC (SEQ ID NO: 2) | 54 |
| ATP6.3 | CCCATGCTAGTTATTATCGAAACCATCAGCCTACTCATTCA ACCAATGGCC (SEQ ID NO: 3) | 51 |
| ATP6.4 | ACCCTAGCAATGTCAACCATTAAC (SEQ ID NO: 4) | 24 |
| ATP6.5 | ACTAAAGGACGAACCTGGTCTCTTATGCTAGTATCCTTAA TC (SEQ ID NO: 5) | 42 |
| ATP6.6 | ACACCAACCACCCAACTATCTATGAACCTAGCCATGGCCA TC (SEQ ID NO: 6) | 42 |

The intermediate construct was sequenced for accuracy. To this recoded ATP6, we appended in frame either the MTS of COX10 or SOD2, obtained by RT-PCR using total RNA from HeLa cells (Superscript III one step RT-PCR Platinium Taq HiFi; Invitrogen, Life technologies). For COX10 we amplified the sequence corresponding to the first 28 amino acids, for SOD2 the sequence coding for the first 30 amino acids. Oligonucleotide primers used for the amplification include at its 3' extremity a Sal1 restriction site for the subsequent cloning in frame with the reengineered ATP6 gene which possesses a Sal1 restriction site at its 5' extremity (Table 2).

The final sequences of the fusion ATP6 genes were checked for accuracy, and inserted in the pCMV-Tag 4A vector (Stratagene, La Jolla Calif.), which will direct the synthesis of the protein via the CMV promoter and its detection by the presence of a FLAG epitope tag appended to the C-terminal region of Atp6. To obtain hybrid mRNAs which will also contain the 3'UTR of COX10 or SOD2 genes we replaced the SV40 polyA signal present in the pCMV-Tag 4A vector (positions 1373-1679) using Pvu1 and Mlu1 restriction enzymes, by the 1429 bp of the full-length COX10 3'UTR or the 215 pb of the SOD2 3'UTR. Both 3'UTR were first obtained by RT-PCR using RNAs purified

TABLE 2

Oligonucleotides primers for RT-PCR analysis

Figure 1B:
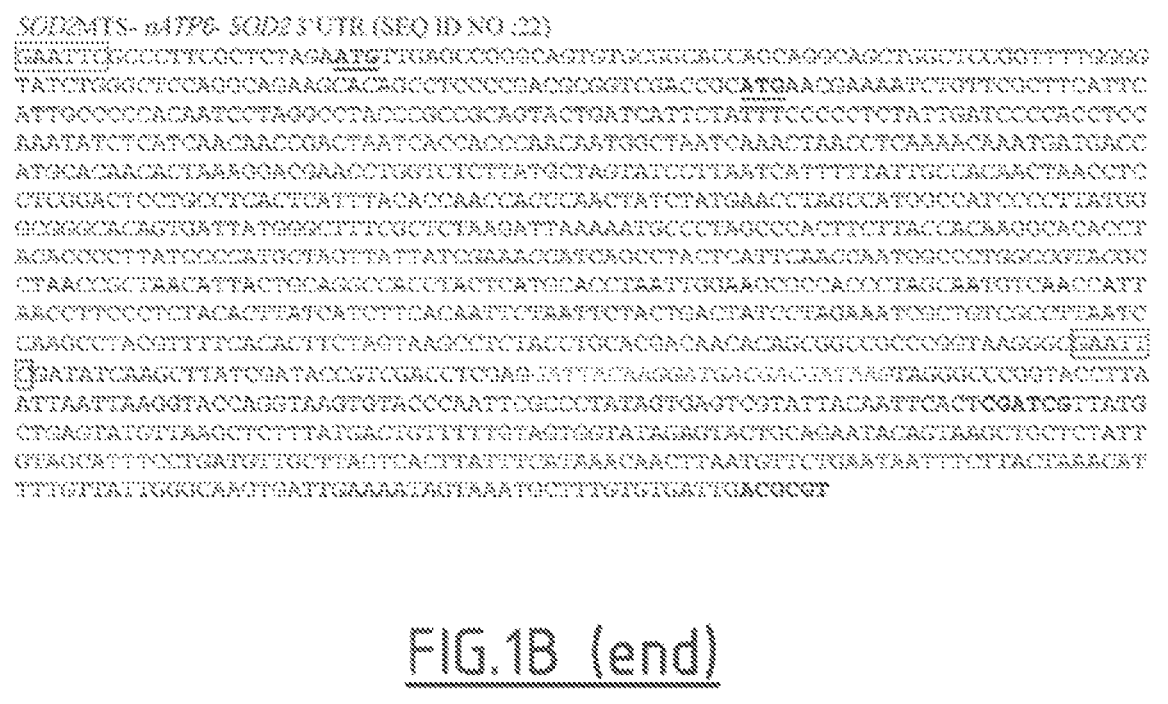

| Name | 5' Primer (5'-3') | 3' Primer (5'-3') | RT-PCR product length (bp) |
|---|---|---|---|
| ATP6 ORF | GTCGACCGCATGA ACGAAAATCTGTTC GCTTCATTCATT (SEQ ID NO: 7) | CCGGGCGGCCGCTGT GTTGTCGTGCAGGTA GAGGCTTAC (SEQ ID NO: 8) | 677 |
| MTS COX10 | CGCTCTAGAATGG CCGCATCTCCGCA CACTCTC (SEQ ID NO: 9) | GCGGTCGACTTCAAG ATACCAGACAGAGCC TCC (SEQ ID NO: 10) | 84 |
| UTR COX10 | CCCGATCGGAGCA CTGGGACGCCCAC CGCCCCTTTCCC (SEQ ID NO: 11) | CGCACGCGTAAAGCT TCTACAAATGTGAAGG CTGTAACA (SEQ ID NO: 12) | 1429 |
| MTS SOD2 | CGCTCTAGAATGTT GAGCCGGGCAGTG TGCGGC (SEQ ID NO: 13) | GTCGACCGCGTCGGG GAGGCTGTGCTTCTG CCT (SEQ ID NO: 14) | 90 |
| 3'UTR SOD2 | ACCACGATCGTTAT GCTGAGTATGTTAA GCTCTTTA (SEQ ID NO: 15) | CGCACGCGTCAATCA CACAAAGCATTTACTA TTTTC (SEQ ID NO: 16) | 215 |
| COX6c | ATGGCTCCCGAAG TTTTGCCAAAACCT (SEQ ID NO: 17) | CTGAAAGATACCAGC CTTCCTCATCTC (SEQ ID NO: 18) | 250 |
| SOD2 | GGACTACGGCGCC CTGGAACCTCACA TCAACGC (SEQ ID NO: 58) | | | from HeLa cells and specific oligonucleotide primers containing Pvu1 and Mlu1 restriction sites at each end (cf. Table 2 above). PCR fragments were first cloned in the PCR 2.1-Topo vector (Invitrogen, Life technologies) and sequenced to verify that no mistakes were generated before subcloning in the pCMV-Tag 4A vector. The four final constructs were entirely sequenced for accuracy using specific oligonucleotide primers to verify the full-length sequences of either the fusion ATP6 genes or the 3'UTR regions appended to them. Final sequences inserted in the pCMV-Tag 4A vectors are shown in FIG. 1B.

The sequence of recoded ATP6 (SEQ ID NO: 27) is shown on FIG. 9. The MTS and 3'UTR sequences of COX10 and SOD2 are shown on FIG. 10 (SEQ ID NO: 30, 47, 31 and 60).

Cell Culture and Transfection:

We cultured HeLa cells with RPMI medium complemented with 10% of foetal bovine serum (Gibco, Invitrogen), gentamicin (0.01%), 2 mM glutamine, optionally with pyruvate (e.g., 2.5 mM), optionally with antibiotics (such as 100 u/mL penicillin, 100 µg/mL streptomycin). They were transfected with FuGENE 6 transfection reagent as recommended by the manufacturer (Roche Biochemicals, Indianapolis). Briefly, monolayer Hela cells were seeded a day before transfection at 50% confluence, so the next day they will be at approximately 80% confluence, the cells were plated in a medium without antibiotics. 2 microgrammes of different plasmids purified with Quiagen plasmid midi kit (Quiagen; Valencia, Calif.) were used. Between 48 to 60 hr later, 80% of the transfected cells were used either for immunochemistry analyses or RNA and mitochondria extractions. The remaining 20% of cells were selected for neomycine, G418, resistance (selectable marker present in the pCMV-Tag 4A vector) at a final concentration of 1 mg/ml. Stable clones were expanded for several weeks, immunochemistry analyses were performed. Mitochondria were also isolated to determine the import ability of the Atp6 protein.

Immunocytochemistry: Coverslips were placed on the bottom of 24-well dishes and HeLa cells seeded at approximately 50% confluence (80000 cells). 60 hours after transfection, cells were fixed with 2% paraformaldehyde in PBS for 15 min and processed for indirect immunofluorescence. After permeabilization of the cells for 5 min with Triton 1% in PBS, cells were incubated for one hour in PBS with 1% BSA before the addition of the primary antibodies: mouse monoclonal anti-Flag M2 antibodies (Stratagene, La Jolla Calif.) or mouse monoclonal anti-ATP synthase subunit beta (Molecular Probes, Invitrogen). Both antibodies were used at a final concentration of 1 microgramme/ml. The incubation with primary antibodies was performed for either 2 hr at room temperature or overnight at 4° C. After washing the primary antibody three times five min with PBS, cells were incubated with the secondary antibody: labeled goat-anti-mouse☐IgG Alexa Fluor 488 (Molecular Probes, Invitrogen). This antibody was used in 1% BSA-PBS at 1:600 dilution and placed on the top of the coverslips for two hr. The cells were, subsequently, washed once in PBS for 5 min. For DNA and mitochondria staining, a second wash was performed with 0.3 microgrammes/ml of DAPI (Sigma, Saint Louis, Mich.) and 100 nM of MitoTracker Deep Red 633 (Molecular probes, Invitrogen) for 20 min. A last 10 min wash was performed in PBS and the coverslips were mounted using Biomeda Gel/Mount. Immunofluorescence was visualized in a Leica DM 5000 B Digital Microscope. Digital images were acquired and processed with the Meta-Vue imaging system software.

Mitochondria isolation and western blot analysis: Between 20 to 40 millions or 100 millions of transiently or stably transfected HeLa cells were treated with trypsin (Gifco, Invitrogen) for 5 min and spin down. One wash in PBS was performed. The pellets were resuspended in 10 ml of homogenization buffer: 0.6 Mannitol, 30 mM Tris-HCl PH 7.6, 5 mM MgAc and 100 mM KCl, 0.1% fatty acid-free bovine serum albumin (BSA), 5 mM beta-mercaptoethanol and 1 mM PMFS. To the resuspended cells 0.01% of digitonin was added. After a 4 min incubation on ice the homogenization was performed with 15 strokes in a Dounce glass homogenenizer with a manually driven glass pestle type B. Homogenates are centrifuged for 8 min at 1000 g at 4° C. to pellet unbroken cells and nuclei. Since many mitochondria remain trapped in this pellet, it was resuspended and rehomogenized again with 5 ml of homogenization buffer and 25 additional strokes. Then a second round of centrifugation under the same conditions was performed. Both supernatants were assembled and centrifuged again to discard any nuclear or cell contaminant. The supernatant obtained was centrifuged at 12000 g at 4° C. for 30 min to pellet mitochondria. Four washes in homogenization buffer were performed to free the mitochondrial fraction of particles containing membranes, reticulum endoplasmic and proteases. The last two washes were performed in a homogenization buffer devoid of BSA and PMFS to allow a better estimation of the protein concentration in the final mitochondrial fraction and its subsequent analysis by proteinase K digestion. Protein concentrations in the extracts were measured using the dye-binding assay Bradford. To determine whether Atp6 was translocated into the organelle, 15 microgrammes of mitochondrial proteins were treated with 200 microgrammes/ml of proteinase K (PK) at 0° C. for 30 min. Samples were then resolved in 4-12 gradient or 12% polyacrylamide SDS-PAGE, and transferred to nitrocellulose. Filters were probed with the following antibodies: mouse monoclonal anti-Flag M2 antibodies (Stratagene, La Jolla Calif.) which recognizes the nuclear recoded Atp6 protein in which a flag epitope was appended at its C-terminus or mouse monoclonal anti-ATP synthase subunit alpha (Molecular Probes, Invitrogen), which recognizes the 65 kDa nuclear encoded alpha-subunit of the ATP synthase, Complex V. Immunoreactive bands were visualized with anti-mouse coupled to horseradish peroxidase (1:10000) followed by ECL Plus detection (Amersham International) according to the manufacturer's instructions.

Five independent mitochondria purifications from cells stably transfected with either $SOD2^{MTS}$ $ATP6$-$3UTR^{SV40}$ or $SOD2^{MTS}$ $ATP6$-$3'UTR^{SOD2}$ vectors were performed. The amount of precursor and mature forms of ATP6 in mitochondria, as well as the quantities of both the mature form of ATP6 and ATP☐resistant to PK proteolysis were compared by densitometric analyses (Quantity One, Biorad software system). The significance of the differences observed was validated with a paired Student's t-test.

RNA Extraction and RT-PCR Analyses:

Mitochondria extractions were performed as described in the precedent section, with the following modifications: 400 millions of cells were treated with 250 µg/ml cycloheximide for 20 minutes at 37° C. To HB was added 200 Mg/ml cycloheximide, 500 µg/ml heparine and 1/1000 RNase inhibitor (rRNasin, Promega). The last pellet of crude mitochondria associated with polysomes (M-P) was stored at −80° C. until RNA extraction. Free-cytoplasmic polysomes (F-P) were obtained from the post-mitochondrial supernatant fraction by sedimentation through a step gradient of 2 M and 0.5 M sucrose. RNAs from these two fractions, as well as total RNAs from each stably transfected cell line, were obtained using RNeasy Protect Mini kit (Qiagen). Generally, 10 millions of cells are sufficient to obtain approximately 30 microgrammes of total RNA. The presence of the hybrid ATP6 mRNA was examined using primers which recognize the first 27 nt of either COX10 or SOD2 MTS and a primer which recognize the last 27 nt of the ATP6 ORF. For the pCMV-Tag 4A vector containing both the MTS and the 3'UTR of COX10 or SOD2, we used a primer recognizing the last 27 nt of each 3'UTR. 100 ng of RNA was used for reverse transcription (cf. Table 1 above). The products were then subjected to 25 cycles of PCR using Superscript III one step RT-PCR Platinium Taq kit (Invitrogen). As an internal control a 250 nt fragment within the ORF of COX6c gene, encoding a mitochondrial protein, was also amplified. Ten percent of the amplified products were run in agarose gels, and the quantities of amplified products reflecting hybrid ATP6 mRNA amount in each preparation was estimated using the Photocap software (Vilber Lourmat; Torcy, France).

Tables 1 and 2 above, and table 9 below, show primer sequences, the expected sizes of the PCR products, the quantity of RNA used for reverse-transcription and the number of PCR cycles performed.

Densitometric analyses (Quantity One, Bio-Rad software) were performed the amount of both hybrid ATP6 and SOD2 transcripts in either mitochondrion-bound polysomes or free-cytoplasmic polysomes. Three independent RNA preparations from M-P and F-P fractions were subjected three times to RT-PCR analyses.

mitochondrial DNA mutations. However, up today a major obstacle remains to be overcome and is the targeting of the recoded protein to mitochondria. We then decided to force the localization of the recoded ATP6 mRNA to the mitochondrial surface. The rationale behind this specific mRNA targeting is to allow a co-translational import mechanism which will maintain the precursor in an import competent conformation impeding its aggregation before or during translocation through the TOM (Translocase of the outer membrane) and TIM (Translocases of the inner membrane) import complexes. Two sequences within mRNAs are believed to be involved in their localization to the mitochondrial membrane: the sequence coding for the MTS and the 3'UTR. We have chosen two nuclearly-encoded mitochondrial genes, which mRNAs are preferentially localized to the surface of mitochondria in HeLa cells: COX10 and SOD2 [5]. Interestingly, the SOD2 mRNA has been shown to be associated to the mitochondrial surface via its 3'UTR and the Akap121 protein.

We therefore, obtained four different plasmids.

Two contain either the MTS of COX10 or the sequence encoding the first 30 amino acids of SOD2 (=the 20 amino acids of the MTS sequence of SOD2, and the ten consecutive amino acids that follows within the SOD2 sequence, i.e., fragment 1-30 of SEQ ID NO:49), in frame with the AUG codon of the recoded ATP6 gene (COX10 MTS-recoded ATP6-SV40 3' UTR; SOD2 MTS-recoded ATP6-SV40 3' UTR). In these plasmids, the SV40 polyA signal functions as the 3'UTR.

TABLE 9

| mRNA | RT-PCR product length (bp) | Primers 5' Primer | Primers 3'Primer | Total RNAs Quantity (ng) | Total RNAs Cycle numbers | Polysomal RNAs (M-P/F-P) Quantity (ng) | Polysomal RNAs (M-P/F-P) Cycle numbers |
|---|---|---|---|---|---|---|---|
| SOD2$^{MTS}$ ATP6 | 780 | MTS SOD2 5' | ATP6 ORF3' | 200 | 28 | 250 | 28 |
| ATP6 | 677 | ATP6 ORF 5' | ATP6 ORF 3' | 50 | 28 | 150 | 20 |
| SOD2 | 785 | SOD2 5' | 3'UTR SOD2 3' | 100 | 28 | 20 | 20 |
| COX6c | 250 | COX6c 5' | COX6c 3' | 200 | 28 | 250 | 20 |

Results:
Construction of Reengineered Mitochondrial ATP6 Gene for Allotopic Expression To accomplish allotopic expression we synthesized the full-length version of nuclear-encoded ATP6 mitochondrial gene converting codons AUA to AUG and codons UGA to UGG. Indeed, AUA in the mitochondrial genetic system leads to the insertion of a methionine, but according to the universal code it is an isoleucine. Additionally, UGA into mitochondria codes for a tryptophan, whereas in the cytosol it represents a stop codon. We, therefore, recoded all 11 mitochondrial codons present in ATP6 ensuring the accurate translation of the transcript by cytoplasmic ribosomes. These alterations were performed by four rounds of in vitro mutagenesis using six independent oligonucleotide primers (Table 1) and the Quik change Multi site-directed mutagenesis kit (Stratagene, La Jolla, Calif.).

The concept of allotopic approach has important implications for the development of therapies to patients with The other two combine both the MTS and the 3'UTR of COX10 and SOD2 respectively, and do not comprise the cytosolic 3'UTR of SV40 (COX10 MTS-recoded ATP6-COX10 3' UTR; SOD2 MTS-recoded ATP6-SOD2 3' UTR).

FIGS. 1A and 1B illustrate the constructs obtained and the full-length sequences inserted in the pCMV-Tag 4A vector than we named respectively: COX10 MTS-nATP6, SOD2 MTS-nATP6 and COX10 MTS-nATP6-COX10 3'UTR and SOD2 MTS-nATP6-SOD2 3'UTR.

Detection of Hybrid ATP6 mRNAs in Transiently and Stably HeLa Transfected Cells

Figure 2:
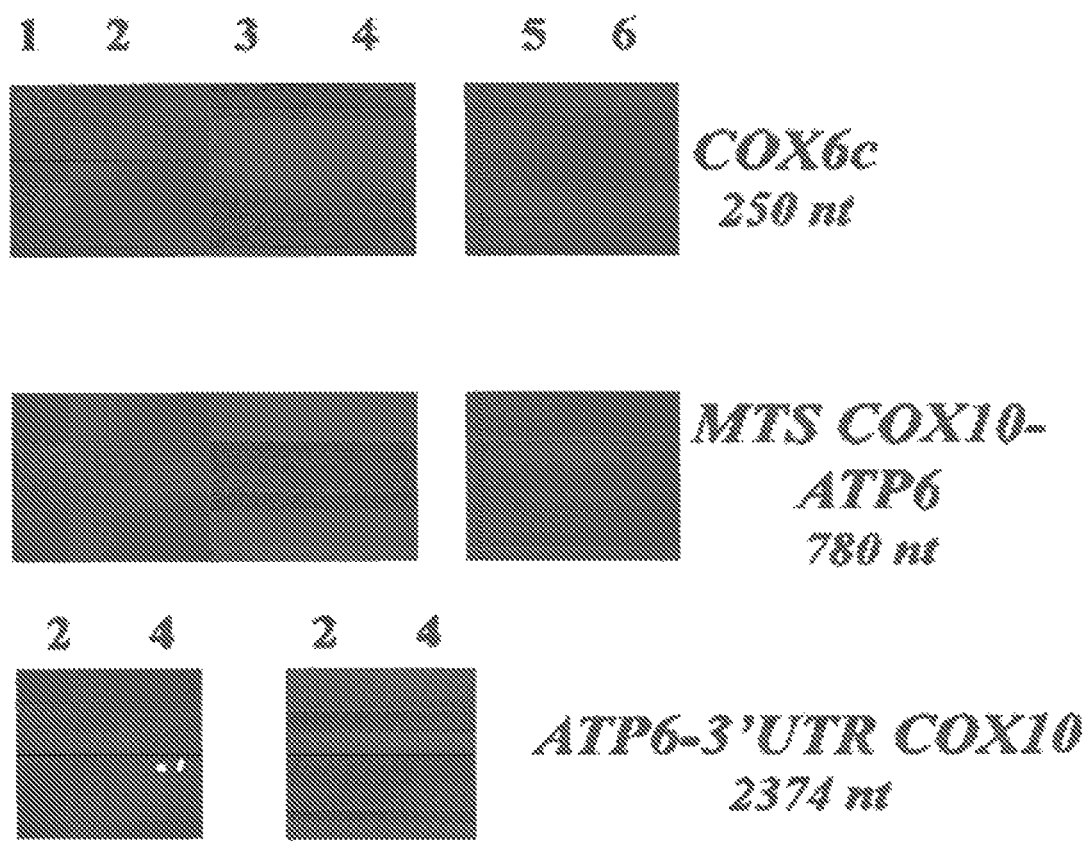
FIG. 2: RT-PCR analyses of RNAs purified from HeLa transfected cells 100 ng of total RNAs were reversed transcribed and subjected to 30 cycles of PCR amplification, 10% of amplified product were subjected to agarose electrophoresis.

To determine whether transfected cells express hybrid ATP6 mRNAs, steady-state levels of the transcripts were measured in both transiently and stably transfected cells after the isolation of total RNAs. 100 ng of total RNAs were subjected to RT-PCR analyses using specific primer oligonucleotides for hybrid ATP6 mRNA. COX6c gene encoding a mitochondrial protein was used as an internal control, with specific primers allowed the amplification of a 250 bp fragment (FIG. 2). RNAs from non-transfected HeLa cells as well as HeLa cells transfected with the empty pCMV-Tag 4A vector were also tested as negative controls. FIG. 2 shows a 780 bp PCR product corresponding to the amplification of the first 27 nt of COX10 ORF and the last 27 nt of the ATP6 ORF in cells transfected with both COX10 MTS-nATP6 and COX10 MTS-nATP6-COX10 3'UTR vectors. Additionally, RNAs isolated from cells transfected with the COX10 MTS-nATP6-COX10 3'UTR vector amplified a 2374 bp product corresponding to the entire ATP6 ORF and the full-length COX10 3'UTR. The results obtained with RNAs purified from transfected cells with SOD2 MTS-nATP6 and SOD2 MTS-nATP6-SOD2 3'UTR vectors show that hybrid ATP6 transcript was detected as a 780 nt amplified product. Further, the SOD2 MTS-nATP6-SOD2 3'UTR region amplified a 1060 bp fragment, corresponding to the entire ATP6 ORF and the full-length SOD2 3'UTR. These results indicate that HeLa cells express the reengineered ATP6 gene. Moreover, no significant differences in the steady-state levels of hybrid mRNAs were found by the addition of either COX10 3'UTR or SOD23'UTR.

To examine the ability of SOD2 signals associated to the recoded ATP6 gene to direct hybrid mRNAs to the mitochondrial surface, we determined their subcellular localization in the four stably cell lines obtained. In this purpose, we isolated RNAs from mitochondrion-bound polysomes (M-P) and free-cytoplasmic polysomes (F-P) and we determined by RT-PCR the steady-state levels of hybrid mRNAs in both polysomal populations (FIG. 12B). As internal controls, the subcellular distribution of endogenous mitochondrial ATP6, SOD2 and COX6c mRNAs were determined. Endogenous ATP6 mRNA exclusively localized to the mitochondrial compartment as expected. Besides, endogenous SOD2 mRNA is enriched in mitochondrion-bound polysomes (M-P), whereas COX6c mRNA is preferentially detected in free-cytoplasmic polysomes (F-P) as we have previously observed. The SOD2MTSATP6-3'UTRSOD2 vector directed the synthesis of a hybrid mRNA that was almost undetectable in free-cytoplasmic polysomes. Hybrid mRNA produced from the SOD2MTSATP6-3'UTRSV40 plasmid was also detected preferentially in mitochondrion-bound polysomes. However, it was also present in free-cytoplasmic polysomes (FIG. 12B). Densitometric analyses were performed to determine the amount of both endogenous SOD2 and hybrid ATP6 mRNAs in each polysomal population examined. SOD2 mRNA signal in mitochondrion-bound polysomes was 85.6%±6.15 in cell lines expressing the SOD2MTSATP6-3'UTRSV40 plasmid and 82.5%±4.87 in cells expressing the SOD2MTSATP6-3'UTRSOD2 vector. Interestingly, it was found for the ATP6 hybrid mRNA that only 72.4%±5.2 localized to the mitochondrial surface in cells expressing the SOD2MTSATP6-3'UTRSV40 vector. Instead, in cells expressing the SOD2MTSATP6-3'UTR-SOD2 vector 84.6%±4.7 of the hybrid mRNA localized to the mitochondrial surface (FIG. 12C). These values were significantly different according to the paired Student's t-test (P<0.0034, n=6). Thus, the combination of both the MTS and 3'UTR of SOD2 to the reengineered ATP6 gene leads to the synthesis in the nucleus of a transcript which was almost exclusively sorted to the mitochondrial surface. Indeed, its subcellular distribution is not significantly different to the one of the endogenous SOD2 mRNA.

TABLE 10

| Hela cells | ATP6 mRNA signal localized at the mitochondrial surface | ATP6 mRNA within the mitochondria |
|---|---|---|
| With a cytosolic 3'UTR (SV40 3' UTR) | 72.4% ± 5 | 0.71 ± 0.12 |
| With a mitochondrial 3'UTR (SOD2 3'UTR), and without any cytosolic 3'UTR | 82.5 ± 4.8 | 1.28 ± 0.24 |

Detection of ATP6 Allotopic Expression in HeLa Cells by Indirect Immunofluorescence We analyzed the ability of the reengineered ATP6 product to localize to mitochondria in vivo.

For this, we appended a Flag epitope in frame to the C-terminus of the ATP6 ORF and we examined stably transfected cells by indirect immunofluorescence (FIG. 13). HeLa cells transfected with the empty pCMV-Tag 4A vector were used as negative controls and showed a low diffused signal in cytoplasm when antibodies to Flag were used (FIG. 13, left panel). Stably transfected cells with either SOD2$^{MTS}$ ATP6-3'UTR$^{SV40}$ or SOD2$^{MTS}$ ATP6-3'UTR$^{SOD2}$ vectors were visualized by indirect immunofluorescence using antibodies to Flag (FIG. 14, left panel) and to ATP synthase subunit α (FIG. 13 middle panel). For each cell type visualized, a merged image in association with DAPI staining is shown in the right panel. A typical punctuate mitochondrial pattern was observed in cells expressing the recoded ATP6 polypeptides, when the Flag antibody was used. This indicates that fusion ATP6 proteins localized to mitochondria.

Immunocytochemistry to detect the flag epitope in HeLa cells transiently or stably transfected with the four pCMV-Tag 4A vectors showed a typical punctuate mitochondrial pattern, suggesting that the fusion Atp6 protein had been localized within the mitochondria (FIG. 3). Indeed, this typical punctuate mitochondrial pattern was also observed using either the mitochondrion-specific dye Mito Tracker Red or specific antibodies anti-ATP synthase subunit beta. HeLa cells transfected with the empty pCMV-Tag 4A vector were used as negative controls and showed a diffuse cytoplasmic distribution but with a low intensity (FIG. 3). The localization patterns of the different Atp6 peptides which synthesis were directed by the four pCMV-Tag 4A vectors were essentially identical confirming that both COX10 and SOD2 sequences successfully allowed the reengineered Atp6 protein to localize to the mitochondria in vivo.

Translocation of the Fusion Atp6 Protein into Mitochondria of HeLa Cells

To determine whether reengineered ATP6 gene products are efficiently imported into mitochondria in vivo, mitochondria isolated from stably transfected HeLa cells were subjected to western blot analysis (FIG. 4). We visualized two forms with anti-flag antibodies of approximately 30 and 20 kDa, representing the precursor and mature forms of the recoded ATP6 protein.

The predicted molecular weights of both proteins are respectively 34 and 30 kDa, larger than the ones implied by the molecular weight markers. This discrepancy has often been observed when extremely hydrophobic proteins were migrated in SDS-PAGE. In general, the electrophoretic mobility on SDS-PAGE of proteins encoded by mtDNA is higher than the one expected for their theoretical molecular weights.

The steady-state levels of both polypeptides are similar in the two cell lines examined: cells transfected with MTS COX10-nATP6 vector (MTS COX10-nATP6), and cells transfected with MTS COX10-nATP6-COX10 3'UTR (MTS COX10-nATP6-3'UTR).

To determine the amounts of the recoded ATP6 polypeptides produced in HeLa cells expressing either $SOD2^{MTS}$ ATP6-3'UTR$^{SV40}$ or $SOD2^{MTS}$ ATP6-3'UTR$^{SOD2}$ vectors, we compared six independent mitochondrial extractions (FIG. 14A). Both precursor and mature polypeptides were equally abundant in mitochondria from each cell line, indeed the expression of $SOD2^{MTS}$ ATP6-3'UTR$^{SV40}$ vector leads to an accumulation of 61.4%±6 of the precursor form. Instead, $SOD2^{MTS}$ ATP6-3'UTR$^{SOD2}$ vector directed the synthesis of 64.4%±6.5 of the precursor. These values were not significantly different according to the paired Student's t-test. Similar results were obtained when total extracts from each cell line were examined by Western blotting. This data is in agreement with the overall amounts of hybrid ATP6 mRNAs detected when total RNAs from cell lines expressing either $SOD2^{MTS}$ ATP6-3'UTR$^{SV40}$ or $SOD2^{MTS}$ ATP6-3'UTR$^{SOD2}$ vectors were subjected to RT-PCR analyses (FIG. 12A). Therefore, the steady-state levels of the ATP6 precursor and its ability to recognize the TOM complex in the outer mitochondrial membrane do not depend on the presence of the SOD2 3'UTR. Notably, the relative proportions of ATP6 precursor and mature forms were analogous to the ones shown in cells for highly hydrophobic proteins en route to the mitochondria.

When mitochondria were treated with 150 or 200 microgrammes/ml of proteinase K (PK) the precursor forms of the fusion ATP6 protein were sensitive to proteolysis in both cells lines. In contrast the mature form of ATP6 is resistant to PK digestion, especially in cells expressing the MTS COX10-nATP6-COX10 3'UTR transcript. Indeed, in these cells the amount of the mature ATP6 protein is approximately 185% higher than in cells expressing the MTS COX10-nATP6 mRNA. These data strongly indicates that not only the precursor polypeptide is correctly addressed to the surface of mitochondria, as we observed by indirect immunofluorescence (FIG. 3), but also that it was efficiently translocated into the organelle and correctly processed. Moreover, FIG. 4 shows that the quantity of the mature form of the Atp6 protein and the 65 kDa ATPalpha protein inside the mitochondria were quite similar after proteinase K digestion. Therefore, the use of COX10 MTS allows an efficient mitochondrial translocation of the recoded ATP6 protein, and when COX10 MTS is combined to the 3'UTR of COX10 a significant more efficient in vivo translation/import of the allotopically expressed ATP6 gene is obtained.

FIG. 14B upper panel shows a schematic representation of the theoretically expected ATP6 import intermediate. The hydrophobic passenger ATP6 precursor can be trapped en route to the matrix and a mitochondrial processing peptidase can cleave the MTS. Nevertheless, the rest of the protein remained accessible to PK action and therefore becoming undetectable on Western blotting. Instead, the fraction of the ATP6 protein which can be completely translocated is insensitive to PK-induced proteolysis and can therefore be integrated into the inner mitochondrial membrane, hence, remaining detectable on immunoblotting.

FIG. 14B shows that precursor forms of the fusion proteins were sensitive to proteolysis in both cell line examined. Nearly all the ATP6 precursor signal disappeared after PK digestion, so precursors that were engaged in the process of translocation or loosely attached to the outer mitochondrial membrane but not fully translocated, were entirely digested (FIG. 14B, middle panel). In contrast, a significant amount of the mature form of ATP6 is resistant to PK digestion, indicating its location inside the organelle. To examine the levels of another complex V protein in these cells, immunoblots were performed using anti-ATP synthase α antibody. This naturally imported mitochondrial protein was present at similar extents in all cells tested. Only one band of approximately 65 kDa was visualized suggesting that either we were unable to discriminate the precursor and mature forms of this protein under the electrophoretic conditions used or precursor polypeptides were very rapidly and efficiently translocated. Additionally, no major differences of the ATP synthase α signals were detected after PK treatment, confirming the integrity of the mitochondrial isolations (FIG. 14B, middle panel). To compare the import efficiency of the recoded ATP6 proteins in cells transfected with either $SOD2^{MTS}$ ATP6-3'UTR$^{SV40}$ or $SOD2^{MTS}$ ATP6-3'UTR$^{SOD2}$ vectors, we measured the amount of the mature form of ATP6 insensitive to PK digestion in each cell line, after normalization with the amount of ATP synthase α resistant to PK proteolysis. Results for six independent mitochondrial extractions subjected to immunoblotting analyses were shown in FIG. 15B, lower panel. Overall results show that both SOD2 signals lead to a high efficient import of the recoded ATP6 precursor. Remarkably, the level of the mature form insensitive to PK proteolysis in cells transfected with $SOD2^{MTS}$ ATP6-3'UTR$^{SOD2}$ (1.28±0.24) was 1.8 fold higher than in cells expressing the $SOD2^{MTS}$ ATP6-3'UTR$^{SV40}$ (0.71±0.12). The difference measured was significant according to the paired Student's t-test ($P<0.0022$, n=6). This observation could be related to the higher enrichment in the mitochondrion-bound polysomes of the corresponding mRNA (FIG. 12B).

The question arises whether imported reengineered ATP6 proteins were assembled into the ATP synthase complex. The complex is organized in F0-F1 domains, F1 sector is a water-soluble unit located in the matrix and having the ability to hydrolyse ATP. The F0 domain is embedded in the inner membrane and is composed by hydrophobic subunits forming a proton pathway. ATP6 is an intrinsic protein of F0, composed of five putative transmembranous α-helices. In contrast, ATP synthase α is a located in the matrix F1 domain. Studies performed with bovine heart mitochondria demonstrated that ATP6 was degraded at a very low rate when F0 subunits were subjected to trypsine treatment. Therefore, we treated mitochondria with both PK and Triton X-100 (1%). The detergent disrupts both mitochondrial membranes and theoretically leads to the entire proteolysis of mitochondrial proteins, demonstrating their localization somewhere inside the organelle in a protease-sensitive form. FIG. 3C shows that indeed ATP synthase α was fully digested by PK; instead a significant amount of ATP6 remained insensitive to PK proteolysis. This result suggests that the recoded ATP6 was assembled into complex V.

Discussion:

Recent, epidemiological studies demonstrated that as a group, disorders of the mitochondrial function affect at least 1 in 5000 of the population, making them among the most common genetically determined disorders. In spite of the fact that over the last decade, the underlying genetic bases of several mitochondrial diseases involving central nervous system degeneration, no effective therapy is available for mitochondrial disorders. Pathogenic point mutations of genes encoded by the mitochondrial genome have been described as the cause of many mitochondrial disorders. A possible therapeutic approach is therefore to exploit the natural mitochondrial protein import pathway. The basic concept is to introduce a wild-type copy of the mutated mitochondrial gene into the nucleus and import normal copies of the gene product into mitochondria from cytosol. This concept has been termed allotopic expression and several reports in yeast described that a number of non mitochondrial polypeptides can be relocated to the mitochondrial matrix simply by conjugating a targeting sequence to their N-terminus. However, when this approach has been tried in mammalian cells using different MTS and genes encoded by mtDNA, precursors were not imported efficiently into mitochondria. By consequence, the rescue of mitochondrial defect in patient cells was not only partial but also temporary [7]. Therefore, up today the spectrum of mtDNA encoded polypeptides than can be successfully expressed and integrated into mitochondrial respiratory chain complexes is very limited. This limitation is thought to be the consequence of the high hydrophobicity nature of mtDNA encoded proteins, which possess transmembrane domains refractive to mitochondrial import. The precursor synthesized in the cytosol could lack the import-competent structure required for an efficient mitochondrial membrane translocation.

The concept of mesohydrophobicity is likely to be an important factor for mitochondrial import competency. Mesohydrophobicity describes the average hydrophobicity in a window of 60-80 amino acids, together with the calculation of the most hydrophobic 17-amino acid segment. This calculation could predict importability of hydrophobic peptides. Using their algorithm, we analyzed this correlation to assess the mitochondrial importability of $SOD2^{MTS}$ ATP6 gene product and compared to ATP6, COX8 and SOD2 polypeptides as well as the previously tested fusion protein $COX8^{MTS}$ ATP6: as the wild-type ATP6, both fusion proteins examined cannot be translocated into mitochondria, mainly due to the high hydrophobicity of ATP6. Hence, a possibility that can allow the import of a recoded ATP6 protein into the organelle is that the precursor is engaged in a co-translational pathway of import. Thereby, the precursor would be maintained in a loosely folded nonaggregated conformation required for translocation through the mitochondrial import apparatus. To overcome this limitation and try to develop a more long-term and definitive rescue of mtDNA mutations by allotopic expression leading to its application in gene therapy, we decided to construct nuclear versions of the mtDNA encoded ATP6 gene in which we appended the signals intended for forcing the hybrid mRNA to localize to the mitochondrial surface. We have chosen COX10 and SOD2 genes, which transcripts are enriched in the mitochondrial surface.

We were able to demonstrate that the association to a recoded ATP6 gene of both the MTS and 3'UTR signals leading to a mRNA delivery to the mitochondrial surface unambiguously improves the feasibility of the allotopic approach for mitochondrial genes. Indeed, not only we were able to visualize the protein in the mitochondria by indirect immunofluorescence, but most important the amounts of the processed Atp6 polypeptide inside the organelle were quite similar to the naturally imported ATPalpha protein. This result strongly indicates that the recoded Atp6 precursor was efficiently imported, the improvement we were able to produce as compared to other recent reports [1], [2], [3], [4] is certainly due to the fact that the hybrid mRNA was addressed to the mitochondrial surface, therefore enhancing the coupling between translation and mitochondrial import processes.

Most interestingly, we obtained a gradual improvement, indeed the use of either COX10 or SOD2 MTS alone, gave a good result in which approximately 50% of the mature ATP6 protein is translocated inside the mitochondria. When each MTS was combined to the corresponding 3'UTR, at least 85% of the mature ATP6 protein is insensitive to proteinase K digestion indicating that almost all the protein synthesized in the cytoplasm is successfully translocated inside the mitochondria.

To accomplish allotopic expression, the localization of an mRNA to the mitochondrial surface has never been tried before. In the allotopic approaches reported, even though different MTS were appended to recoded mitochondrial genes, all the constructs examined contained at their 3'extremities the SV40 polyA signal that does not lead to any specific subcellular localization of the transcript. Our data clearly demonstrate that the association to a recoded ATP6 gene of both the MTS and 3'UTR signals of the SOD2 gene leads to a high efficient delivery of the hybrid mRNA to the mitochondrial surface. This improves unambiguously the feasibility of the allotopic approach for this mitochondrial gene. Indeed, not only were we able to visualize ATP6 protein in the mitochondria by indirect immunofluorescence but definitely the amount of the processed ATP6 polypeptide inside the organelle was quite similar to the naturally imported ATP synthase subunit of a Complex V component, such as is ATP6. These data strongly indicate that recoded ATP6 precursors were successfully imported. The improvement we obtained compared to a recent report, which measured 18.5% of the precursor translocated, is certainly due to the localization of hybrid mRNAs to the mitochondrial surface. This specific localization obviously enhances the coupling between translation and import processes, therefore, diminishing the block of the precursor during its translocation through the TOM and TIM complexes. It is worth mentioning that we obtained a gradual improvement on mitochondrial import of the ATP6 precursor. When both the MTS and the 3'UTR of SOD2 were combined, the amount of fully translocated ATP6 protein was 1.8-fold higher than when just the MTS was present. This is likely related to the improvement of mRNA sorting to the mitochondrial surface when both cis-acting elements of SOD2 were associated to the recoded ATP6 gene. Remarkably, proteolysis insensitivity of the translocated ATP6 protein in the presence of both PK and Triton X-100 suggested that the protein could be correctly assembled in the F0 domain of the respiratory chain Complex V. Notably, combining the cis-acting elements of the COX10 gene to the recoded ATP6 gene, we obtained a very efficient mitochondrial import ability of the fusion protein. Indeed, COX10 mRNA codes for a highly hydrophobic protein involved in Complex IV biogenesis, and SOD2 mRNA is enriched at the mitochondrial surface in human cells.

We clearly demonstrated that the association to a recoded ATP6 gene of both the MTS and 3'UTR signals of either SOD2 or COX10 genes leads to a high efficient delivery of hybrid ATP6 mRNAs to the mitochondrial surface, especially when both the MTS and the 3'UTR of SOD2 or COX10 were associated to the reengineered ATP6 gene. This specific subcellular localization of hybrid mRNAs leads to a high efficiency in the mitochondrial translocation of the recoded ATP6 proteins. Remarkably, when both the MTS and the 3'UTR of either SOD2 or COX10 were combined, the amount of fully translocated ATP6 protein was 1.8-fold higher than when the MTS was associated to the cytosolic SV40 3'UTR. Therefore, the improvement of mRNA sorting to the mitochondrial surface when both cis-acting elements of SOD2 or COX10 were associated to the recoded ATP6 gene definitely increase the amount of the processed ATP6 polypeptide inside the organelle which became quite similar to the naturally imported ATP synthase subunit α, a Complex V component, such as is ATP6. Thus, by directing a hybrid mRNA to the mitochondrial surface we significantly improve the feasibility of the allotopic approach for the ATP6 mitochondrial gene.

In conclusion, we optimize the allotopic expression approach for ATP6, by the use of mRNA targeting signals without any amino acid change in the protein that could affect biologic activity.

This approach becomes henceforth available to rescue mitochondrial deficiencies caused by mutations in mtDNA genes.

Example 2: Correct Mitochondrial Localization of the Recoded Mitochondrial ND1 and ND4 Genes in Fibroblastes from LHON Patients The three most common pathogenic mutations from LHON affect complex ND1, ND4 and ND6 genes with the double effect of lowering ATP synthesis and increasing oxidative stress chronically.

Since we have demonstrated that reengineered mitochondrial Atp6 proteins were successfully translocated inside the mitochondria in HeLa cells (see example 1 above), we decided to synthesize recoded mitochondrial genes ND1 and ND4. To ensure the efficient import of the allotopically expressed proteins we appended to them signals which will direct the corresponding mRNAs to the mitochondrial surface. We have chosen to use the MTS of COX10 gene alone or in combination with its entire 3'UTR. FIGS. 5A and 5B illustrate the constructs obtained and the full-length sequences inserted in the pCMV-Tag 4A vector.

Material and Methods:

Cell culture and transfection: Fibroblasts were obtained from LHON patients of the Hôpital Necker Enfants Malades, Paris, France (Département de Génétique). We cultured these cells with D-MEM medium complemented with 10% of foetal bovine serum, pyruvate, gentamicin (0.01%), and 2 mM glutamine. When indicated cells were grown in glucose-free medium supplemented with 10 mM galactose.

Fibroblasts were transfected with FuGENE 6 transfection reagent as recommended by the manufacturer (Roche Biochemicals, Indianapolis). Briefly, monolayer fibroblast cells were seeded a day before transfection at 50% confluence, so the next day they will be at approximately 80% confluence, the cells were plated in a medium without antibiotics. 2 microgrammes of different plasmids purified with Quiagen plasmid midi kit (Quiagen; Valencia, Calif.) were used. Between 48 to 60 hr later, 80% of the transfected cells were used for immunochemistry analyses. The remaining 20% of cells were selected for neomycine, G418, resistance (selectable marker present in the pCMV-Tag 4A vector) at a final concentration of 0.25 mg/ml. Stable clones were expanded for several weeks.

Optimized Recoding into Human Genetic Code mtDNA has been recoded according to human genetic code, taking into account the preferred codon usage in human:

TABLE 3

| Source | | Human preferred codon usage |
|---|---|---|
| ARG | CGA | — |
| | CGC | — |
| | CGG | — |
| | CGU | — |
| | AGA | — |
| | AGG | AGG |
| LEU | CUA | — |
| | CUC | — |
| | CUG | CUG |
| | CUU | — |
| | UUA | — |
| | UUG | — |
| SER | UCA | — |
| | UCC | UCC |
| | UCG | — |
| | UCU | — |
| | AGC | — |
| | AGU | — |
| THR | ACA | — |
| | ACC | ACC |
| | ACG | — |
| | ACU | — |
| PRO | CCA | — |
| | CCC | CCC |
| | CCG | — |
| | CCU | — |
| ALA | GCA | — |
| | GCC | GCC |
| | GCG | — |
| | GCU | — |
| GLY | GGA | — |
| | GGC | GGC |
| | GGG | — |
| | GGU | — |
| VAL | GUA | — |
| | GUC | — |
| | GUG | GUG |
| | GUU | — |
| LYS | AAA | — |
| | AAG | AAG |
| ASN | AAC | AAC |
| | AAU | — |
| GLN | CAA | — |
| | CAG | CAG |
| HIS | CAC | CAC |
| | CAU | — |
| GLU | GAA | — |
| | GAG | GAG |
| ASP | GAC | GAC |
| | GAU | — |
| TYR | UAC | UAC |
| | UAU | — |
| CYS | UGC | UGC |
| | UGU | — |
| PHE | UUC | UUC |
| | UUU | — |
| ILE | AUC | AUC |
| | AUA | |
| | AUU | — |
| MET | AUG | AUG |
| TRP | UGG | UGG |
| % GC | | 63/42 |

ND1 and ND4 Constructs:

COX10 MTS-nND1-SV40 3' UTR, COX10 MTS-nND4-SV40 3' UTR, COX10 MTS-nND1-COX10 3'UTR, and COX10 MTS-nND4-COX10 3'UTR were produced as described above in example 1 for ATP6. The resulting sequences are shown on FIG. 5B (SEQ ID NO:23, 24, 25, 26, respectively).

Results:
Detection of ND1 Allotopic Expression in Fibroblasts from LHON Patients Presenting the G3460A ND1 Mutation We analyzed the ability of the reengineered ND1 product to localize to mitochondria in vivo. Immunocytochemistry analyses were performed to detect the flag epitope in fibroblasts, from a patient presenting the ND1 gene mutated, transiently transfected with either COX10 MTS-nND1-SV40 3' UTR or COX10 MTS-nND1-COX10 3'UTR showed a typical punctuate mitochondrial pattern, suggesting that the fusion Nd1 protein had been localized within the mitochondria (FIG. 6). Indeed, this typical punctuate mitochondrial pattern was also observed using specific antibodies anti-ATP synthase subunit beta. Cells transfected with the empty pCMV-Tag 4A vector were used as negative controls and showed a diffuse cytoplasmic distribution but with a low intensity (FIG. 6). The localization patterns of Nd1 peptides which synthesis were directed by the two vectors examined were essentially identical confirming that COX10 sequences successfully allowed the reengineered Nd1 protein to be addressed inside the mitochondria.

Detection of ND4 Allotopic Expression in Fibroblasts from LHON Patients Presenting the G11778A ND4 Mutation Two plasmids directing the synthesis in the cytosol of a recoded wild-type ND4 gene were obtained. One of them, COX10 MTS-nND4-SV40 3' UTR, possesses appended to the N-terminus of the protein the sequence corresponding to the first 28 amino acids of Cox10. The second one, COX10 MTS-nND4-COX10 3'UTR, has in addition at the end of the ORF the full-length 3'UTR of COX10. Fibroblasts from a patient presenting 100% of mtDNA molecules with the G11778A ND4 mutation were transiently transfected with either one of these plasmids. 60 h later cells were fixed and visualized to determine the ability of the COX10 sequences to target the recoded protein to the mitochondria. FIG. 7 shows that in both cases the fusion MTS Cox10ND4Flag protein did have a punctuate staining pattern, which is very similar to the one observed for the same cells with the naturally imported mitochondrial protein ATP synthase subunit beta. Thus, implying that the recoded Nd4 fusion protein was imported into mitochondria.

In conclusion, as for the mitochondrial ATP6 gene, we were able to optimize the allotopic expression approach for ND1 and ND4 genes, by the simply use of mRNA targeting signals without any amino acid change in the protein that could affect biologic activity.

Growth Ability of LHON Fibroblasts in Galactose Medium

Fibroblasts presenting the G3460A ND1 mutation were grown with galactose, which slowly enters glycolysis as compared to glucose. FIG. 8 shows major differences in cell growth after six day culture: fibroblasts presented a severe growth defect, less that 10% of the cells survived in medium containing galactose as compared to cells seeded in glucose-rich medium. Stably transfected fibroblasts with the MTS COX10-nND1-COX10 3'UTR vector had a markedly improved rate of growth in galactose compared with that of non-transfected cells. This result implies that the mitochondrially imported recoded ND1 protein had assembled successfully into functional complex I allowing, therefore, a rescue of mitochondrial dysfunction in these cells.

Example 3: Rescue of Mitochondrial Deficiency Causing Human Diseases (Transfection of Fibroblasts from a NARP Patient)

We also determined whether the reengineered ATP6 protein would be able to rescue mitochondrial deficiency in cells having a mutated ATP6 gene.

We obtained fibroblasts from a patient presenting NARP disease caused by the T8993G mutation in the ATP6 gene.

Fibroblasts were cultured on media containing sodium pyruvate and relatively high amounts of FBS, more particularly:
on a medium containing glucose (D-MEM with L-glutamine, 4500 mg/L D-glucose, 110 mg/L sodium pyruvate 2.5 mM, FBS 15%, uridine 28 microM), or
on a medium, which does not contain glucose, but contain galactose (liquid D-MEM (1×), with L-Glutamine without Glucose, sodium pyruvate 2.5 mM, galactose 10 mM, FBS 15%, uridine 28 microM).

Stably transfected cells expressing the nuclear version of ATP6 associated with either SOD2 MTS alone, or in combination with SOD2 3'UTR, were obtained. Respiratory chain activity has been examined by the ability of these cells to grow in a medium in which glucose has been replaced by galactose for either 10 or 20 days. NARP cells expressing the empty vector had a low survival rate (30%). Cells expressing ATP6 with either the MTS of SOD2 or both the MTS and the 3'UTR of SOD2 present a growth survival of approximately 60%. If the selection was maintained for 20 days, the survival growth rate of cells expressing our optimized vectors was superior to 80% (FIG. 16). Only subtle differences of survival rate were observed for fibroblasts expressing either the vector with both the MTS and 3'UTR of the SOD2 gene or the vector with the SOD2 MTS associated to the SV40 3'UTR. This, is certainly due to the fact that these cells are heteroplasmic for the T8993G mutation, indeed they possess approximately 10% of the wild-type gene. Therefore, in their mitochondria probably 10% of a functional ATP6 protein could be assembled in Complex V. We can envision that the expression of the vector with SOD2 MTS associated to the SV40 3'UTR, will lead to the mitochondrial import of enough ATP6 protein to allow the cells to growth a good rate in galactose medium.

Preliminary measures of the real amount of ATP produced in vitro by fibroblasts expressing either ones of our vectors clearly show a difference in the activity of Complex V related to the presence of either SOD2 3'UTR or SV40 3'UTR. Hence, when compared to control fibroblasts (100% of ATP synthesis in galactose medium) NARP fibroblasts expressing the vector with SOD2 MTS associated to the SV40 3'UTR had 50%, representing an increase compared to non transfected NARP cells (30%) but was less important when compared to the amount found in cells expressing the vector which combines to the recoded ATP6 gene both the MTS and the 3'UTR of the SOD2 gene (approximately 85%); cf. FIG. 19. By consequence, a more complete and efficient rescue of mitochondrial dysfunction is obtained when allotopic approach implies the presence of both the MTS and 3'UTR targeting signals.

TABLE 11

| Fibroblasts | Survival rate on galactose | Rate of ATP synthesis on galactose |
|---|---|---|
| Control | 100% | 100% |
| NARP (mutated ATP6) | 30% | 30% |
| NARP + cytosolic 3'UTR (SV40 3'UTR) | 60% | 50% |
| NARP + mitochondrial 3'UTR (SOD2 3'UTR) | 60% | 85% |

Example 4: Rescue of Mitochondrial Deficiency Causing Human Diseases (Transfection of Fibroblasts from LHON Patients)

The applicability potential of the improved allotopic expression approach of the inventors has been further confirmed by examining two other mtDNA genes involved in LHON. The fibroblasts obtained presented a total homoplasmy of the mutation; indeed all the molecules of mitochondrial DNA are mutated.

Fibroblasts were cultured on media containing sodium pyruvate and relatively high amounts of FBS, more particularly:
- on a medium containing glucose (D-MEM with L-glutamine, 4500 mg/L D-glucose, 110 mg/L sodium pyruvate 2.5 mM, FBS 15%, uridine 28 microM), or
- on a medium, which does not contain glucose, but contain galactose (liquid D-MEM (1×), with L-Glutamine without Glucose, sodium pyruvate 2.5 mM, galactose 10 mM, FBS 15%, uridine 28 microM).

The engineered nucleus-localized versions of ND1 and ND4 were obtained; ND1 and ND4 transcripts possess both at their 5' and 3' extremities COX10 mRNA targeting sequences. Stable transfections of these constructions in fibroblasts from LHON's patients with either ND1 or ND4 mutations were performed. Indirect immunofluorescence showed that both proteins localize to the surface of mitochondria in vivo. The OXPHOS activity of these cells has been also examined by growing in a galactose rich medium. Interestingly, fibroblast cells allotopically expressing the wild-type ND4 protein showed a markedly improved rate of growth on galactose medium. This improvement is higher when both the MTS and 3'UTR of COX10 were associated to the ND4 gene (54.3%) as compared to that of mock transfected cells (8%) or to the cells transfected with the ND4 gene associated to the MTS of COX10 and the cytosolic SV40 3'UTR (12.7%) (FIG. 17, MTS: ND4 associated to COX10 MTS and the SV40 3'UTR, 3'UTR: ND4 associated to both the MTS and 3'UTR of COX10). This data imply that in spite of the presence in these cells of the ND4 mutated polypeptide, the wild-type protein was successfully imported into the organelle and assembled in Complex I. Preliminary experiments, of in vitro measurements of ATP synthesis confirm these results, indeed in untransfected cells very little ATP was synthesized in galactose medium (14% of the control level measured in healthy fibroblasts), when cells express the ND4 gene associated to the MTS of COX10 and the cytosolic SV40 3'UTR an increased is observed (56%). Remarkably, this increase is more important when cells express the ND4 gene associated to both the MTS and 3'UTR of COX10 (84%).

Hence, our results undeniably confirm that we have optimized the allotopic approach for three mtDNA encoded genes by the use of mRNA targeting signals, without any amino acid change in the proteins. This is particularly the case when our vectors presented both the MTS and the 3'UTR targeting signals of a mRNA which exclusively localized to the mitochondrial surface.

TABLE 12

| Fibroblasts | Survival rate on galactose | Rate of ATP synthesis on galactose |
| --- | --- | --- |
| Control | 100% | 100% |
| LHON (mutated ND4) | 8% | 14% |
| LHON + cytosolic 3'UTR (SV40 3'UTR) | 12.7% | 56% |
| LHON + mitochondrial 3'UTR (COX10 3'UTR) | 54.3% | 84% |

Example 5: Transduction of Retinal Ganglion Cells

The inventors obtained, by in vitro mutagenesis, reengineered ND1, ND4, ND6 and ATP6 genes, which possess the most common mutations found in LHON's and NARP's patients: G3460A, G11778A, T14484C and T8993G respectively. Both wild-type and mutated genes have been integrated in the p-AAV-IRES-hrGFP vector, which will allow the production of infectious recombinant human Adeno-Associated Virus Type 2 (AAV2) virions. For all constructions, each nuclear version of mtDNA genes is associated to the two mRNA targeting sequences of the COX10 gene, which allow the enrichment of corresponding mRNAs at the surface of mitochondria. In accordance with the present invention, this will ensure the efficient delivery of the polypeptides inside the organelle.

Retinal ganglion cells (RGC) represent the primary cellular target of the pathogenic process of LHON disease.

The inventors purified RGCs from adult rat retina, thereby obtaining enriched RGC populations, and maintained them in culture for two weeks. Mitochondria are distributed along actin filaments and they specifically concentrated at the extremities of neuron extensions. The inventors transfected these cells with the mutated version of the ND1 gene. Preliminary results showed that the expression at high levels of the mutated protein during 8 days leads to an abnormal distribution of mitochondria along the neurite and cone extensions (FIG. 18).

BIBLIOGRAPHIC REFERENCES CITED IN THE EXAMPLES

1. Owen, R., et al., Recombinant Adeno-associated virus vector-based gene transfer for defects in oxidative metabolism. Hum. Gene Ther., 2000. 11: p. 2067-2078.
2. Guy, J., et al., Rescue of a mitochondrial deficiency causing Leber Hereditary Optic Neuropathy. Ann. Neurol., 2002. 52: p. 534-542.
3. Manfredi, G., et al., Rescue of a deficiency in ATP synthesis by transfer of MTATP6, a mitochondrial DNA-encoded gene to the nucleus. Nature Genet., 2002. 30: p. 394-399.
4. Oca-Cossio, J., et al., Limitations of allotopic expression of mitochondrial genes in mammalian cells. Genetics, 2003. 165: p. 707-720.
5. Sylvestre, J., et al., The role of the 3'UTR in mRNA sorting to the vicinity of mitochondria is conserved from yeast to human cells. Mol. Biol. Cell, 2003. 14: p. 3848-3856.
6. Ginsberg, M. D., et al., PKA-dependent binding of mRNA to the mitochondrial AKAP121 protein. J. Mol. Biol., 2003. 327(4): p. 885-897.
7. Smith, P. M., et al., Strategies for treating disorders of the mitochondrial genome. Biochem. Biophys. Acta, 2004. 1659: p. 232-239.
8. Carelli et al., Progress in Retinal and Eye Research, 2004. 23: p. 53-89

The invention claimed is:

1. An expression vector for the efficient and stable delivery of mitochondrial protein ND4 into the mitochondrion of a mammalian cell, the vector comprising in the 5' to 3'direction:
   a mitochondrion-targeting nucleic acid sequence (MTS);
   a nucleic acid sequence encoding mitochondrial ND4 protein; and
   a 3'UTR nucleic acid sequence,
   wherein the MTS comprises a nucleic acid sequence encoding the peptide consisting of the amino acid sequence as set forth in SEQ ID NO: 46;
   wherein the nucleic acid sequence encoding mitochondrial ND4 protein is as set forth in SEQ ID NO: 29; and
   wherein the 3'UTR nucleic acid sequence is selected from a group consisting of the nucleotide sequence as set forth in SEQ ID NO: 47, and nucleotides 1588 to 3010 as set forth in SEQ ID NO: 26.

2. The expression vector of claim 1, wherein the MTS consists of the nucleotide sequence as set forth in SEQ ID NO: 30.

3. The expression vector of claim 1, wherein the MTS consists of the nucleotide sequence as set forth in nucleotides 7 to 90 of SEQ ID NO. 25.

4. The expression vector of claim 1, wherein the MTS consists of the nucleotide sequence as set forth in nucleotides 7 to 90 of SEQ ID NO. 26.

5. An isolated mammalian cell comprising the expression vector according to claim 1.

6. A pharmaceutical composition comprising the expression vector according to claim 1.

7. A recombinant nucleic acid construct comprising in the 5' to 3' direction:
   a mitochondrion-targeting nucleic acid sequence (MTS);
   a nucleic acid sequence encoding mitochondrial ND4 protein; and
   a 3'UTR nucleic acid sequence,
   wherein the MTS comprises a nucleic acid sequence encoding the peptide consisting of the amino acid sequence as set forth in SEQ ID NO: 46;
   wherein the nucleic acid sequence encoding mitochondrial ND4 protein is as set forth in SEQ ID NO: 29; and
   wherein the 3'UTR nucleic acid sequence is selected from a group consisting of the nucleotide sequence as set forth in SEQ ID NO: 47, and nucleotides 1588 to 3010 as set forth in SEQ ID NO: 26.

8. The nucleic acid construct of claim 7, wherein the MTS consists of the nucleotide sequence as set forth in SEQ ID NO: 30.

9. The isolated mammalian cell of claim 5, wherein said mammalian cell is a human cell.

10. The nucleic acid construct of claim 7, wherein the MTS consists of the nucleotide sequence as set forth in nucleotides 7 to 90 of SEQ ID NO. 25.

11. The nucleic acid construct of claim 7, wherein the MTS consists of the nucleotide sequence as set forth in nucleotides 7 to 90 of SEQ ID NO. 26.

12. A pharmaceutical composition comprising the nucleic acid construct according to claim 7.

13. The isolated mammalian cell according to claim 5, wherein the cell is selected from a group consisting of a bone-marrow cell, a clonal cell, a germ-line cell, a post-mitotic cell, a neuronal cell, a retinal ganglion cell, a progenitor cell; and a stem cell.

* * * * *

SEQUENCE LISTING

<160> NUMBER OF SEQ ID NOS: 60

<210> SEQ ID NO 1
<211> LENGTH: 78
<212> TYPE: DNA
<213> ORGANISM: Artificial Sequence
<220> FEATURE:
<223> OTHER INFORMATION: Synthetic Primer

<400> SEQUENCE: 1
caatggctaa tcaaactaac ctcaaaacaa atgatgacca tgcacaacac taaaggacga     60
acctggtctc ttatgcta                                                  78

<210> SEQ ID NO 2
<211> LENGTH: 54
<212> TYPE: DNA
<213> ORGANISM: Artificial Sequence
<220> FEATURE:
<223> OTHER INFORMATION: Synthetic Primer

<400> SEQUENCE: 2
tctatgaacc tagccatggc catcccctta tgggcgggca cagtgattat gggc           54

<210> SEQ ID NO 3
<211> LENGTH: 51
<212> TYPE: DNA
<213> ORGANISM: Artificial Sequence
<220> FEATURE:
<223> OTHER INFORMATION: Synthetic Primer

<400> SEQUENCE: 3
cccatgctag ttattatcga aaccatcagc ctactcattc aaccaatggc c              51

<210> SEQ ID NO 4
<211> LENGTH: 24
<212> TYPE: DNA
<213> ORGANISM: Artificial Sequence
<220> FEATURE:
<223> OTHER INFORMATION: Synthetic Primer

<400> SEQUENCE: 4
accctagcaa tgtcaaccat taac                                            24

<210> SEQ ID NO 5
<211> LENGTH: 42
<212> TYPE: DNA
<213> ORGANISM: Artificial Sequence
<220> FEATURE:
<223> OTHER INFORMATION: Synthetic Primer

<400> SEQUENCE: 5
actaaaggac gaacctggtc tcttatgcta gtatccttaa tc                        42

<210> SEQ ID NO 6
<211> LENGTH: 42
<212> TYPE: DNA
<213> ORGANISM: Artificial Sequence
<220> FEATURE:
<223> OTHER INFORMATION: Synthetic Primer

<400> SEQUENCE: 6
acaccaacca cccaactatc tatgaaccta gccatggcca tc                        42

<210> SEQ ID NO 7
<211> LENGTH: 39

```
<212> TYPE: DNA
<213> ORGANISM: Artificial Sequence
<220> FEATURE:
<223> OTHER INFORMATION: Synthetic Primer

<400> SEQUENCE: 7
gtcgaccgca tgaacgaaaa tctgttcgct tcattcatt                    39

<210> SEQ ID NO 8
<211> LENGTH: 39
<212> TYPE: DNA
<213> ORGANISM: Artificial Sequence
<220> FEATURE:
<223> OTHER INFORMATION: Synthetic Primer

<400> SEQUENCE: 8
ccgggcggcc gctgtgttgt cgtgcaggta gaggcttac                    39

<210> SEQ ID NO 9
<211> LENGTH: 33
<212> TYPE: DNA
<213> ORGANISM: Artificial Sequence
<220> FEATURE:
<223> OTHER INFORMATION: Synthetic Primer

<400> SEQUENCE: 9
cgctctagaa tggccgcatc tccgcacact ctc                          33

<210> SEQ ID NO 10
<211> LENGTH: 33
<212> TYPE: DNA
<213> ORGANISM: Artificial Sequence
<220> FEATURE:
<223> OTHER INFORMATION: Synthetic Primer

<400> SEQUENCE: 10
gcggtcgact tcaagatacc agacagagcc tcc                          33

<210> SEQ ID NO 11
<211> LENGTH: 38
<212> TYPE: DNA
<213> ORGANISM: Artificial Sequence
<220> FEATURE:
<223> OTHER INFORMATION: Synthetic Primer

<400> SEQUENCE: 11
cccgatcgga gcactgggac gcccaccgcc cctttccc                     38

<210> SEQ ID NO 12
<211> LENGTH: 39
<212> TYPE: DNA
<213> ORGANISM: Artificial Sequence
<220> FEATURE:
<223> OTHER INFORMATION: Synthetic Primer

<400> SEQUENCE: 12
cgcacgcgta aagcttctac aaatgtgaag gctgtaaca                    39

<210> SEQ ID NO 13
<211> LENGTH: 33
<212> TYPE: DNA
<213> ORGANISM: Artificial Sequence
<220> FEATURE:
<223> OTHER INFORMATION: Synthetic Primer

<400> SEQUENCE: 13
```
cgctctagaa tgttgagccg ggcagtgtgc ggc                                    33

<210> SEQ ID NO 14
<211> LENGTH: 33
<212> TYPE: DNA
<213> ORGANISM: Artificial Sequence
<220> FEATURE:
<223> OTHER INFORMATION: Synthetic Primer

<400> SEQUENCE: 14
gtcgaccgcg tcggggaggc tgtgcttctg cct                                    33

<210> SEQ ID NO 15
<211> LENGTH: 36
<212> TYPE: DNA
<213> ORGANISM: Artificial Sequence
<220> FEATURE:
<223> OTHER INFORMATION: Synthetic Primer

<400> SEQUENCE: 15
accacgatcg ttatgctgag tatgttaagc tcttta                                 36

<210> SEQ ID NO 16
<211> LENGTH: 36
<212> TYPE: DNA
<213> ORGANISM: Artificial Sequence
<220> FEATURE:
<223> OTHER INFORMATION: Synthetic Primer

<400> SEQUENCE: 16
cgcacgcgtc aatcacacaa agcatttact attttc                                 36

<210> SEQ ID NO 17
<211> LENGTH: 27
<212> TYPE: DNA
<213> ORGANISM: Artificial Sequence
<220> FEATURE:
<223> OTHER INFORMATION: Synthetic Primer

<400> SEQUENCE: 17
atggctcccg aagttttgcc aaaacct                                           27

<210> SEQ ID NO 18
<211> LENGTH: 27
<212> TYPE: DNA
<213> ORGANISM: Artificial Sequence
<220> FEATURE:
<223> OTHER INFORMATION: Synthetic Primer

<400> SEQUENCE: 18
ctgaaagata ccagccttcc tcatctc                                           27

<210> SEQ ID NO 19
<211> LENGTH: 1337
<212> TYPE: DNA
<213> ORGANISM: Artificial Sequence
<220> FEATURE:
<223> OTHER INFORMATION: Synthetic COX10 MTS-nATP6

<400> SEQUENCE: 19
gaattcgccc ttcgctctag aatggccgca tctccgcaca ctctctcctc acgcctcctg       60
acaggttgcg taggaggctc tgtctggtat cttgaagtcg accgcatgaa cgaaaatctg      120
ttcgcttcat tcattgcccc cacaatccta ggcctacccg ccgcagtact gatcattcta      180
tttccccctc tattgatccc cacctccaaa tatctcatca caaccgact aatcaccacc      240

```
caacaatggc taatcaaact aacctcaaaa caaatgatga ccatgcacaa cactaaagga    300
cgaacctggt ctcttatgct agtatcctta atcatttta ttgccacaac taacctcctc    360
ggactcctgc ctcactcatt tacaccaacc acccaactat ctatgaacct agccatggcc    420 atcccttat gggcgggcac agtgattatg ggctttcgct ctaagattaa aaatgcccta    480
gcccacttct taccacaagg cacacctaca ccccttatcc ccatgctagt tattatcgaa    540
accatcagcc tactcattca accaatggcc ctggccgtac gcctaaccgc taacattact    600
gcaggccacc tactcatgca cctaattgga agcgccaccc tagcaatgtc aaccattaac    660
cttccctcta cacttatcat cttcacaatt ctaattctac tgactatcct agaaatcgct    720
gtcgccttaa tccaagccta cgttttcaca cttctagtaa gcctctacct gcacgacaac    780
acagcggccg cccggaaggg cgaattcgat atcaagctta tcgataccgt cgacctcgag    840
gattacaagg atgacgacga taagtagggc ccggtacctt aattaattaa ggtaccaggt    900
aagtgtaccc aattcgccct atagtgagtc gtattacaat tcactcgatc gcccttccca    960
acagttgcgc agcctgaatg gcgaatggag atccaatttt taagtgtata atgtgttaaa   1020
ctactgattc taattgtttg tgtattttag attcacagtc ccaaggctca tttcaggccc   1080
ctcagtcctc acagtctgtt catgatcata atcagccata ccacatttgt agaggtttta   1140
cttgctttaa aaacctcccc acacctcccc ctgaacctga acataaaat gaatgcaatt   1200 gttgttgtta acttgtttat tgcagcttat aatggttaca aataaagcaa tagcatcaca   1260
aatttcacaa ataaagcatt ttttcactg cattctagtt gtggtttgtc caaactcatc   1320
aatgtatctt aacgcgt                                                 1337
```

<210> SEQ ID NO 20
<211> LENGTH: 1356
<212> TYPE: DNA
<213> ORGANISM: Artificial Sequence
<220> FEATURE:
<223> OTHER INFORMATION: Synthetic SOD2MTS-nATP6

<400> SEQUENCE: 20

```
gaattcgccc ttcgctctag aatgttgagc cgggcagtgt gcggcaccag caggcagctg     60
gctccggttt tggggtatct gggctccagg cagaagcaca gcctccccga cgcggtcgac    120
cgcatgaacg aaaatctgtt cgcttcattc attgcccca caatcctagg cctacccgcc    180
gcagtactga tcattctatt tcccctcta ttgatcccca cctccaaata tctcatcaac    240
aaccgactaa tcaccaccca acaatggcta atcaaactaa cctcaaaaca aatgatgacc    300
atgcacaaca ctaaaggacg aacctggtct cttatgctag tatccttaat catttttatt    360
gccacaacta acctcctcgg actcctgcct cactcattta caccaaccac ccaactatct    420
atgaacctag ccatggccat cccttatgg gcgggcacag tgattatggg ctttcgctct    480
aagattaaaa atgccctagc ccacttctta ccacaaggca cacctacacc cttatcccc    540 atgctagtta ttatcgaaac catcagccta ctcattcaac caatggccct ggccgtacgc    600
ctaaccgcta acattactgc aggccaccta ctcatgcacc taattggaag cgccacccta    660
gcaatgtcaa ccattaacct tccctctaca cttatcatct tcacaattct aattctactg    720
actatcctag aaatcgctgt cgccttaatc caagcctacg ttttcacact tctagtaagc    780
ctctacctgc acgacaacac agcggccgcc cggtaagggc gaattcgata tcaagcttat    840
cgataccgtc gacctcgagg attacaagga tgacgacgat aagtagggcc cggtacctta    900
```

```
attaattaag gtaccaggta agtgtaccca attcgcccta tagtgagtcg tattacaatt   960
cactcgatcg cccttcccaa cagttgcgca gcctgaatgg cgaatggaga tccaattttt  1020
aagtgtataa tgtgttaaac tactgattct aattgtttgt gtattttaga ttcacagtcc  1080
caaggctcat ttcaggcccc tcagtcctca cagtctgttc atgatcataa tcagccatac  1140
cacatttgta gaggttttac ttgctttaaa aaacctccca cacctccccc tgaacctgaa  1200
acataaaatg aatgcaattg ttgttgttaa cttgtttatt gcagcttata atggttacaa  1260
ataaagcaat agcatcacaa atttcacaaa taaagcattt ttttcactgc attctagttg  1320
tggtttgtcc aaactcatca atgtatctta acgcgt                            1356

<210> SEQ ID NO 21
<211> LENGTH: 2381
<212> TYPE: DNA
<213> ORGANISM: Artificial Sequence
<220> FEATURE:
<223> OTHER INFORMATION: Synthetic COX10MTS-nATP6-COX10 3'UTR

<400> SEQUENCE: 21
gaattcgccc ttcgctctag aatggccgca tctccgcaca ctctctcctc acgcctcctg    60
acaggttgcg taggaggctc tgtctggtat cttgaagtcg accgcatgaa cgaaaatctg   120
ttcgcttcat tcattgcccc cacaatccta ggcctacccg ccgcagtact gatcattcta   180
tttccccctc tattgatccc cacctccaaa tatctcatca caaccgact  aatcaccacc   240 caacaatggc taatcaaact aacctcaaaa caaatgatga ccatgcacaa cactaaagga   300
cgaacctggt ctcttatgct agtatcctta atcatttta ttgccacaac taacctcctc   360
ggactcctgc ctcactcatt tacaccaacc acccaactat ctatgaacct agccatggcc   420
atccccttat gggcgggcac agtgattatg ggctttcgct ctaagattaa aaatgcccta   480
gcccacttct taccacaagg cacacctaca ccccttatcc ccatgctagt tattatcgaa   540
accatcagcc tactcattca accaatggcc ctggccgtac gcctaaccgc taacattact   600
gcaggccacc tactcatgca cctaattgga agcgccaccc tagcaatgtc aaccattaac   660
cttccctcta cacttatcat cttcacaatt ctaattctac tgactatcct agaaatcgct   720
gtcgccttaa tccaagccta cgttttcaca cttctagtaa gcctctacct gcacgacaac   780
acagcggccg cccggaaggg cgaattcgat atcaagctta tcgataccgt cgacctcgag   840
gattacaagg atgacgacga taagtagggc ccggtacctt aattaattaa ggtaccaggt   900
aagtgtaccc aattcgccct atagtgagtc gtattacaat tcactcgatc ggagcactgg   960 gacgccacc gccccttttcc ctccgctgcc aggcgagcat gttgtggtaa ttctggaaca  1020
caagaagaga aattgctggg tttagaacaa gattataaac gaattcggtg cccagtgatc  1080
acttgacagt tttttttttt tttaaatatt acccaaaatg ctcccaaat  aagaaatgca  1140 tcagctcagt cagtgaatac aaaaaaggaa ttattttttcc ctttgagggt ctttatacat  1200
ctctcctcca accccaccct ctattctgtt tcttcctcct cacatggggg tacacataca  1260
cagcttcctc ttttggttcc atccttacca ccacaccaca cgcacactcc acatgcccag  1320
cagagtggca cttggtggcc agaaagtgtg agcctcatga tctgctgtct gtagttctgt  1380
gagctcaggt ccctcaaagg cctcggagca cccccttcct ggtgactgag ccagggcctg  1440
catttttggt tttccccacc ccacacattc tcaaccatag tccttctaac aataccaata  1500
gctaggaccc ggctgctgtg cactgggact ggggattcca catgtttgcc ttgggagtct  1560
caagctggac tgccagcccc tgtcctccct tcacccccat tgcgtatgag catttcagaa  1620
```

```
ctccaaggag tcacaggcat ctttatagtt cacgttaaca tatagacact gttggaagca    1680
gttccttcta aaagggtagc cctggactta ataccagccg gatacctctg gcccccaccc    1740
cattactgta cctctggagt cactactgtg ggtcgccact cctctgctac acagcacggc    1800
tttttcaagg ctgtattgag aagggaagtt aggaagaagg gtgtgctggg ctaaccagcc    1860
cacagagctc acattcctgt cccttgggtg aaaaatacat gtccatcctg atatctcctg    1920
aattcagaaa ttagcctcca catgtgcaat ggctttaaga gccagaagca gggttctggg    1980
aattttgcaa gttatcctgt ggccaggtgt ggtctcggtt accaaatacg gttacctgca    2040 gcttttagt cctttgtgct cccacgggtc tgcagagtcc catctgccca aaggtcttga     2100
agcttgacag gatgttttca ttactcagtc tcccagggca ctgctggtcc gtagggattc    2160
attggtcggg gtgggagagt taaacaacat ttaaacagag ttctctcaaa aatgtctaaa    2220
gggattgtag gtagataaca tccaatcact gtttgcactt atctgaaatc ttccctcttg    2280
gctgccccca ggtatttact gtggagaaca ttgcatagga atgtctggaa aaagctccta    2340
caacttgtta cagccttcac atttgtagaa gctttacgcg t                        2381
```

<210> SEQ ID NO 22
<211> LENGTH: 1179
<212> TYPE: DNA
<213> ORGANISM: Artificial Sequence
<220> FEATURE:
<223> OTHER INFORMATION: Synthetic SOD2MTS-nATP6-SOD2 3'UTR

<400> SEQUENCE: 22

```
gaattcgccc ttcgctctag aatgttgagc cgggcagtgt gcggcaccag caggcagctg     60
gctccggttt tggggtatct gggctccagg cagaagcaca gcctcccga cgcggtcgac     120 cgcatgaacg aaaatctgtt cgcttcattc attgcccca caatcctagg cctacccgcc     180
gcagtactga tcattctatt tccccctcta ttgatcccca cctccaaata tctcatcaac     240
aaccgactaa tcaccaccca acaatggcta atcaaactaa cctcaaaaca aatgatgacc     300
atgcacaaca ctaaaggacg aacctggtct cttatgctag tatccttaat catttttatt     360
gccacaacta acctcctcgg actcctgcct cactcattta caccaaccac ccaactatct     420
atgaacctag ccatggccat ccccttatgg gcgggcacag tgattatggg ctttcgctct     480
aagattaaaa atgccctagc ccacttctta ccacaaggca cacctacacc ccttatcccc     540
atgctagtta ttatcgaaac catcagccta ctcattcaac caatggccct ggccgtacgc     600
ctaaccgcta acattactgc aggccaccta ctcatgcacc taattggaag cgccacccta    660
gcaatgtcaa ccattaacct tccctctaca cttatcatct tcacaattct aattctactg    720
actatcctag aaatcgctgt cgccttaatc caagcctacg ttttcacact tctagtaagc    780
ctctacctgc acgacaacac agcggccgcc cggtaagggc gaattcgata tcaagcttat    840
cgataccgtc gacctcgagg attacaagga tgacgacgat aagtagggcc cggtaccta    900 attaattaag gtaccaggta agtgtaccca attcgcccta tagtgagtcg tattacaatt    960
cactcgatcg ttatgctgag tatgttaagc tctttatgac tgttttgta gtggtataga    1020 gtactgcaga atacagtaag ctgctctatt gtagcatttc ctgatgttgc ttagtcactt    1080
atttcataaa caacttaatg ttctgaataa tttcttacta acatttgt tattgggcaa     1140 gtgattgaaa atagtaaatg ctttgtgtga ttgacgcgt                            1179
```

<210> SEQ ID NO 23

<211> LENGTH: 1552
<212> TYPE: DNA
<213> ORGANISM: Artificial Sequence
<220> FEATURE:
<223> OTHER INFORMATION: Synthetic COX10MTS-nND1

<400> SEQUENCE: 23

| | | |
|---|---|---|
| gtcgacatgg ctgctagccc ccacactctg agcagccgcc tgctgaccgg ttgcgtgggc | 60 |
| ggctctgtgt ggtatctgga gaggagaacc atgccaatgg caaatctgct gctcctcatc | 120 |
| gtgccaatcc tgatcgccat ggccttcctc atgctgactg aaagaaaaat tctgggatac | 180 |
| atgcagctca ggaagggggcc taacgtggtg ggaccttatg gactgctcca gcccttttgct | 240 |
| gatgctatga agctgttcac aaaagagccc ctgaaaccag ccacctctac aatcacccctg | 300 |
| tacattaccg ctcctaccct ggctctgaca attgccctgc tgctgtggac ccctctccct | 360 |
| atgccaaatc tctggtgaa cctgaatctg ggcctcctct ttatcctggc caccagcagc | 420 |
| ctggccgtgt actccatcct gtggagcgga tgggcttcta acagcaatta cgccctgatc | 480 |
| ggtgccctga gggccgtggc ccagaccatt tcttacgagg tgaccctcgc cattatcctg | 540 |
| ctctcaaccc tgctgatgag cggctctttc aacctctcaa ccctgattac aacccaggag | 600 |
| cacctctggc tgctcctccc cagctggcca ctggccatga tgtggtttat cagcaccctg | 660 |
| gctgagacaa accggacccc ctttgatctg gctgagggcg agtctgagct ggtctccgga | 720 |
| ttcaatattg agtacgcagc agggccattc gctctgttct tcatggccga gtatacaaat | 780 |
| attattatga tgaacacact gactactact atcttcctgg tactacata cgatgctctg | 840 |
| agtcccgaac tctacaccac ttacttcgtg accaaaaccc tgctgctgac tagcctgttc | 900 |
| ctgtggatca ggaccgccta tccacgattc cgatacgacc agctgatgca tctgctgtgg | 960 |
| aagaacttcc tgccactcac cctggctctg ctcatgtggt acgtgagtat gccaatcact | 1020 |
| atcagctcta tccctccaca gacctactcg aggaggatta caaggatgac gacgataagt | 1080 |
| agggcccggt accttaatta attaaggtac caggtaagtg tacccaattc gccctatagt | 1140 |
| gagtcgtatt acaattcact cgatcgccct tcccaacagt tgcgcagcct gaatggcgaa | 1200 |
| tggagatcca ttttttaagt gtataatgtg ttaaactact gattctaatt gtttgtgtat | 1260 |
| tttagattca cagtcccaag gctcatttca ggcccctcag tcctcacagt ctgttcatga | 1320 |
| tcataatcag ccataccaca tttgtagagg ttttacttgc tttaaaaaac ctcccacacc | 1380 |
| tccccctgaa cctgaaacat aaaatgaatg caattgttgt tgttaacttg tttattgcag | 1440 |
| cttataatgg ttacaaataa agcaatagca tcacaaattt cacaaataaa gcatttttt | 1500 |
| cactgcattc tagttgtggt tgtccaaac tcatcaatgt atcttaacgc gt | 1552 |

<210> SEQ ID NO 24
<211> LENGTH: 1973
<212> TYPE: DNA
<213> ORGANISM: Artificial Sequence
<220> FEATURE:
<223> OTHER INFORMATION: Synthetic COX10MTS-nND4

<400> SEQUENCE: 24

| | | |
|---|---|---|
| gtcgacatgg ccgcctcacc ccacaccctg agtagcaggc tgctgaccgg ctgtgtggga | 60 |
| ggaagcgtgt ggtatctgga gcggagaacc atgctgaagc tgatcgtgcc caccattatg | 120 |
| ctgctgccctc tgacatggct gtctaagaag cacatgatct ggattaacac aaccacccac | 180 |
| agcctgatta tctccatcat tcccctcctg ttcttcaacc agatcaacaa caacctgttc | 240 |
| tcctgctcac ctactttag cagcgatcca ctgacaaccc cactgctgat gctgacaacc | 300 |

```
tggctcctcc ccctgacaat catggcttcc cagaggcacc tgagcagcga gccactgtcc      360
cgcaaaaagc tgtacctgtc catgctgatt tctctccaga tctcactcat catgaccttc      420
actgccaccg agctgattat gttctatatc ttcttcgaga ctactctgat ccctacactc      480
gccattatca cccggtgggg caaccagcct gagagactga atgccgggac ttattttctg      540
ttctacaccc tggtggggtc actgcccctg ctgattgccc tgatctacac ccataacaca      600
ctgggctctc tcaatatcct gctgctcaca ctgacagccc aggagctgtc caattcttgg      660
gctaacaatc tgatgtggct cgcatacact atggccttca tggtgaagat gccactctat      720
gggctccacc tctggctccc taaggcccac gtcgaagccc caattgcagg gtccatggtg      780
ctggcagctg tgctcctgaa gctgggtggc tatgggatga tgcgcctgac cctgatcctg      840
aatcctctca caaagcatat ggcttaccct tttctggtgc tgtccctgtg gggaatgatt      900
atgacaagct ctatttgcct gcgccagaca gacctgaaaa gcctgattgc ctacagcagt      960
atcagtcata tggcccctggt ggtgaccgct attctgattc agacaccatg gtcttttaca     1020
ggggccgtca ttctgatgat cgcccacgga ctgacctcat cactcctctt ctgtctggcc     1080
aactcaaact acgaaaggac acactcaaga attatgattc tgagccaggg actccagact     1140
ctgctccccc tcatggcctt ctggtggctg ctcgcctctc tcgccaacct ggccctccct     1200
cccacaatca atctgctggg cgagctcagc gtgctggtga ccacttttag ttggtccaac     1260
atcacactgc tgctcaccgg actcaatatg ctggtcaccg ccctgtacag tctgtacatg     1320
ttcaccacaa cacagtgggg tagcctcact catcacatta ataacatgaa gccttctttt     1380
actagggaaa atactctgat gtttatgcat ctctccccaa tcctcctcct gagtctgaac     1440
cccgacatca tcaccggctt tagctctctc gaggaggatt acaaggatga cgacgataag     1500
tagggcccgg taccttaatt aattaaggta ccaggtaagt gtacccaatt cgccctatag     1560
tgagtcgtat tacaattcac tcgatcgccc ttcccaacag ttgcgcagcc tgaatggcga     1620
atggagatcc aattttttaag tgtataatgt gttaaactac tgattctaat tgtttgtgta     1680
ttttagattc acagtcccaa ggctcatttc aggccctca gtcctcacag tctgttcatg      1740
atcataatca gccataccac atttgtagag gttttacttg ctttaaaaaa cctcccacac     1800
ctccccctga acctgaaaca taaaatgaat gcaattgttg ttgttaactt gtttattgca     1860
gcttataatg gttacaaata aagcaatagc atcacaaatt tcacaaataa agcatttttt     1920
tcactgcatt ctagttgtgg tttgtccaaa ctcatcaatg tatcttaacg cgt           1973
```

<210> SEQ ID NO 25
<211> LENGTH: 2595
<212> TYPE: DNA
<213> ORGANISM: Artificial Sequence
<220> FEATURE:
<223> OTHER INFORMATION: Synthetic COX10MTS-nND1-COX10 3'UTR

<400> SEQUENCE: 25

```
gtcgacatgg ctgctagccc ccacactctg agcagccgcc tgctgaccgg ttgcgtgggc       60
ggctctgtgt ggtatctgga gaggagaacc atgccaatgg caaatctgct gctcctcatc      120
gtgccaatcc tgatcgccat ggccttcctc atgctgactaa aagaaaaat tctgggatac      180 atgcagctca ggaaggggcc taacgtggtg ggaccttatg gactgctcca gcccttgct      240 gatgctatga agctgttcac aaaagagccc ctgaaaccag ccacctctac aatcaccctg      300
tacattaccg ctcctaccct ggctctgaca attgccctgc tgctgtggac ccctctccct      360
```

```
atgccaaatc ctctggtgaa cctgaatctg ggcctcctct ttatcctggc caccagcagc    420
ctggccgtgt actccatcct gtggagcgga tgggcttcta acagcaatta cgccctgatc    480
ggtgccctga gggccgtggc ccagaccatt tcttacgagg tgaccctcgc cattatcctg    540
ctctcaaccc tgctgatgag cggctctttc aacctctcaa ccctgattac aacccaggag    600
cacctctggc tgctcctccc cagctggcca ctggccatga tgtggtttat cagcaccctg    660
gctgagacaa accggacccc ctttgatctg gctgagggcg agtctgagct ggtctccgga    720
ttcaatattg agtacgcagc agggccattc gctctgttct tcatggccga gtatacaaat    780
attattatga tgaacacact gactactact atcttcctgg gtactacata cgatgctctg    840
agtcccgaac tctacaccac ttacttcgtg accaaaaccc tgctgctgac tagcctgttc    900
ctgtggatca ggaccgccta ccacgattc cgatacgacc agctgatgca tctgctgtgg    960
aagaacttcc tgccactcac cctggctctg ctcatgtggt acgtgagtat gccaatcact   1020
atcagctcta tccctccaca gacctactcg aggaggatta caaggatgac gacgataagt   1080
agggcccggt accttaatta attaaggtac caggtaagtg tacccaattc gccctatagt   1140
gagtcgtatt acaattcact cgatcggagc actgggacgc ccaccgcccc tttccctccg   1200
ctgccaggcg agcatgttgt ggtaattctg aacacaagag agaaattg ctgggttag    1260 aacaagatta taaacgaatt cggtgctcag tgatcacttg acagttttt tttttttaa    1320 atattaccca aaatgctccc caaataagaa atgcatcagc tcagtcagtg aatacaaaa    1380 aggaattatt tttccctttg agggtcttta tacatctctc ctccaacccc accctctatt   1440
ctgtttcttc ctcctcacat gggggtacac atacacagct cctcttttg gttccatcct    1500 taccaccaca ccacacgcac actccacatg cccagcagag tggcacttgg tggccagaaa   1560
gtgtgagcct catgatctgc tgtctgtagt tctgtgagct caggtccctc aaaggcctcg   1620
gagcaccccc ttcctggtga ctgagccagg gcctgcattt ttggttttcc ccaccccaca   1680
cattctcaac catagtcctt ctaacaatac caatagctag acccggctg ctgtgcactg    1740 ggactgggga ttccacatgt ttgccttggg agtctcaagc tggactgcca gcccctgtcc   1800
tcccttcacc cccattgcgt atgagcattt cagaactcca aggagtcaca ggcatcttta   1860
tagttcacgt taacatatag acactgttgg aagcagttcc ttctaaaagg gtagccctgg   1920
acttaatacc agccggatac ctctggcccc caccccatta ctgtacctct ggagtcacta   1980
ctgtgggtcg ccactcctct gctacacagc acggcttttt caaggctgta ttgagaaggg   2040
aagttaggaa aagggtgtg ctgggctaac cagcccacag agctcacatt cctgtccctt    2100
gggtgaaaaa tacatgtcca tcctgatatc tcctgaattc agaaattagc ctccacatgt   2160
gcaatggctt taagagccag aagcagggtt ctgggaattt tgcaagttat cctgtggcca   2220
ggtgtggtct cggttaccaa atacggttac ctgcagcttt ttagtccttt gtgctcccac   2280
gggtctgcag agtcccatct gcccaaaggt cttgaagctt gacaggatgt tttcattact   2340
cagtctccca gggcactgct ggtccgtagg gattcattgg tcggggtggg agagttaaac   2400
aacatttaaa cagagttctc tcaaaaatgt ctaaagggat tgtaggtaga taacatccaa   2460
tcactgtttg cacttatctg aaatcttccc tcttggctgc ccccaggtat ttactgtgga   2520
gaacattgca taggaatgtc tgaaaaagct tctacaactt gttacagcct tcacatttgt   2580
agaagcttta cgcgt                                                    2595

<210> SEQ ID NO 26
<211> LENGTH: 3016
```

<212> TYPE: DNA
<213> ORGANISM: Artificial Sequence
<220> FEATURE:
<223> OTHER INFORMATION: Synthetic COX10MTS-nND4-COX10 3'UTR

<400> SEQUENCE: 26

| | | | | | |
|---|---|---|---|---|---|
| gtcgacatgg | ccgcctcacc | ccacaccctg | agtagcaggc | tgctgaccgg | ctgtgtggga | 60 |
| ggaagcgtgt | ggtatctgga | gcggagaacc | atgctgaagc | tgatcgtgcc | caccattatg | 120 |
| ctgctgcctc | tgacatggct | gtctaagaag | cacatgatct | ggattaacac | aaccaccac | 180 |
| agcctgatta | tctccatcat | tcccctcctg | ttcttcaacc | agatcaacaa | caacctgttc | 240 |
| tcctgctcac | ctactttag | cagcgatcca | ctgacaaccc | cactgctgat | gctgacaacc | 300 |
| tggctcctcc | ccctgacaat | catggcttcc | agaggcacc | tgagcagcga | gccactgtcc | 360 |
| cgcaaaaagc | tgtacctgtc | catgctgatt | tctctccaga | tctcactcat | catgaccttc | 420 |
| actgccaccg | agctgattat | gttctatatc | ttcttcgaga | ctactctgat | ccctacactc | 480 |
| gccattatca | cccggtgggg | caaccagcct | gagagactga | atgccgggac | ttattttctg | 540 |
| ttctacaccc | tggtggggtc | actgcccctg | ctgattgccc | tgatctacac | ccataacaca | 600 |
| ctgggctctc | tcaatatcct | gctgctcaca | ctgacagccc | aggagctgtc | caattcttgg | 660 |
| gctaacaatc | tgatgtggct | cgcatacact | atggccttca | tggtgaagat | gccactctat | 720 |
| gggctccacc | tctggctccc | taaggcccac | gtcgaagccc | caattgcagg | gtccatggtg | 780 |
| ctggcagctg | tgctcctgaa | gctgggtggc | tatgggatga | tgcgcctgac | cctgatcctg | 840 |
| aatcctctca | caaagcatat | ggcttaccct | tttctggtgc | tgtccctgtg | gggaatgatt | 900 |
| atgacaagct | ctatttgcct | cgccagaca | gacctgaaaa | gcctgattgc | ctacagcagt | 960 |
| atcagtcata | tggcccctggt | ggtgaccgct | attctgattc | agacaccatg | gtcttttaca | 1020 |
| ggggccgtca | ttctgatgat | cgcccacgga | ctgacctcat | cactcctctt | ctgtctggcc | 1080 |
| aactcaaact | acgaaaggac | acactcaaga | attatgattc | tgagccaggg | actccagact | 1140 |
| ctgctccccc | tcatggcctt | ctggtggctg | ctcgcctctc | tcgccaacct | ggccctccct | 1200 |
| cccacaatca | atctgctggg | cgagctcagc | gtgctggtga | ccacttttag | ttggtccaac | 1260 |
| atcacactgc | tgctcaccgg | actcaatatg | ctggtcaccg | ccctgtacag | tctgtacatg | 1320 |
| ttcaccacaa | cacagtgggg | tagcctcact | catcacatta | taacatgaa | gccttctttt | 1380 |
| actagggaaa | atactctgat | gtttatgcat | ctctccccaa | tcctcctcct | gagtctgaac | 1440 |
| cccgacatca | tcaccggctt | tagctctctc | gaggaggatt | acaaggatga | cgacgataag | 1500 |
| tagggcccgg | taccttaatt | aattaaggta | ccaggtaagt | gtacccaatt | cgccctatag | 1560 |
| tgagtcgtat | tacaattcac | tcgatcggag | cactgggacg | cccaccgccc | ctttccctcc | 1620 |
| gctgccaggc | gagcatgttg | tggtaattct | ggaacacaag | aagagaaatt | gctgggttta | 1680 |
| gaacaagatt | ataacgaat | tcggtgctca | gtgatcactt | gacagttttt | tttttttta | 1740 |
| aatattaccc | aaaatgctcc | ccaaataaga | aatgcatcag | ctcagtcagt | gaatacaaaa | 1800 |
| aaggaattat | ttttcccttt | gagggtcttt | atacatctct | cctccaaccc | caccctctat | 1860 |
| tctgtttctt | cctcctcaca | tgggggtaca | catacacagc | ttcctcttt | ggttccatcc | 1920 |
| ttaccaccac | accacacgca | cactccacat | gcccagcaga | gtggcacttg | gtggccagaa | 1980 |
| agtgtgagcc | tcatgatctg | ctgtctgtag | ttctgtgagc | tcaggtccct | caaaggcctc | 2040 |
| ggagcaccc | cttcctggtg | actgagccag | ggcctgcatt | tttggttttc | ccacccac | 2100 |
| acattctcaa | ccatagtcct | tctaacaata | ccaatagcta | ggacccggct | gctgtgcact | 2160 |

-continued

```
gggactgggg attccacatg tttgccttgg gagtctcaag ctggactgcc agcccctgtc    2220
ctcccttcac ccccattgcg tatgagcatt tcagaactcc aaggagtcac aggcatcttt    2280
atagttcacg ttaacatata gacactgttg gaagcagttc cttctaaaag ggtagccctg    2340
gacttaatac cagccggata cctctggccc ccaccccatt actgtacctc tggagtcact    2400
actgtgggtc gccactcctc tgctacacag cacggctttt tcaaggctgt attgagaagg    2460
gaagttagga agaagggtgt gctgggctaa ccagcccaca gagctcacat tcctgtccct    2520
tgggtgaaaa atacatgtcc atcctgatat ctcctgaatt cagaaattag cctccacatg    2580
tgcaatggct ttaagagcca gaagcagggt tctgggaatt ttgcaagtta tcctgtggcc    2640
aggtgtggtc tcggttacca aatacggtta cctgcagctt tttagtcctt tgtgctccca    2700
cgggtctgca gagtcccatc tgcccaaagg tcttgaagct tgacaggatg ttttcattac    2760
tcagtctccc agggcactgc tggtccgtag ggattcattg gtcggggtgg gagagttaaa    2820
caacatttaa acagagttct ctcaaaaatg tctaaaggga ttgtaggtag ataacatcca    2880
atcactgttt gcacttatct gaaatcttcc ctcttggctg cccccaggta tttactgtgg    2940
agaacattgc ataggaatgt ctgaaaaagc ttctacaact tgttacagcc ttcacatttg    3000
tagaagcttt acgcgt                                                    3016
```

<210> SEQ ID NO 27
<211> LENGTH: 696
<212> TYPE: DNA
<213> ORGANISM: Artificial Sequence
<220> FEATURE:
<223> OTHER INFORMATION: Synthetic nATP6 (recoded ATP6)

<400> SEQUENCE: 27

```
atgaacgaaa atctgttcgc ttcattcatt gcccccacaa tcctaggcct acccgccgca      60
gtactgatca ttctatttcc ccctctattg atccccacct ccaaatatct catcaacaac     120
cgactaatca ccacccaaca atggctaatc aaactaacct caaaacaaat gatgaccatg     180
cacaacacta aaggacgaac ctggtctctt atgctagtat ccttaatcat ttttattgcc     240
acaactaacc tcctcggact cctgcctcac tcatttacac caaccaccca actatctatg     300
aacctagcca tggccatccc cttatgggcg ggcacagtga ttatgggctt cgctctaag     360 attaaaaatg ccctagccca cttcttacca caaggcacac ctacacccct atccccatg     420 ctagttatta tcgaaaccat cagcctactc attcaaccaa tggccctggc cgtacgccta     480
accgctaaca ttactgcagg ccacctactc atgcacctaa ttggaagcgc acccctagca     540
atgtcaacca ttaaccttcc ctctacactt atcatcttca caattctaat tctactgact     600
atcctagaaa tcgctgtcgc cttaatccaa gcctacgttt tcacacttct agtaagcctc     660
tacctgcacg acaacacagc ggccgcccgg aagggc                              696
```

<210> SEQ ID NO 28
<211> LENGTH: 956
<212> TYPE: DNA
<213> ORGANISM: Artificial Sequence
<220> FEATURE:
<223> OTHER INFORMATION: Synthetic nND1 (recoded ND1)

<400> SEQUENCE: 28

```
atgccaatgg caaatctgct gctcctcatc gtgccaatcc tgatcgccat ggccttcctc      60
atgctgactg aaagaaaaat tctgggatac atgcagctca ggaaggggcc taacgtggtg     120
ggaccttatg gactgctcca gcccttgct gatgctatga agctgttcac aaaagagccc     180
```

```
ctgaaaccag ccacctctac aatcaccctg tacattaccg ctcctaccct ggctctgaca    240
attgccctgc tgctgtggac ccctctccct atgccaaatc tctggtgaa cctgaatctg     300 ggcctcctct ttatcctggc caccagcagc ctggccgtgt actccatcct gtggagcgga    360
tgggcttcta acagcaatta cgccctgatc ggtgccctga gggccgtggc ccagaccatt    420
tcttacgagg tgaccctcgc cattatcctg ctctcaaccc tgctgatgag cggctctttc    480
aacctctcaa ccctgattac aacccaggag cacctctggc tgctcctccc cagctggcca    540
ctggccatga tgtggtttat cagcaccctg gctgagacaa accggacccc ctttgatctg    600
gctgagggcg agtctgagct ggtctccgga ttcaatattg agtacgcagc agggccattc    660
gctctgttct tcatggccga gtatacaaat attattatga tgaacacact gactactact    720
atcttcctgg gtactacata cgatgctctg agtcccgaac tctacaccac ttacttcgtg    780
accaaaaccc tgctgctgac tagcctgttc ctgtggatca ggaccgccta tccacgattc    840
cgatacgacc agctgatgca tctgctgtgg aagaacttcc tgccactcac cctggctctg    900
ctcatgtggt acgtgagtat gccaatcact atcagctcta tccctccaca gaccta        956
```

<210> SEQ ID NO 29
<211> LENGTH: 1377
<212> TYPE: DNA
<213> ORGANISM: Artificial Sequence
<220> FEATURE:
<223> OTHER INFORMATION: Synthetic nND4 (recoded ND4)

<400> SEQUENCE: 29

```
atgctgaagc tgatcgtgcc caccattatg ctgctgcctc tgacatggct gtctaagaag    60
cacatgatct ggattaacac aaccacccac agcctgatta tctccatcat tcccctcctg    120
ttcttcaacc agatcaacaa caacctgttc tcctgctcac ctactttag cagcgatcca     180 ctgacaaccc cactgctgat gctgacaacc tggctcctcc ccctgacaat catggcttcc    240
cagaggcacc tgagcagcga gccactgtcc cgcaaaaagc tgtacctgtc catgctgatt    300
tctctccaga tctcactcat catgaccttc actgccaccg agctgattat gttctatatc    360
ttcttcgaga ctactctgat ccctacactc gccattatca cccggtgggg caaccagcct    420
gagagactga atgccgggac ttattttctg ttctacaccc tggtggggtc actgccctg     480 ctgattgccc tgatctacac ccataacaca ctgggctctc tcaatatcct gctgctcaca    540
ctgacagccc aggagctgtc caattcttgg gctaacaatc tgatgtggct cgcatacact    600
atggccttca tggtgaagat gccactctat gggctccacc tctggctccc taaggcccac    660
gtcgaagccc caattgcagg gtccatggtg ctggcagctg tgctcctgaa gctgggtggc    720
tatgggatga tgcgcctgac cctgatcctg aatcctctca caaagcatat ggcttacct     780 tttctggtgc tgtccctgtg gggaatgatt atgacaagct ctatttgcct cgccagaca    840 gacctgaaaa gcctgattgc ctacagcagt atcagtcata tggccctggt ggtgaccgct    900
attctgattc agacaccatg gtcttttaca ggggccgtca ttctgatgat cgcccacgga    960
ctgacctcat cactcctctt ctgtctggcc aactcaaact acgaaaggac acactcaaga    1020
attatgattc tgagccaggg actccagact ctgctccccc tcatggcctt ctggtggctg    1080
ctcgcctctc tcgccaacct ggccctccct cccacaatca atctgctggg cgagctcagc    1140
gtgctggtga ccacttttag ttggtccaac atcacactgc tgctcaccgg actcaatatg    1200
ctggtcaccg ccctgtacag tctgtacatg ttcaccacaa cacagtgggg tagcctcact    1260
```

```
catcacatta taacatgaa gccttctttt actagggaaa atactctgat gtttatgcat    1320
ctctccccaa tcctcctcct gagtctgaac cccgacatca tcaccggctt tagctct      1377

<210> SEQ ID NO 30
<211> LENGTH: 84
<212> TYPE: DNA
<213> ORGANISM: Homo sapiens

<400> SEQUENCE: 30
atggccgcat ctccgcacac tctctcctca cgcctcctga caggttgcgt aggaggctct    60
gtctggtatc ttgaagtcga ccgc                                           84

<210> SEQ ID NO 31
<211> LENGTH: 102
<212> TYPE: DNA
<213> ORGANISM: Homo sapiens

<400> SEQUENCE: 31
atgttgagcc gggcagtgtg cggcaccagc aggcagctgg ctccggtttt ggggtatctg    60
ggctccaggc agaagcacag cctccccgac gcggtcgacc gc                      102

<210> SEQ ID NO 32
<211> LENGTH: 30
<212> TYPE: PRT
<213> ORGANISM: Homo sapiens

<400> SEQUENCE: 32

Met Ala Pro Tyr Ser Leu Leu Val Thr Arg Leu Gln Lys Ala Leu Gly
1               5                   10                  15

Val Arg Gln Tyr His Val Ala Ser Val Leu Cys Gln Arg Ala
            20                  25                  30

<210> SEQ ID NO 33
<211> LENGTH: 382
<212> TYPE: DNA
<213> ORGANISM: Homo sapiens

<400> SEQUENCE: 33
gggcagtgcc tccccgcccc gccgctggcg tcaagttcag ctccacgtgt gccatcagtg    60
gatccgatcc gtccagccat ggcttcctat tccaagatgg tgtgaccaga catgcttcct   120
gctccccgct tagcccacgg agtgactgtg gttgtggtgg ggggggttctt aaaataactt   180 tttagccccc gtcttcctat tttgagtttg gttcagatct taagcagctc catgcaactg   240 tatttattt tgatgacaag actcccatct aaagttttc tcctgcctga tcatttcatt    300
ggtggctgaa ggattctaga gaacctttg ttcttgcaag gaaaacaaga atccaaaacc    360
agaaaaaaaa aaaaaaaaaa aa                                            382

<210> SEQ ID NO 34
<211> LENGTH: 20
<212> TYPE: PRT
<213> ORGANISM: Homo sapiens

<400> SEQUENCE: 34

Met Leu Ser Arg Ala Val Cys Gly Thr Ser Arg Gln Leu Ala Pro Ala
1               5                   10                  15

Leu Gly Tyr Leu
            20
```

```
<210> SEQ ID NO 35
<211> LENGTH: 214
<212> TYPE: DNA
<213> ORGANISM: Homo sapiens

<400> SEQUENCE: 35
accacgatcg ttatgctgat catacccctaa tgatcccagc aagataacgt cctgtcttct    60
aagatgtgca tcaagcctgg tacatactga aaccctata aggtcctgga taatttttgt    120
ttgattattc attgaagaaa catttatttt ccaattgtgt gaagttttg actgttaata    180 aaagaatctg tcaaccatca aaaaaaaaaa aaaa                                 214

<210> SEQ ID NO 36
<211> LENGTH: 63
<212> TYPE: PRT
<213> ORGANISM: Homo sapiens

<400> SEQUENCE: 36

Met Leu Gly Phe Val Gly Arg Val Ala Ala Pro Ala Ser Gly Ala
1               5                   10                  15

Leu Arg Arg Leu Thr Pro Ser Ala Ser Leu Pro Pro Ala Gln Leu Leu
                20                  25                  30

Leu Arg Ala Ala Pro Thr Ala Val His Pro Val Arg Asp Tyr Ala Ala
            35                  40                  45

Gln Thr Ser Pro Ser Pro Lys Ala Gly Ala Ala Thr Gly Arg Ile
        50                  55                  60

<210> SEQ ID NO 37
<211> LENGTH: 162
<212> TYPE: DNA
<213> ORGANISM: Homo sapiens

<400> SEQUENCE: 37
ggggtctttg tcctctgtac tgtctctctc cttgccccta acccaaaaag cttcattttt    60
ctgtgtaggc tgcacaagag ccttgattga agatatattc tttctgaaca gtatttaagg   120
tttccaataa aatgtacacc cctcagaaaa aaaaaaaaaa aa                        162

<210> SEQ ID NO 38
<211> LENGTH: 36
<212> TYPE: PRT
<213> ORGANISM: Homo sapiens

<400> SEQUENCE: 38

Met Leu Ser Val Ala Ala Arg Ser Gly Pro Phe Ala Pro Val Leu Ser
1               5                   10                  15

Ala Thr Ser Arg Gly Val Ala Gly Ala Leu Arg Pro Leu Val Gln Ala
                20                  25                  30

Thr Val Pro Ala
        35

<210> SEQ ID NO 39
<211> LENGTH: 233
<212> TYPE: DNA
<213> ORGANISM: Homo sapiens

<400> SEQUENCE: 39
gagacttgga ctcaagtcat aggcttcttt cagtctttat gtcacctcag gagacttatt    60
tgagaggaag cctctgtgtac ttgaagttga tttgaaatat gtaagaattg atgatgtatt   120
tgcaaacatt aatgtgaaat aaattgaatt taatgttgaa tactttcagg cattcactta   180
```
ataaagacac tgttaagcac tgttatgctc agtcaaaaaa aaaaaaaaaa aaa    233

<210> SEQ ID NO 40
<211> LENGTH: 20
<212> TYPE: PRT
<213> ORGANISM: Homo sapiens

<400> SEQUENCE: 40

Met Leu Ala Thr Arg Arg Leu Leu Gly Trp Ser Leu Pro Ala Arg Val
1               5                   10                  15

Ser Val Arg Phe
            20

<210> SEQ ID NO 41
<211> LENGTH: 102
<212> TYPE: DNA
<213> ORGANISM: Homo sapiens

<400> SEQUENCE: 41
cccaccaccc tggcctgctg tcctgcgtct atccatgtgg aatgctggac aataaagcga    60
gtgctgccca ccctccaaaa aaaaaaaaaa aaaaaaaaaa aa    102

<210> SEQ ID NO 42
<211> LENGTH: 43
<212> TYPE: PRT
<213> ORGANISM: Homo sapiens

<400> SEQUENCE: 42

Met Phe Phe Ser Ala Ala Leu Arg Ala Arg Ala Ala Gly Leu Thr Ala
1               5                   10                  15

His Trp Gly Arg His Val Arg Asn Leu His Lys Thr Ala Met Gln Asn
            20                  25                  30

Gly Ala Gly Gly Ala Leu Phe Val His Arg Asp
        35                  40

<210> SEQ ID NO 43
<211> LENGTH: 97
<212> TYPE: DNA
<213> ORGANISM: Homo sapiens

<400> SEQUENCE: 43
tttatattga actgtaaata tgtcactaga gaaataaaat atggacttcc aatctacgta    60
aaaaaaaaaa aaaaaaaaaa aaaaaaaaaa aaaaaaa    97

<210> SEQ ID NO 44
<211> LENGTH: 24
<212> TYPE: PRT
<213> ORGANISM: Homo sapiens

<400> SEQUENCE: 44

Met Leu Arg Ala Ala Ala Arg Phe Gly Pro Arg Leu Gly Arg Arg Leu
1               5                   10                  15

Leu Ser Ala Ala Ala Thr Gln Ala
            20

<210> SEQ ID NO 45
<211> LENGTH: 450
<212> TYPE: DNA
<213> ORGANISM: Homo sapiens

<400> SEQUENCE: 45

```
gaatcatgca agcttcctcc ctcagccatt gatggaaagt tcagcaagat cagcaacaaa      60
accaagaaaa atgatccttg cgtgctgaat atctgaaaag agaaattttt cctacaaaat     120
ctcttgggtc aagaaagttc tagaatttga attgataaac atggtgggtt ggctgagggt     180
aagagtatat gaggaacctt ttaaacgaca acaatactgc tagcttttcag gatgattttt     240 aaaaaataga ttcaaatgtg ttatcctctc tctgaaacgc ttcctataac tcgagtttat     300
aggggaagaa aaagctattg tttacaatta tatccccatt aaggcaactg ctacaccctg     360
ctttgtattc tgggctaaga ttcattaaaa actagctgct cttaaaaaaa aaaaaaaaa     420 aaaaaaaaaa aaaaaaaaaa aaaaaaaaaa                                      450
```

<210> SEQ ID NO 46
<211> LENGTH: 20
<212> TYPE: PRT
<213> ORGANISM: Homo sapiens

<400> SEQUENCE: 46

```
Met Ala Ala Ser Pro His Thr Leu Ser Ser Arg Leu Leu Thr Gly Cys
1               5                   10                  15

Val Gly Gly Ser
            20
```

<210> SEQ ID NO 47
<211> LENGTH: 1424
<212> TYPE: DNA
<213> ORGANISM: Homo sapiens

<400> SEQUENCE: 47

```
gagcactggg acgcccaccg cccctttccc tccgctgcca ggcgagcatg ttgtggtaat      60
tctggaacac aagaagagaa attgctgggt ttagaacaag attataaacg aattcggtgc     120
ccagtgatca cttgacagtt ttttttttt ttaaatatta cccaaaatgc tccccaaata     180
agaaatgcat cagctcagtc agtgaataca aaaaggaat tattttttccc tttgagggtc     240 tttatacatc tctcctccaa ccccaccctc tattctgttt cttcctcctc acatgggggt     300
acacatacac agcttcctct tttggttcca tccttaccac cacaccacac gcacactcca     360
catgcccagc agagtggcac ttggtggcca gaaagtgtga gcctcatgat ctgctgtctg     420
tagttctgtg agctcaggtc cctcaaaggc tcggagcac ccccttcctg gtgactgagc     480
cagggcctgc attttggtt tccccaccc cacacattct caaccatagt ccttctaaca     540
ataccaatag ctaggacccg gctgctgtgc actgggactg gggattccac atgtttgcct     600
tgggagtctc aagctggact gccagcccct gtcctccctt cacccccatt gcgtatgagc     660
atttcagaac tccaaggagt cacaggcatc tttatagttc acgttaacat atagacactg     720
ttggaagcag ttccttctaa aagggtagcc ctggacttaa taccagccgg atacctctgg     780 ccccacccc attactgtac ctctggagtc actactgtgg gtcgccactc ctctgctaca     840
cagcacggct ttttcaaggc tgtattgaga agggaagtta ggaagaaggg tgtgctgggc     900
taaccagccc acagagctca cattcctgtc ccttgggtga aaaatacatg tccatcctga     960
tatctcctga attcagaaat tagcctccac atgtgcaatg ctttaagag ccagaagcag    1020 ggttctggga attttgcaag ttatcctgtg gccaggtgtg gtctcggtta ccaaatacgg    1080
ttacctgcag ctttttagtc ctttgtgctc ccacgggtct gcagagtccc atctgcccaa    1140
aggtcttgaa gcttgacagg atgttttcat tactcagtct cccagggcac tgctggtccg    1200
```

-continued

```
tagggattca ttggtcgggg tgggagagtt aaacaacatt taaacagagt tctctcaaaa    1260
atgtctaaag ggattgtagg tagataacat ccaatcactg tttgcactta tctgaaatct    1320
tccctcttgg ctgccccag gtatttactg tggagaacat tgcataggaa tgtctggaaa     1380
aagctcctac aacttgttac agccttcaca tttgtagaag cttt                     1424
```

<210> SEQ ID NO 48
<211> LENGTH: 780
<212> TYPE: PRT
<213> ORGANISM: Homo sapiens

<400> SEQUENCE: 48

```
Met Ala Pro Tyr Ser Leu Leu Val Thr Arg Leu Gln Lys Ala Leu Gly
1               5                   10                  15

Val Arg Gln Tyr His Val Ala Ser Val Leu Cys Gln Arg Ala Lys Val
            20                  25                  30

Ala Met Ser His Phe Glu Pro Asn Glu Tyr Ile His Tyr Asp Leu Leu
        35                  40                  45

Glu Lys Asn Ile Asn Ile Val Arg Lys Arg Leu Asn Arg Pro Leu Thr
    50                  55                  60

Leu Ser Glu Lys Ile Val Tyr Gly His Leu Asp Asp Pro Ala Ser Gln
65                  70                  75                  80

Glu Ile Glu Arg Gly Lys Ser Tyr Leu Arg Leu Arg Pro Asp Arg Val
                85                  90                  95

Ala Met Gln Asp Ala Thr Ala Gln Met Ala Met Leu Gln Phe Ile Ser
            100                 105                 110

Ser Gly Leu Ser Lys Val Ala Val Pro Ser Thr Ile His Cys Asp His
        115                 120                 125

Leu Ile Glu Ala Gln Val Gly Gly Glu Lys Asp Leu Arg Arg Ala Lys
    130                 135                 140

Asp Ile Asn Gln Glu Val Tyr Asn Phe Leu Ala Thr Ala Gly Ala Lys
145                 150                 155                 160

Tyr Gly Val Gly Phe Trp Lys Pro Gly Ser Gly Ile Ile His Gln Ile
                165                 170                 175

Ile Leu Glu Asn Tyr Ala Tyr Pro Gly Val Leu Leu Ile Gly Thr Asp
            180                 185                 190

Ser His Thr Pro Asn Gly Gly Gly Leu Gly Gly Ile Cys Ile Gly Val
        195                 200                 205

Gly Gly Ala Asp Ala Val Asp Val Met Ala Gly Ile Pro Trp Glu Leu
    210                 215                 220

Lys Cys Pro Lys Val Ile Gly Val Lys Leu Thr Gly Ser Leu Ser Gly
225                 230                 235                 240

Trp Ser Ser Pro Lys Asp Val Ile Leu Lys Val Ala Gly Ile Leu Thr
                245                 250                 255

Val Lys Gly Gly Thr Gly Ala Ile Val Glu Tyr His Gly Pro Gly Val
            260                 265                 270

Asp Ser Ile Ser Cys Thr Gly Met Ala Thr Ile Cys Asn Met Gly Ala
        275                 280                 285

Glu Ile Gly Ala Thr Thr Ser Val Phe Pro Tyr Asn His Arg Met Lys
    290                 295                 300

Lys Tyr Leu Ser Lys Thr Gly Arg Glu Asp Ile Ala Asn Leu Ala Asp
305                 310                 315                 320

Glu Phe Lys Asp His Leu Val Pro Asp Pro Gly Cys His Tyr Asp Gln
                325                 330                 335
```

```
Leu Ile Glu Ile Asn Leu Ser Glu Leu Lys Pro His Ile Asn Gly Pro
                340                 345                 350

Phe Thr Pro Asp Leu Ala His Pro Val Ala Glu Val Gly Lys Val Ala
            355                 360                 365

Glu Lys Glu Gly Trp Pro Leu Asp Ile Arg Val Gly Leu Ile Gly Ser
        370                 375                 380

Cys Thr Asn Ser Ser Tyr Glu Asp Met Gly Arg Ser Ala Ala Val Ala
385                 390                 395                 400

Lys Gln Ala Leu Ala His Gly Leu Lys Cys Lys Ser Gln Phe Thr Ile
                405                 410                 415

Thr Pro Gly Ser Glu Gln Ile Arg Ala Thr Ile Glu Arg Asp Gly Tyr
            420                 425                 430

Ala Gln Ile Leu Arg Asp Leu Gly Gly Ile Val Leu Ala Asn Ala Cys
        435                 440                 445

Gly Pro Cys Ile Gly Gln Trp Asp Arg Lys Asp Ile Lys Lys Gly Glu
    450                 455                 460

Lys Asn Thr Ile Val Thr Ser Tyr Asn Arg Asn Phe Thr Gly Arg Asn
465                 470                 475                 480

Asp Ala Asn Pro Glu Thr His Ala Phe Val Thr Ser Pro Glu Ile Val
                485                 490                 495

Thr Ala Leu Ala Ile Ala Gly Thr Leu Lys Phe Asn Pro Glu Thr Asp
            500                 505                 510

Tyr Leu Thr Gly Thr Asp Gly Lys Lys Phe Arg Leu Glu Ala Pro Asp
        515                 520                 525

Ala Asp Glu Leu Pro Lys Gly Glu Phe Asp Pro Gly Gln Asp Thr Tyr
530                 535                 540

Gln His Pro Pro Lys Asp Ser Ser Gly Gln His Val Asp Val Ser Pro
545                 550                 555                 560

Thr Ser Gln Arg Leu Gln Leu Leu Glu Pro Phe Asp Lys Trp Asp Gly
            565                 570                 575

Lys Asp Leu Glu Asp Leu Gln Ile Leu Ile Lys Val Lys Gly Lys Cys
        580                 585                 590

Thr Thr Asp His Ile Ser Ala Ala Gly Pro Trp Leu Lys Phe Arg Gly
    595                 600                 605

His Leu Asp Asn Ile Ser Asn Asn Leu Leu Ile Gly Ala Ile Asn Ile
        610                 615                 620

Glu Asn Gly Lys Ala Asn Ser Val Arg Asn Ala Val Thr Gln Glu Phe
625                 630                 635                 640

Gly Pro Val Pro Asp Thr Ala Arg Tyr Tyr Lys Lys His Gly Ile Arg
                645                 650                 655

Trp Val Val Ile Gly Asp Glu Asn Tyr Gly Glu Gly Ser Ser Arg Glu
            660                 665                 670

His Ala Ala Leu Glu Pro Arg His Leu Gly Gly Arg Ala Ile Ile Thr
        675                 680                 685

Lys Ser Phe Ala Arg Ile His Glu Thr Asn Leu Lys Lys Gln Gly Leu
    690                 695                 700

Leu Pro Leu Thr Phe Ala Asp Pro Ala Asp Tyr Asn Lys Ile His Pro
705                 710                 715                 720

Val Asp Lys Leu Thr Ile Gln Gly Leu Lys Asp Phe Thr Pro Gly Lys
                725                 730                 735

Pro Leu Lys Cys Ile Ile Lys His Pro Asn Gly Thr Gln Glu Thr Ile
            740                 745                 750

Leu Leu Asn His Thr Phe Asn Glu Thr Gln Ile Glu Trp Phe Arg Ala
```

```
                755                 760                 765
Gly Ser Ala Leu Asn Arg Met Lys Glu Leu Gln Gln
            770                 775                 780

<210> SEQ ID NO 49
<211> LENGTH: 222
<212> TYPE: PRT
<213> ORGANISM: Homo sapiens

<400> SEQUENCE: 49

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 50
<211> LENGTH: 529
<212> TYPE: PRT
<213> ORGANISM: Homo sapiens

<400> SEQUENCE: 50

Met Leu Gly Phe Val Gly Arg Val Ala Ala Pro Ala Ser Gly Ala
1               5                   10                  15

Leu Arg Arg Leu Thr Pro Ser Ala Ser Leu Pro Pro Ala Gln Leu Leu
            20                  25                  30

Leu Arg Ala Ala Pro Thr Ala Val His Pro Val Arg Asp Tyr Ala Ala
        35                  40                  45

Gln Thr Ser Pro Ser Pro Lys Ala Gly Ala Ala Thr Gly Arg Ile Val
    50                  55                  60

Ala Val Ile Gly Ala Val Val Asp Val Gln Phe Asp Glu Gly Leu Pro
65                  70                  75                  80

Pro Ile Leu Asn Ala Leu Glu Val Gln Gly Arg Glu Thr Arg Leu Val
```

```
                85                  90                  95
Leu Glu Val Ala Gln His Leu Gly Glu Ser Thr Val Arg Thr Ile Ala
            100                 105                 110
Met Asp Gly Thr Glu Gly Leu Arg Gly Gln Lys Val Leu Asp Ser
            115                 120                 125
Gly Ala Pro Ile Lys Ile Pro Val Gly Pro Glu Thr Leu Gly Arg Ile
            130                 135                 140
Met Asn Val Ile Gly Glu Pro Ile Asp Glu Arg Gly Pro Ile Lys Thr
145                 150                 155                 160
Lys Gln Phe Ala Pro Ile His Ala Glu Ala Pro Glu Phe Met Glu Met
                165                 170                 175
Ser Val Glu Gln Glu Ile Leu Val Thr Gly Ile Lys Val Val Asp Leu
            180                 185                 190
Leu Ala Pro Tyr Ala Lys Gly Gly Lys Ile Gly Leu Phe Gly Gly Ala
            195                 200                 205
Gly Val Gly Lys Thr Val Leu Ile Met Glu Leu Ile Asn Asn Val Ala
            210                 215                 220
Lys Ala His Gly Gly Tyr Ser Val Phe Ala Gly Val Gly Glu Arg Thr
225                 230                 235                 240
Arg Glu Gly Asn Asp Leu Tyr His Glu Met Ile Glu Ser Gly Val Ile
                245                 250                 255
Asn Leu Lys Asp Ala Thr Ser Lys Val Ala Leu Val Tyr Gly Gln Met
            260                 265                 270
Asn Glu Pro Pro Gly Ala Arg Ala Arg Val Ala Leu Thr Gly Leu Thr
            275                 280                 285
Val Ala Glu Tyr Phe Arg Asp Gln Glu Gly Gln Asp Val Leu Leu Phe
            290                 295                 300
Ile Asp Asn Ile Phe Arg Phe Thr Gln Ala Gly Ser Glu Val Ser Ala
305                 310                 315                 320
Leu Leu Gly Arg Ile Pro Ser Ala Val Gly Tyr Gln Pro Thr Leu Ala
                325                 330                 335
Thr Asp Met Gly Thr Met Gln Glu Arg Ile Thr Thr Thr Lys Lys Gly
            340                 345                 350
Ser Ile Thr Ser Val Gln Ala Ile Tyr Val Pro Ala Asp Asp Leu Thr
            355                 360                 365
Asp Pro Ala Pro Ala Thr Thr Phe Ala His Leu Asp Ala Thr Thr Val
            370                 375                 380
Leu Ser Arg Ala Ile Ala Glu Leu Gly Ile Tyr Pro Ala Val Asp Pro
385                 390                 395                 400
Leu Asp Ser Thr Ser Arg Ile Met Asp Pro Asn Ile Val Gly Ser Glu
                405                 410                 415
His Tyr Asp Val Ala Arg Gly Val Gln Lys Ile Leu Gln Asp Tyr Lys
            420                 425                 430
Ser Leu Gln Asp Ile Ile Ala Ile Leu Gly Met Asp Glu Leu Ser Glu
            435                 440                 445
Glu Asp Lys Leu Thr Val Ser Arg Ala Arg Lys Ile Gln Arg Phe Leu
            450                 455                 460
Ser Gln Pro Phe Gln Val Ala Glu Val Phe Thr Gly His Met Gly Lys
465                 470                 475                 480
Leu Val Pro Leu Lys Glu Thr Ile Lys Gly Phe Gln Gln Ile Leu Ala
                485                 490                 495
Gly Glu Tyr Asp His Leu Pro Glu Gln Ala Phe Tyr Met Val Gly Pro
            500                 505                 510
```

```
Ile Glu Glu Ala Val Ala Lys Ala Asp Lys Leu Ala Glu Glu His Ser
            515                 520                 525
Ser

<210> SEQ ID NO 51
<211> LENGTH: 274
<212> TYPE: PRT
<213> ORGANISM: Homo sapiens

<400> SEQUENCE: 51

Met Leu Ser Val Ala Ala Arg Ser Gly Pro Phe Ala Pro Val Leu Ser
1               5                   10                  15

Ala Thr Ser Arg Gly Val Ala Gly Ala Leu Arg Pro Leu Val Gln Ala
            20                  25                  30

Thr Val Pro Ala Thr Pro Glu Gln Pro Val Leu Asp Leu Lys Arg Pro
        35                  40                  45

Phe Leu Ser Arg Glu Ser Leu Ser Gly Gln Ala Val Arg Arg Pro Leu
    50                  55                  60

Val Ala Ser Val Gly Leu Asn Val Pro Ala Ser Val Cys Tyr Ser His
65                  70                  75                  80

Thr Asp Ile Lys Val Pro Asp Phe Ser Glu Tyr Arg Arg Leu Glu Val
                85                  90                  95

Leu Asp Ser Thr Lys Ser Ser Arg Glu Ser Ser Glu Ala Arg Lys Gly
            100                 105                 110

Phe Ser Tyr Leu Val Thr Gly Val Thr Thr Val Gly Val Ala Tyr Ala
        115                 120                 125

Ala Lys Asn Ala Val Thr Gln Phe Val Ser Ser Met Ser Ala Ser Ala
    130                 135                 140

Asp Val Leu Ala Leu Ala Lys Ile Glu Ile Lys Leu Ser Asp Ile Pro
145                 150                 155                 160

Glu Gly Lys Asn Met Ala Phe Lys Trp Arg Gly Lys Pro Leu Phe Val
                165                 170                 175

Arg His Arg Thr Gln Lys Glu Ile Glu Gln Glu Ala Ala Val Glu Leu
            180                 185                 190

Ser Gln Leu Arg Asp Pro Gln His Asp Leu Asp Arg Val Lys Lys Pro
        195                 200                 205

Glu Trp Val Ile Leu Ile Gly Val Cys Thr His Leu Gly Cys Val Pro
    210                 215                 220

Ile Ala Asn Ala Gly Asp Phe Gly Gly Tyr Tyr Cys Pro Cys His Gly
225                 230                 235                 240

Ser His Tyr Asp Ala Ser Gly Arg Ile Arg Leu Gly Pro Ala Pro Leu
                245                 250                 255

Asn Leu Glu Val Pro Thr Tyr Glu Phe Thr Ser Asp Asp Met Val Ile
            260                 265                 270

Val Gly

<210> SEQ ID NO 52
<211> LENGTH: 464
<212> TYPE: PRT
<213> ORGANISM: Homo sapiens

<400> SEQUENCE: 52

Met Leu Ala Thr Arg Arg Leu Leu Gly Trp Ser Leu Pro Ala Arg Val
1               5                   10                  15

Ser Val Arg Phe Ser Gly Asp Thr Thr Ala Pro Lys Lys Thr Ser Phe
```

-continued

```
                20                  25                  30
Gly Ser Leu Lys Asp Glu Asp Arg Ile Phe Thr Asn Leu Tyr Gly Arg
            35                  40                  45
His Asp Trp Arg Leu Lys Gly Ser Leu Ser Arg Gly Asp Trp Tyr Lys
        50                  55                  60
Thr Lys Glu Ile Leu Leu Lys Gly Pro Asp Trp Ile Leu Gly Glu Ile
65                  70                  75                  80
Lys Thr Ser Gly Leu Arg Gly Arg Gly Ala Gly Phe Pro Thr Gly
                85                  90                  95
Leu Lys Trp Ser Phe Met Asn Lys Pro Ser Asp Gly Arg Pro Lys Tyr
                100                 105                 110
Leu Val Val Asn Ala Asp Glu Gly Glu Pro Gly Thr Cys Lys Asp Arg
            115                 120                 125
Glu Ile Leu Arg His Asp Pro His Lys Leu Leu Glu Gly Cys Leu Val
        130                 135                 140
Gly Gly Arg Ala Met Gly Ala Arg Ala Ala Tyr Ile Tyr Ile Arg Gly
145                 150                 155                 160
Glu Phe Tyr Asn Glu Ala Ser Asn Leu Gln Val Ala Ile Arg Glu Ala
                165                 170                 175
Tyr Glu Ala Gly Leu Ile Gly Lys Asn Ala Cys Gly Ser Gly Tyr Asp
                180                 185                 190
Phe Asp Val Phe Val Val Arg Gly Ala Gly Ala Tyr Ile Cys Gly Glu
            195                 200                 205
Glu Thr Ala Leu Ile Glu Ser Ile Glu Gly Lys Gln Gly Lys Pro Arg
        210                 215                 220
Leu Lys Pro Pro Phe Pro Ala Asp Val Gly Val Phe Gly Cys Pro Thr
225                 230                 235                 240
Thr Val Ala Asn Val Glu Thr Val Ala Val Ser Pro Thr Ile Cys Arg
                245                 250                 255
Arg Gly Gly Thr Trp Phe Ala Gly Phe Gly Arg Glu Arg Asn Ser Gly
                260                 265                 270
Thr Lys Leu Phe Asn Ile Ser Gly His Val Asn His Pro Cys Thr Val
            275                 280                 285
Glu Glu Glu Met Ser Val Pro Leu Lys Glu Leu Ile Glu Lys His Ala
        290                 295                 300
Gly Gly Val Thr Gly Gly Trp Asp Asn Leu Leu Ala Val Ile Pro Gly
305                 310                 315                 320
Gly Ser Ser Thr Pro Leu Ile Pro Lys Ser Val Cys Glu Thr Val Leu
                325                 330                 335
Met Asp Phe Asp Ala Leu Val Gln Ala Gln Thr Gly Leu Gly Thr Ala
                340                 345                 350
Ala Val Ile Val Met Asp Arg Ser Thr Asp Ile Val Lys Ala Ile Ala
            355                 360                 365
Arg Leu Ile Glu Phe Tyr Lys His Glu Ser Cys Gly Gln Cys Thr Pro
        370                 375                 380
Cys Arg Glu Gly Val Asp Trp Met Asn Lys Val Met Ala Arg Phe Val
385                 390                 395                 400
Arg Gly Asp Ala Arg Pro Ala Glu Ile Asp Ser Leu Trp Glu Ile Ser
                405                 410                 415
Lys Gln Ile Glu Gly His Thr Ile Cys Ala Leu Gly Asp Gly Ala Ala
            420                 425                 430
Trp Pro Val Gln Gly Leu Ile Arg His Phe Arg Pro Glu Leu Glu Glu
        435                 440                 445
```

-continued

Arg Met Gln Arg Phe Ala Gln Gln His Gln Ala Arg Gln Ala Ala Ser
    450                 455                 460

<210> SEQ ID NO 53
<211> LENGTH: 249
<212> TYPE: PRT
<213> ORGANISM: Homo sapiens

<400> SEQUENCE: 53

Met Phe Phe Ser Ala Ala Leu Arg Ala Arg Ala Ala Gly Leu Thr Ala
1               5                   10                  15

His Trp Gly Arg His Val Arg Asn Leu His Lys Thr Ala Met Gln Asn
            20                  25                  30

Gly Ala Gly Gly Ala Leu Phe Val His Arg Asp Thr Pro Glu Asn Asn
        35                  40                  45

Pro Asp Thr Pro Phe Asp Phe Thr Pro Glu Asn Tyr Lys Arg Ile Glu
    50                  55                  60

Ala Ile Val Lys Asn Tyr Pro Glu Gly His Lys Ala Ala Val Leu
65                  70                  75                  80

Pro Val Leu Asp Leu Ala Gln Arg Gln Asn Gly Trp Leu Pro Ile Ser
                85                  90                  95

Ala Met Asn Lys Val Ala Glu Val Leu Gln Val Pro Pro Met Arg Val
            100                 105                 110

Tyr Glu Val Ala Thr Phe Tyr Thr Met Tyr Asn Arg Lys Pro Val Gly
        115                 120                 125

Lys Tyr His Ile Gln Val Cys Thr Thr Thr Pro Cys Met Leu Arg Asn
    130                 135                 140

Ser Asp Ser Ile Leu Glu Ala Ile Gln Lys Lys Leu Gly Ile Lys Val
145                 150                 155                 160

Gly Glu Thr Thr Pro Asp Lys Leu Phe Thr Leu Ile Glu Val Glu Cys
                165                 170                 175

Leu Gly Ala Cys Val Asn Ala Pro Met Val Gln Ile Asn Asp Asn Tyr
            180                 185                 190

Tyr Glu Asp Leu Thr Ala Lys Asp Ile Glu Glu Ile Ile Asp Glu Leu
        195                 200                 205

Lys Ala Gly Lys Ile Pro Lys Pro Gly Pro Arg Ser Gly Arg Phe Ser
    210                 215                 220

Cys Glu Pro Ala Gly Gly Leu Thr Ser Leu Thr Glu Pro Pro Lys Gly
225                 230                 235                 240

Pro Gly Phe Gly Val Gln Ala Gly Leu
                245

<210> SEQ ID NO 54
<211> LENGTH: 517
<212> TYPE: PRT
<213> ORGANISM: Homo sapiens

<400> SEQUENCE: 54

Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60

-continued

```
Ile Cys Gln Val Ala Glu Gly Asp Lys Glu Asp Val Asp Lys Ala Val
 65                  70                  75                  80

Lys Ala Ala Arg Ala Ala Phe Gln Leu Gly Ser Pro Trp Arg Arg Met
                 85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
        355                 360                 365

Lys Ile Leu Gly Tyr Ile Asn Thr Gly Lys Gln Glu Gly Ala Lys Leu
    370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480
```

-continued

```
Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
            500                 505                 510

Pro Gln Lys Asn Ser
        515

<210> SEQ ID NO 55
<211> LENGTH: 443
<212> TYPE: PRT
<213> ORGANISM: Homo sapiens

<400> SEQUENCE: 55

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr Ile Gln Asp Ser
            20                  25                  30

Pro His Lys Phe Leu His Leu Leu Arg Asn Val Asn Lys Gln Trp Ile
        35                  40                  45

Thr Phe Gln His Phe Ser Phe Leu Lys Arg Met Tyr Val Thr Gln Leu
    50                  55                  60

Asn Arg Ser His Asn Gln Gln Val Arg Pro Lys Pro Glu Pro Val Ala
65                  70                  75                  80

Ser Pro Phe Leu Glu Lys Thr Ser Ser Gly Gln Ala Lys Ala Glu Ile
                85                  90                  95

Tyr Glu Met Arg Pro Leu Ser Pro Pro Ser Leu Ser Leu Ser Arg Lys
            100                 105                 110

Pro Asn Glu Lys Glu Leu Ile Glu Leu Glu Pro Asp Ser Val Ile Glu
        115                 120                 125

Asp Ser Ile Asp Val Gly Lys Glu Thr Lys Glu Lys Arg Trp Lys
    130                 135                 140

Glu Met Lys Leu Gln Val Tyr Asp Leu Pro Gly Ile Leu Ala Arg Leu
145                 150                 155                 160

Ser Lys Ile Lys Leu Thr Ala Leu Val Val Ser Thr Thr Ala Ala Gly
                165                 170                 175

Phe Ala Leu Ala Pro Gly Pro Phe Asp Trp Pro Cys Phe Leu Leu Thr
            180                 185                 190

Ser Val Gly Thr Gly Leu Ala Ser Cys Ala Ala Asn Ser Ile Asn Gln
        195                 200                 205

Phe Phe Glu Val Pro Phe Asp Ser Asn Met Asn Arg Thr Lys Asn Arg
    210                 215                 220

Pro Leu Val Arg Gly Gln Ile Ser Pro Leu Leu Ala Val Ser Phe Ala
225                 230                 235                 240

Thr Cys Cys Ala Val Pro Gly Val Ala Ile Leu Thr Leu Gly Val Asn
                245                 250                 255

Pro Leu Thr Gly Ala Leu Gly Leu Phe Asn Ile Phe Leu Tyr Thr Cys
            260                 265                 270

Cys Tyr Thr Pro Leu Lys Arg Ile Ser Ile Ala Asn Thr Trp Val Gly
        275                 280                 285

Ala Val Val Gly Ala Ile Pro Pro Val Met Gly Trp Thr Ala Ala Thr
    290                 295                 300

Gly Ser Leu Asp Ala Gly Ala Phe Leu Leu Gly Gly Ile Leu Tyr Ser
305                 310                 315                 320

Trp Gln Phe Pro His Phe Asn Ala Leu Ser Trp Gly Leu Arg Glu Asp
                325                 330                 335
```

```
Tyr Ser Arg Gly Gly Tyr Cys Met Met Ser Val Thr His Pro Gly Leu
            340                 345                 350

Cys Arg Arg Val Ala Leu Arg His Cys Leu Ala Leu Leu Val Leu Ser
        355                 360                 365

Ala Ala Ala Pro Val Leu Asp Ile Thr Thr Trp Thr Phe Pro Ile Met
370                 375                 380

Ala Leu Pro Ile Asn Ala Tyr Ile Ser Tyr Leu Gly Phe Arg Phe Tyr
385                 390                 395                 400

Val Asp Ala Asp Arg Ser Ser Arg Arg Leu Phe Phe Cys Ser Leu
                405                 410                 415

Trp His Leu Pro Leu Leu Leu Leu Met Leu Thr Cys Lys Arg Pro
                420                 425                 430

Ser Gly Gly Gly Asp Ala Gly Pro Pro Pro Ser
            435                 440
```

<210> SEQ ID NO 56
<211> LENGTH: 239
<212> TYPE: PRT
<213> ORGANISM: Homo sapiens

<400> SEQUENCE: 56

```
Met Ala Pro Ser Val Pro Ala Ala Glu Pro Glu Tyr Pro Lys Gly Ile
1               5                   10                  15

Arg Ala Val Leu Leu Gly Pro Pro Gly Ala Gly Lys Gly Thr Gln Ala
            20                  25                  30

Pro Arg Leu Ala Glu Asn Phe Cys Val Cys His Leu Ala Thr Gly Asp
        35                  40                  45

Met Leu Arg Ala Met Val Ala Ser Gly Ser Glu Leu Gly Lys Lys Leu
    50                  55                  60

Lys Ala Thr Met Asp Ala Gly Lys Leu Val Ser Asp Glu Met Val Val
65                  70                  75                  80

Glu Leu Ile Glu Lys Asn Leu Glu Thr Pro Leu Cys Lys Asn Gly Phe
                85                  90                  95

Leu Leu Asp Gly Phe Pro Arg Thr Val Arg Gln Ala Glu Met Leu Asp
            100                 105                 110

Asp Leu Met Glu Lys Arg Lys Glu Lys Leu Asp Ser Val Ile Glu Phe
        115                 120                 125

Ser Ile Pro Asp Ser Leu Leu Ile Arg Arg Ile Thr Gly Arg Leu Ile
    130                 135                 140

His Pro Lys Ser Gly Arg Ser Tyr His Glu Glu Phe Asn Pro Pro Lys
145                 150                 155                 160

Glu Pro Met Lys Asp Asp Ile Thr Gly Glu Pro Leu Ile Arg Arg Ser
                165                 170                 175

Asp Asp Asn Glu Lys Ala Leu Lys Ile Arg Leu Gln Ala Tyr His Thr
            180                 185                 190

Gln Thr Thr Pro Leu Ile Glu Tyr Tyr Arg Lys Arg Gly Ile His Ser
        195                 200                 205

Ala Ile Asp Ala Ser Gln Thr Pro Asp Val Val Phe Ala Ser Ile Leu
    210                 215                 220

Ala Ala Phe Ser Lys Ala Thr Cys Lys Asp Leu Val Met Phe Ile
225                 230                 235
```

<210> SEQ ID NO 57
<211> LENGTH: 922
<212> TYPE: DNA

<213> ORGANISM: Homo sapiens

<400> SEQUENCE: 57

```
tatcagaagg ccaggcgaga ctgcaacact gctcatcacc ccgcggcgtg atccctgctc    60
ttaggtgctg ggcagagggg aagggtggtc agggtgagga tggtgaggga gggctggtga   120
ggggctcaga ggaatacttg gaacaatagc agtgttattg tagtgtggca gtttcttta    180
tacataggtg agagttttta aagtgtaagg gaaaaattaa ttttttaaaa aacaccatgc   240
ttggagggtg ggggtagaaa tagacacaat attatttcta aggaatcggg ttttcattta   300
ctctggactg gtgaaaatat tttttaaagc cagtgctcta agacctcagc ttttatctca   360
gaaccccatg ggttccagac caagagtaca ggaaatcaaa ttgttgtcct gtctgtctat   420
agcttggaac agggagcttt gattactgac tccggttcca cacactgtaa gatcaaaaac   480
catctccaca tttgaaagag atgtaaggtg tattcatagg gatggtggct caacaaatca   540
agcaaactgg aatcaagggg aggggaaggg gaatgaaatg gaagggagg ctgattccct   600
tccctgact taccactaat ttactaggct acctactttc atgagtaacc tctcacagct   660
acccagcaca tgccacaatc ctatgctctt gccttctttt atctgcactg tgtgaaggga   720
ctcttttaaa taaatgagca agtgtcctaa gctatgtcat ccaaagattg tccttcccat   780
tctcaaatcc tgtgactggg atcactcaac agcactgtga tgtattattt tcaatgaggt   840
gccttctaaa actgaccaaa tgctgccttg tttggcccct aaatcaataa aatatgttaa   900
aatttgaaaa aaaaaaaaaa aa                                           922
```

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: synthetic Primer

<400> SEQUENCE: 58

```
cgactacggc gccctggaac ctcacatcaa cgc                                33
```

<210> SEQ ID NO 59
<211> LENGTH: 1425
<212> TYPE: DNA
<213> ORGANISM: Homo sapiens

<400> SEQUENCE: 59

```
gtgttgatgt atcacctccc caaaactgtt ggtaaatgtc agattttttc ctccaagagt    60
tgtgcttttg tgttatttgt tttcactcaa atattttgcc tcattattct tgttttaaaa   120
gaaagaaaac aggccgggca cagtggctca tgcctgtaat cccagcactt tgggaggtcg   180
aggtgggtgg atcacttggg gtcagggttt gagaccagcc tggccaacat ggcggaaccc   240
tgtctctacc aaaattacaa aaattagccg agcatggtgg cgcatgcctg tagtcgcagc   300
tactcgcgag gttgaggcag gagaattgct tgaacccagg aagtggcagt tgcagtgagc   360
cgagacgaca ccactgcact ccagcctggg tgacagaggg agactctgtc tcgaaagaaa   420
gaaagaaaaa aaggaaggaa ggagaaggaa ggaaggagaa gaaaaggtac ctgttctacg   480
tagaacacct ttggtggagt tccatcaact cgcaaagtag aatccttacc tactactctt   540
ctgataataa ttttaatatt ttttatgttt ggttgatgcg agcagctgca ctgctcatgc   600
agttagctag catgtgacat catgtgacaa agttcatgta attagatgga agaaacctca   660
```

```
ctgattaatt ttaagaacct tttagggatg caggaacaat gaagtggcca cagtatgtgc       720
tgtttttgaa gcatttttaa aaacgaattg tagttgtttt tcttcattta aaatggatct       780
gttggaggtt atgtgtgtat gttgtagttt tattgcagcc acaataattt taccaaagtt       840
ttcacatagg cagttagcct ttacttaata tcaagacaag tgaaaaaata ttggcatcga       900
tgaaaccgat aacattggcc tcattggatt tctttaccca ttcacagtgt aaagaagtta       960
ccttcatgct ttcattgtac ctgcaggcct gtgggcttgt acagtagata attaatttct      1020
aaaaagaaca gctgcctatt ttcttcctag gttaggttat atcttcataa tcacaagaat      1080
tagtgatggc aaaataaaat tttgcttatg aatcttttac attgtttata tatgattaat      1140
atcatcatat atattttctg tattaagctc atttggcttc atttaagctg tatacttagt      1200
catatatctt tcattagttc tatggatatg agcagatccc tttactggag cccagtatgt      1260
gctgtgtgag ttagaagtca ttcttgctga gaaggtgaat aggtagggat ttgccttgtt      1320
ttgtaagtct acaatttgcc aagagtaaat aacactggac cagctgtaaa agtaaacagt      1380
gtgtttatgc attgagatac taaagcattt aagaaaaaat taaaa                     1425

<210> SEQ ID NO 60
<211> LENGTH: 202
<212> TYPE: DNA
<213> ORGANISM: Homo sapiens

<400> SEQUENCE: 60
ttatgctgag tatgttaagc tctttatgac tgtttttgta gtggtataga gtactgcaga        60
atacagtaag ctgctctatt gtagcatttc ctgatgttgc ttagtcactt atttcataaa       120
caacttaatg ttctgaataa tttcttacta aacattttgt tattgggcaa gtgattgaaa       180
atagtaaatg ctttgtgtga tt                                               202
```